US011649456B2

(12) United States Patent
Gustincich et al.

(10) Patent No.: US 11,649,456 B2
(45) Date of Patent: May 16, 2023

(54) FUNCTIONAL NUCLEIC ACID MOLECULE AND USE THEREOF

(71) Applicants: FONDAZIONE ISTITUTO ITALIANO DI TECNOLOGIA, Genoa (IT); SCUOLA INTERNAZIONALE SUPERIORE DI STUDI AVANZATI, Trieste (IT)

(72) Inventors: Stefano Gustincich, Genoa (IT); Silvia Zucchelli, Genoa (IT)

(73) Assignees: FONDAZIONE ISTITUTO ITALIANO DI TECNOLOGIA, Genoa (IT); SCUOLA INTERNAZIONALE SUPERIORE DI STUDI AVANZATI, Trieste (IT)

( * ) Notice: Subject to any disclaimer, the term of this patent is extended or adjusted under 35 U.S.C. 154(b) by 0 days.

(21) Appl. No.: 16/647,721

(22) PCT Filed: Sep. 20, 2018

(86) PCT No.: PCT/IB2018/057262

§ 371 (c)(1),
(2) Date: Mar. 16, 2020

(87) PCT Pub. No.: WO2019/058304

PCT Pub. Date: Mar. 28, 2019

(65) Prior Publication Data

US 2020/0224197 A1 Jul. 16, 2020

(30) Foreign Application Priority Data

Sep. 20, 2017 (IT) ........................ 102017000105372

(51) Int. Cl.

| | |
|---|---|
| ***C07H 21/04*** | (2006.01) |
| ***C12N 15/113*** | (2010.01) |
| ***C12N 15/67*** | (2006.01) |
| *A61K 48/00* | (2006.01) |

(52) U.S. Cl.
CPC ............ *C12N 15/113* (2013.01); *C12N 15/67* (2013.01); *A61K 48/00* (2013.01); *C12N 2310/11* (2013.01); *C12N 2310/3519* (2013.01); *C12N 2840/105* (2013.01); *C12N 2840/203* (2013.01)

(58) Field of Classification Search
None
See application file for complete search history.

(56) References Cited

U.S. PATENT DOCUMENTS

2007/0136890 A1 6/2007 Allison

FOREIGN PATENT DOCUMENTS

| | | | |
|---|---|---|---|
| JP | 2006-506984 | A | 3/2006 |
| JP | 2015-535430 | A | 12/2015 |
| WO | 2004/038380 | A2 | 5/2004 |
| WO | 2012/133947 | A1 | 10/2012 |
| WO | 2014/081507 | A1 | 5/2014 |

OTHER PUBLICATIONS

Zhao, Jian, et al. ("IRESbase: a comprehensive database of experimentally validated internal ribosome entry sites." Genomics, proteomics & bioinformatics 18.2 (2020): 129-139).*
International Search Report from PCT/IB2018/057262, dated Feb. 19, 2019, 5 pages.
Written Opinion from PCT/IB2018/057262, dated Feb. 19, 2019, 7 pages.
Carrieri et al. (2012) "Long non-coding antisense RNA controls Uchl1 translation through an embedded SINEB2 repeat" Nature, vol. 491, pp. 454-457, plus two pages of methods.
Gustincich et al. (2017) "The Yin and Yang of nucleic acid-based therapy in the brain" Progress in Neurobiology, vol. 155, pp. 194-211.
Hayashi et al. (2012) "Activation of prokaryotic translation by antisense oligonucleotides binding to coding region of mRNA" Biochemical and Biophysical Research Communications, vol. 429, pp. 105-110.
Indrieri et al. (2016) "Synthetic long non-coding RNAs [SINEUPs] rescue defective gene expression in vivo" Scientific Reports, vol. 6, Article 27315, 8 pages.
Jackson (2013) "The Current Status of Vertebrate Cellular mRNA IRESs" Cold Spring Harb Perspect Biol, vol. 5, Article a011569, 20 pages.
Patrucco et al. (2015) "Engineering mammalian cell factories with SINEUP noncoding RNAs to improve translation of secreted proteins" Gene, vol. 569, pp. 287-293.
Thompson (2012) "Tricks an IRES uses to enslave ribosomes" Trends Microbiol., vol. 20, No. 11, pp. 558-566.
Weingarten-Gabbay et al. (2016) "Systematic discovery of cap-independent translation sequences in human and viral genomes" Science, vol. 351, No. 6270, aad4939, 15 pages.

(Continued)

*Primary Examiner* — Kimberly Chong
(74) *Attorney, Agent, or Firm* — ALGM, LLP; Harry J. Guttman

(57) ABSTRACT

There is disclosed a trans-acting functional nucleic acid molecule comprising a eukaryotic target binding sequence comprising a sequence reverse complementary to a target mRNA sequence for which protein translation is to be enhanced, and a regulatory sequence comprising an internal ribosome entry site (IRES) sequence or an internal ribosome entry site (IRES) derived sequence and enhancing translation of the target mRNA sequence, wherein the regulatory sequence is located 3' of the target binding sequence.

16 Claims, 27 Drawing Sheets

Specification includes a Sequence Listing.

(56) References Cited

OTHER PUBLICATIONS

Zucchelli et al. (2015) "SINEUPs: A new class of natural and synthetic antisense long non-coding RNAs that activate translation" RNA Biology, vol. 12, No. 8, pp. 771-779.
Zucchelli et al. (2015) "SINEUPs are modular antisense long non-coding RNAs that increase synthesis of target proteins in cells" Frontiers in Cellular Neuroscience, vol. 9, Article 174, 12 pages.
Zucchelli et al. (2016) "Engineering Translation in Mammalian Cell Factories to Increase Protein Yield: The Unexpected Use of Long Non-Coding SINEUP RNAs" Computational and Structural Biotechnology Journal, vol. 14, pp. 404-410.
Licursi et al. (2015) "Promotion of Viral IRES-Mediated Translation Initiation under Mild Hypothermia" PLoS ONE vol. 10, No. 5, Article e0126174 (13 pages).
"TransSINE Technologies Co., Ltd started selling SINEUP products" (2013) News & Events, DNAFORM Co., Ltd., (6 pages) Japanese and English, https://www.dnaform.jp/ja/information/20130320_1/, Last accessed: Aug. 10, 2022.
Kieft (2008) "Viral IRES RNA structures and ribosome interactions" Trends in Biochemical Sciences, vol. 33, No. 6, pp. 274-283.
King et al. (2010) "The role of IRES trans-acting factors in regulating translation initiation" Biochem. Soc Trans., vol. 38, pp. 1581-1586.

* cited by examiner

C

| Annotated Gene | Gene Name | Gene pairing region | Transcript type | Position | Genomic location | Orientation | Alignment length | % Alignment | E-value | cMyc pairing region |
|---|---|---|---|---|---|---|---|---|---|---|
| ENST00000347004 | JAG2 | 3'UTR | protein_coding | 157-297 | 14:105168528-105168668 | Reverse | 144 | 65.97 | 0.014 | IRES |
| ENST00000460865 | RAB6B | 5'UTR | protein_coding | 240-311 | 3:133895528-133895597 | Reverse | 76 | 72.37 | 0.014 | IRES |
| ENST00000433688 | C11orf95 | 1st exon | protein_coding | 120-185 | 11:63768496-63768559 | Reverse | 66 | 72.73 | 0.1 | IRES |
| ENST00000256925 | CABLES1 | 3'UTR | protein_coding | 3760-3787 | 18:23259225-23259252 | Reverse | 28 | 92.86 | 0.087 | IRES |
| ENST00000399816 | UBE2QL1 | 5'UTR | protein_coding | 184-201 | 5:6448806-6448823 | Reverse | 18 | 100 | 0.57 | BD |
| ENST00000399816 | UBE2QL1 | 3'UTR | protein_coding | 166-205 | 5:6448806-6448824 | Reverse | 40 | 85 | 0.005 | BD |
| ENST00000519361 | MYRF | internal exon (nc) | retained_intron | 1764-1785 | 11:61783950-61783971 | Reverse | 22 | 100 | 0.002 | BD |
| ENST00000564062 | ARIH1 | 1st coding exon | protein_coding | 217-235 | 15:72474861-72474879 | Reverse | 19 | 100 | 0.14 | BD |
| ENST00000575477 | PAFAH1B1 | 1st exon (nc) | processed_transcript | 87-178 | 17:2593901-2593992 | Reverse | 101 | 68.32 | 0.0002 | BD |
| ENST00000397195 | PAFAH1B1 | 3'UTR | protein_coding | 156-247 | 17:2593901-2593992 | Reverse | 101 | 68.32 | 0.0002 | BD |
| ENST00000393555 | DYRK2 | 5'UTR | protein_coding | 313-360 | 12:67649033-67649080 | Reverse | 48 | 79.17 | 0.034 | BD |
| ENST00000468291 | ZIC2 | last exon (nc) | processed_transcript | 378-455 | 13:99985415-99985492 | Reverse | 82 | 68.29 | 0.25 | BD |
| ENST00000620342 | ZIC2 | last exon | protein_coding | 1329-1407 | 13:99985415-99985492 | Reverse | 83 | 68.67 | 0.092 | BD |
| ENST00000446285 | ODC1 | 1st exon (nc) | processed_transcript | 73-114 | 2:10448196-10448237 | Reverse | 43 | 79.07 | 0.67 | BD |
| ENST00000234111 | ODC1 | 3'UTR | protein_coding | 268-309 | 2:10448196-10448237 | Reverse | 43 | 79.07 | 0.67 | BD |
| ENST00000495910 | NRF1 | 5'UTR | protein_coding | 6056-6075 | 7:31252125-31252144 | Reverse | 20 | 100 | 0.1 | BD |
| ENST00000220496 | DNAJC17 | 3'UTR | protein_coding | 1000-1020 | 15:40767866-40767886 | Reverse | 21 | 100 | 0.028 | 3'UTR |
| ENST00000309539 | OLR1 | 3'UTR | protein_coding | 1954-2063 | 12:10158700-10158809 | Reverse | 110 | 66.36 | 0.018 | 3'UTR |
| ENST00000533834 | RNPC3 | 5'UTR | protein_coding | 3260-3359 | 1:103552380-103552479 | Reverse | 106 | 66.04 | 0.018 | 3'UTR |
| ENST00000610980 | IBTK | 3'UTR | protein_coding | 4749-4819 | 6:82170615-82170685 | Reverse | 72 | 73.61 | 0.018 | 3'UTR |
| ENST00000295213 | SPATA18 | 5'UTR | protein_coding | 3644-3702 | 4:52096540-52096598 | Reverse | 60 | 78.33 | 0.018 | 3'UTR |
| ENST00000398559 | TMF1 | 5'UTR | protein_coding | 3616-3730 | 3:69022946-69023060 | Reverse | 115 | 68.7 | 0.0001 | 3'UTR |
| ENST00000238497 | VPS4B | 3'UTR | protein_coding | 1873-1999 | 18:63390519-63390641 | Reverse | 128 | 65.22 | 0.0003 | 3'UTR |
| ENST00000356126 | PSMD12 | 5'UTR | protein_coding | 2542-2626 | 17:67339696-67339780 | Reverse | 87 | 72.41 | 0.001 | 3'UTR |
| ENST00000528335 | C11orf54 | 3'UTR | protein_coding | 28-117 | 11:93746512-93746601 | Forward | 92 | 69.57 | 0.002 | 3'UTR |
| ENST00000357917 | RHOBTB1 | 3'UTR | protein_coding | 2535-2612 | 10:60871165-60871242 | Reverse | 82 | 70.73 | 0.002 | 3'UTR |
| ENST00000392519 | TMEM121 | 5'UTR | protein_coding | 620-696 | 14:105529290-105529366 | Reverse | 80 | 70 | 0.033 | CDS |
| ENST00000325468 | GYLTL1B | 3'UTR | protein_coding | 128-187 | 11:45922905-45922964 | Reverse | 60 | 76.67 | 0.053 | CDS |
| ENST00000263754 | KAT2B | 5'UTR | protein_coding | 168-282 | 3:20040239-20040354 | Reverse | 117 | 63.25 | 0.14 | CDS |
| ENST00000543491 | PCDH2 | 5'UTR | protein_coding | 404-595 | 4:30721340-30721522 | Reverse | 198 | 61.62 | 0.38 | CDS |

FIG. 23

FUNCTIONAL NUCLEIC ACID MOLECULE AND USE THEREOF

CROSS-REFERENCE TO RELATED APPLICATIONS

This application is a National Stage Entry of International Application No. PCT/IB2018/057262 filed Sep. 20, 2018, entitled "FUNCTIONAL NUCLEIC ACID MOLECULE AND USE THEREOF" which is herein incorporated by reference in its entirety, and which claims priority from Italian Patent Application No. 102017000105372 filed Sep. 20, 2017 entitled "FUNCTIONAL NUCLEIC ACID MOLECULE AND USE THEREOF" which is herein incorporated by reference in its entirety.

TECHNICAL FIELD OF THE INVENTION

The present invention relates to trans-acting functional nucleic acid molecules having the function of enhancing protein translation of specific target mRNAs in eukaryotes, to DNA molecules encoding such molecules, to uses of such molecules and to methods for enhancing protein translation.

PRIOR ART

In eukaryotes, mRNAs are primarily translated through a cap-dependent mechanism whereby initiation factors recruit the 40S ribosomal subunit to a cap structure at the 5' end of the mRNA. However, some viral and cellular messages initiate protein synthesis without a cap (Thompson S R, Trends Microbiol 2012; Jackson R J, Cold Spring Harb Perspect Biol. 2013). In these cases, a structured RNA element termed Internal Ribosome Entry Site (IRES) recruits the 40S ribosomal subunit. IRESs were discovered over 20 years ago in Picornaviruses. In cells, IRES sequences promote cap-independent translation of a subset of protein coding mRNAs to overcome the general inhibition of cap-dependent translation that occurs under stress conditions. IRES sequences are generally found in the 5' untranslated region of cellular mRNAs coding for stress-response genes, thus stimulating their translation in cis.

Recent high-throughput screening systems have expanded the list of validated IRES sequences within cellular mRNAs (Weingarten-Gabbay S, et al., Science, 2016).

Gene-specific translation up-regulation can be achieved by the modification of protein coding mRNAs to include a modified 5' sequence that contains internal ribosome entry (IRES) sequences or translation enhancer sequences. In such systems, IRES or translation enhancer sequences are placed in cis at the 5' of cDNAs encoding for the specific gene of interest. This method has been applied for the construction of vectors to express two cistrons and for enhancing translation of overexpressed genes. However, cis-regulation of translation enhancement cannot be used when the goal is to induce translation up-regulation of endogenously expressed mRNAs. There is therefore the need to identify trans-regulatory elements that promote gene-specific translation up-regulation and act on endogenous mRNAs. There is also the need for translation up-regulation trans-regulatory elements that act as independent RNA domains.

Manipulating gene expression in vivo using nucleic acid molecules has been of great interest in recent years for potential applications in clinics. Most efforts have focused so far on the ability to down-regulate toxic proteins, using siRNA, miRNA and antisense oligonucleotides. However, a large number of diseases are caused by reduced gene dosage, thus requiring an increase in protein product. While a number of studies have approached the problem at the transcriptional level, only one example exists that uses functional antisense RNA molecules (SINEUPs) to increase translation (Carrieri C., et al., Nature, 2012). SINEUPs are antisense long non-coding RNAs that are able to promote translation of partially overlapping protein-coding mRNAs with no effect on mRNA levels. SINEUP activity depends on two functional domains: the overlapping region, or "Binding Doman", dictates SINEUP specificity, while the embedded inverted SINEB2 element acts as "Effector Domain" and controls enhancement of mRNA translation (Zucchelli S., et al., Front Cell Neurosci 2015; Zucchelli S., et al, RNA Biol, 2015). By taking advantage of their modular structure, synthetic SINEUPs can be designed to specifically enhance translation of virtually any target gene of interest (Zucchelli S., et al., Front Cell Neurosci 2015; Zucchelli S., et al, RNA Biol, 2015; Indrieri A., et al., Scientific Reports, 2016; Gustincich S., et al., Prog Neurobiol, 2016; Zucchelli S., et al., Comput Struct Biotechnol J, 2016).

EP2691522 discloses functional nucleic acid molecules including SINEUPs.

Despite their potentials, SINEUPs rely on the translation enhancer activity of the embedded SINE element, a sequence derived from the mouse genome and with the potential to retrotranspose (move from one genomic location to another) in recipient cells. This would be detrimental for any therapeutical use which involves translation up-regulation for the correction of insufficient gene dosage. There is therefore a need for trans-regulatory elements that promote gene-specific translation up-regulation and act on endogenous mRNAs that are not derived from mouse sequences. There is also a need for trans-regulatory elements that promote gene-specific translation up-regulation and are not derived from transposable elements.

Most functional nucleic acid molecules of EP2691522 have rather long lengths. There is a need for the identification of shorter trans-regulatory elements that promote gene-specific translation up-regulation and act on endogenous mRNA, in order to render the delivery of the RNA molecules to the recipient cells more efficient.

The translation enhancement effect of the functional nucleic acid molecules of EP2691522 is typically 1.5-2.0 fold depending on the cell type. This level of protein increase may be insufficient if the goal is to induce translation up-regulation in human for the correction of insufficient gene dosage. There is therefore the need to identify trans-regulatory elements that promote higher levels of gene-specific translation up-regulation and act on endogenous mRNAs.

SUMMARY OF THE INVENTION

It is therefore an object of the present invention to provide a functional nucleic acid molecule that overcomes the above mentioned issues and, possibly, also has an enhanced function.

This object is achieved by means of the trans-acting functional nucleic acid molecule as defined in claim 1.

Other objects of the present invention are to provide a DNA molecule as defined in claim 10, an expression vector as defined in claim 11, a method for enhancing protein translation as defined in claim 12, a composition as defined in claim 13 and uses of the trans-acting functional nucleic acid molecule as defined in claims 14 and 15.

DEFINITIONS

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

By the term "internal ribosome entry site (IRES) derived sequence" there is intended a sequence of nucleic acid with a homology to an internal ribosome entry site (IRES) sequence such as to retain the functional activity thereof, i.e. a translation enhancing activity. In particular, the internal ribosome entry site (IRES) derived sequence can be obtained from a naturally occurring IRES sequence by genetic engineering or chemical modification, e.g. by isolating a specific sequence of the IRES sequence which remains functional, or mutating/deleting/introducing one or more nucleotides in the IRES sequence, or replacing one or more nucleotides in the IRES sequence with structurally modified nucleotides or analogs. More in particular, the skilled in the art would know that an internal ribosome entry site (IRES) derived sequence is a nucleotide sequence capable of promoting translation of a second cistron in a bicistronic construct. Typically, a dual luciferase (Firefly luciferase, Renilla Luciferase) encoding plasmid is used for experimental tests. A large-scale screening based on a dual reporter or bicistronic plasmid has been recently employed to survey sequences from the human genome for their ability to act as IRES (Weingarten-Gabbay S, et al., Science. 2016, 351:6270). A major database exists, namely IRESite, for the annotation of nucleotide sequences that have been experimentally validated as IRES, using dual reporter or bicistronic assays (http://iresite.org/IRESite_web.php). Within the IRESite, a web-based tool is available to search for sequence-based and structure-based similarities between a query sequence of interest and the entirety of annotated and experimentally validated IRES sequences within the database (http://iresite.org./IRESite_web.php?page=search). The output of the program is a probability score for any nucleotide sequence to be able to act as IRES in a validation experiment with bicistronic constructs. Additional sequence-based and structure-based web-based browsing tools are available to suggest, with a numerical predicting value, the IRES activity potentials of any given nucleotide sequence (http://rna.informatik.uni-freiburg.de/; http://regrna.mbc.nctu.edu.tw/index1.php).

DETAILED DESCRIPTION OF THE INVENTION

Figure 1:
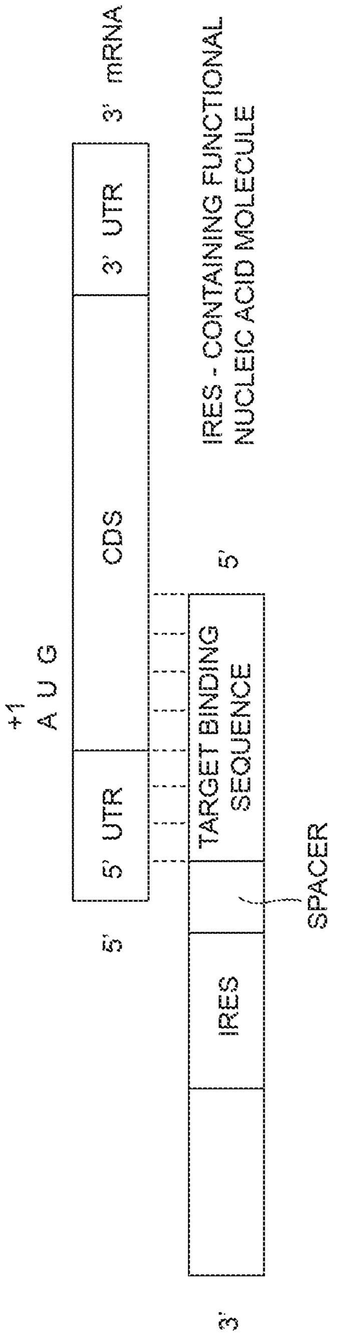
FIG. 1 shows a schematic diagram of the trans-acting functional nucleic acid molecule according to the present invention.

With reference to FIG. 1, the trans-acting functional nucleic acid molecule of the invention (also referred to in the following as "IRUP") comprises a target binding sequence (also referred to as "binding domain") and a regulatory sequence (also referred to as "effector domain").

The target binding sequence comprises a sequence reverse complementary to a eukaryotic target mRNA sequence for which protein translation is to be enhanced.

The eukaryotic target mRNA sequence is preferably an animal or human target mRNA sequence, more preferably a human target mRNA sequence.

The regulatory sequence comprises an internal ribosome entry site (IRES) sequence or an internal ribosome entry site (IRES) derived sequence and enhances translation of the target mRNA sequence.

The regulatory sequence is located 3' of the target binding sequence.

The trans-acting functional nucleic acid molecule hybridises to the target mRNA sequence through the target binding sequence and the IRES or IRES derived sequence enhances the translation of the target mRNA sequence.

The functional nucleic acid molecule of the invention allows to exploit IRES sequences as trans-regulatory elements for gene-specific increase of translation of virtually any cellular endogenous or overexpressed protein-coding mRNA.

Preferably, the target binding sequence consists, from 3' to 5', of a sequence reverse complementary to 1 to 50 nucleotides of the 5' untranslated region (5' UTR) and 1 to 40 nucleotides of the coding sequence (CDS) of the target mRNA sequence. Specific non-limiting examples include target binding sequences consisting of:

- a sequence reverse complementary to 40 nucleotides of the 5' untranslated region (5' UTR) and 4 nucleotides of the coding sequence (CDS) of the target mRNA sequence (referred to the initiation methionine codon or to internal in-frame methionine codons);
- a sequence reverse complementary to 40 nucleotides of the 5' untranslated region (5' UTR) and 32 nucleotides of the coding sequence (CDS) of the target mRNA sequence;
- a sequence reverse complementary to 14 nucleotides of the 5' untranslated region (5' UTR) and 4 nucleotides of the coding sequence (CDS) of the target mRNA sequence (referred to the initiation methionine codon).

The regulatory sequence comprises an internal ribosome entry site (IRES) sequence preferably derived from human viruses or human protein-coding genes. Several IRESs having sequences ranging from 48 to 576 nucleotides have been tested with success, e.g. human Hepatitis C Virus (HCV) IRESs (SEQ ID NO:36 and SEQ ID NO:37), human poliovirus IRESs (SEQ ID NO:38 and SEQ ID NO:39), human encephalomyocarditis (EMCV) virus (SEQ ID NO:40 and SEQ ID NO:41), human cricket paralysis (CrPV) virus (SEQ ID NO:42 and SEQ ID NO:43), human Apaf-1 (SEQ ID NO:44 and SEQ ID NO:45), human ELG-1 (SEQ ID NO:46 and SEQ ID NO:47), human c-MYC (SEQ ID NO:48, SEQ ID NO:49, SEQ ID NO: 50, and SEQ ID NO:51), human dystrophin (DMD) (SEQ ID NO:52 and SEQ ID NO:53). More detail can be found in the example section. Sequences coding for structural elements of the IRESs, fundamental for the translation enhancing activity, have been identified, isolated and used as regulatory sequences of the trans-acting functional nucleic acid molecule.

As already mentioned in the definitions, internal ribosome entry site (IRES) derived sequences can include genetically engineered or chemically modified IRESs.

Chemical modifications include, but are not limited to, the following:

Base modifications: pseudouridine; 5'-Bromo-uridine; 5'-methylcytidine.

Sugar modifications (2' modifications): 2'-O-methyl-(2'-O-Me); 2'-O-methoxyethyl (2'-MOE); locked nucleic acid (LNA).

Backbone modifications (phosphate backbone modifications): Phosphorothioate (PS); phosphotriester.

Others (cell-type specific targeting domains): GalNAc linkage (hepatocytes).

Although the IRES sequence or IRES derived sequence is functional whether inserted—in the trans-acting functional nucleic acid molecule—in direct or inverted orientation relative to the 5' to 3' orientation of the functional nucleic acid molecule, it is preferably oriented in direct orientation. In other words, by “direct” there is intended the situation in which the IRES sequence is embedded (inserted) with the same 5' to 3' orientation as the functional nucleic acid molecule. Instead, by “inverted” there is intended the situation in which a reverse complement of the IRES sequence is inserted in the nucleic acid molecule (the IRES sequence is 3' to 5' oriented relative to the functional nucleic acid molecule).

Preferably, the IRES sequence or IRES derived sequence is a sequence with 75% homology to a sequence selected from the group consisting of SEQ ID NO:36 to SEQ ID NO:65, more preferably a sequence with 90% homology to a sequence selected from the group consisting of SEQ ID NO:36 to SEQ ID NO:65, even more preferably a sequence selected from the group consisting of SEQ ID NO:36 to SEQ ID NO:65.

The trans-acting functional nucleic acid molecule is preferably an RNA molecule or a modified RNA molecule. Examples of modifications are:

Base modifications: pseudouridine; 5'-Bromo-uridine; 5'-methylcytidine.

Sugar modifications (2' modifications): 2'-O-methyl-(2'-O-Me); 2'-O-methoxyethyl (2'-MOE); locked nucleic acid (LNA).

Backbone modifications (phosphate backbone modifications): Phosphorothioate (PS); phosphotriester.

Others (cell-type specific targeting domains): GalNAc linkage (hepatocytes).

The trans-acting functional nucleic acid molecule preferably further comprises a spacer sequence between the target binding sequence and the regulatory sequence.

In addition, the trans-acting functional nucleic acid molecule optionally comprises a non-coding 3' tail sequence, which e.g. includes restriction sites useful for cloning the molecule in appropriate plasmids.

Several trans-acting functional nucleic acid molecule have been generated according to the invention.

The features of some of these molecules are summarised in the following. (BD=Binding Domain; numbering in parenthesis is with respect to AUG triplet A=+1)

SEQ ID NO:1
Definition: IRUP Functional Nucleic Acid Molecule
IRES: viral IRES, Human Hepatitis C Virus, HCV, 383 nucleotides, direct orientation
Features: BD=DJ-1s (−40/+4)
ED=IRES HCV (383 ntds) (SEQ ID NO:36)
Backbone=Delta5'ASUchl1
IRES orientation: direct SEQ ID NO: 2
Definition: IRUP Functional Nucleic Acid Molecule
IRES: viral IRES, Human Hepatitis C Virus, HCV, 383 nucleotides, inverted orientation
Features: BD=DJ-1s (−40/+4)
ED=IRES HCV (383 ntds) (SEQ ID NO:37)
Backbone=Delta5'ASUchl1
IRES orientation: inverted (reverse complement)

SEQ ID NO: 3
Definition: IRUP Functional Nucleic Acid Molecule
IRES: viral IRES, Human Polio Virus, 312 nucleotides, direct orientation
Features: BD=DJ-1s (−40/+4)
ED=IRES poliovirus (312 ntds) (SEQ ID NO:38)
Backbone=Delta5'ASUchl1
IRES orientation: direct SEQ ID NO: 4
Definition: IRUP Functional Nucleic Acid Molecule
IRES: viral IRES, Human Polio Virus, 312 nucleotides, inverted orientation
Features: BD=DJ-1s (−40/+4)
ED=IRES poliovirus (312 ntds) (SEQ ID NO:39)
Backbone=Delta5'ASUchl1
IRES orientation: inverted (reverse complement)

SEQ ID NO: 5
Definition: IRUP Functional Nucleic Acid Molecule
IRES: viral IRES, Human Encephalomyocarditis virus, EMCV-R, 576 nucleotides, direct orientation
Features: BD=DJ-1s (−40/+4)
ED=IRES EMCV-R (576 ntds) (SEQ ID NO:40)
Backbone=Delta5'ASUchl1
IRES orientation: direct SEQ ID NO: 6
Definition: IRUP Functional Nucleic Acid Molecule
IRES: viral IRES, Human Encephalomyocarditis virus, EMCV-R, 576 nucleotides, inverted orientation
Features: BD=DJ-1s (−40/+4)
ED=IRES EMCV-R (576 ntds) (SEQ ID NO:41)
Backbone=Delta5'ASUchl1
IRES orientation: inverted (reverse complement)

SEQ ID NO: 7
Definition: IRUP Functional Nucleic Acid Molecule
IRES: viral IRES, Human Cricket Paralysis Virus, CrPV, 192 nucleotides, direct orientation
Features: BD=DJ-1s (−40/+4)
ED=IRES CrPV (192 ntds) (SEQ ID NO:42)
Backbone=Delta5'ASUchl1
IRES orientation: direct SEQ ID NO: 8
Definition: IRUP Functional Nucleic Acid Molecule
IRES: viral IRES, Human Cricket Paralysis Virus, CrPV, 192 nucleotides, inverted orientation
Features: BD=DJ-1s (−40/+4)
ED=IRES CrPV (192 ntds) (SEQ ID NO:43)
Backbone=Delta5'ASUchl1
IRES orientation: inverted (reverse complement)

SEQ ID NO: 9
Definition: IRUP Functional Nucleic Acid Molecule
IRES: cellular IRES, Human Apaf-1, 231 nucleotides, direct orientation
(Ensembl: ENSG00000120868; MIM:602233)
Features: BD=DJ-1s (−40/+4)
ED=IRES Apaf-1 (231 ntds) (SEQ ID NO:44)
Backbone=Delta5'ASUchl1

IRES orientation: direct
SEQ ID NO: 10
Definition: IRUP Functional Nucleic Acid Molecule
IRES: cellular IRES, Human Apaf-1, 231 nucleotides, inverted orientation
(Ensembl: ENSG00000120868; MIM:602233)
Features: BD=DJ-1s (−40/+4)
ED=IRES Apaf-1 (231 ntds) (SEQ ID NO:45)
Backbone=Delta5'ASUchl1
IRES orientation: inverted (reverse complement)
SEQ ID NO: 11
Definition: IRUP Functional Nucleic Acid Molecule
IRES: cellular IRES, Human ELG-1, 460 nucleotides, direct orientation
(Ensembl: ENSG00000176208; MIM:609534)
Features: BD=DJ-1s (−40/+4)
ED=IRES ELG-1 (460 ntds) (SEQ ID NO:46)
Backbone=Delta5'ASUchl1
IRES orientation: direct
SEQ ID No: 12
Definition: IRUP Functional Nucleic Acid Molecule
IRES: cellular IRES, Human ELG-1, 460 nucleotides, inverted orientation
(Ensembl: ENSG00000176208; MIM:609534)
Features: BD=DJ-1s (−40/+4)
ED=IRES ELG-1 (460 ntds) (SEQ ID NO:47)
Backbone=Delta5'ASUchl1
IRES orientation: inverted (reverse complement)
SEQ ID NO: 13
Definition: IRUP Functional Nucleic Acid Molecule
IRES: cellular IRES, Human c-MYC, 395 nucleotides, direct orientation
(Ensembl: ENSG00000136997; MIM:190080)
Features: BD=DJ-1s (−40/+4)
ED=IRES c-MYC full-length (395 ntds) (SEQ ID NO:48)
Backbone=Delta5'ASUchl1
IRES orientation: direct
Others: includes the 48 nt minimal sequence (SEQ ID NO:50) included in SEQ ID NO:15.
SEQ ID NO: 14
Definition: IRUP Functional Nucleic Acid Molecule
IRES: cellular IRES, Human c-MYC, 395 nucleotides, inverted orientation
(Ensembl: ENSG00000136997; MIM:190080)
Features: BD=DJ-1s (−40/+4)
ED=IRES c-MYC full-length (395 ntds) (SEQ ID NO:49)
Backbone=Delta5'ASUchl1
IRES orientation: inverted (reverse complement)
Others: includes the 48nt minimal sequence (SEQ ID NO:51) included in SEQ ID NO:16.
SEQ ID NO: 15
Definition: IRUP Functional Nucleic Acid Molecule
IRES: cellular IRES, Human c-MYC, 48 nucleotides, direct orientation
(Ensembl: ENSG00000136997; MIM:190080)
Features: BD=DJ-1s (−40/+4)
ED=IRES c-MYC (48 ntds) (SEQ ID NO:50)
Backbone=Delta5'ASUchl1
IRES orientation: direct
SEQ ID NO: 16
Definition: IRUP Functional Nucleic Acid Molecule
IRES: cellular IRES, Human c-MYC, 48 nucleotides, inverted orientation
(Ensembl: ENSG00000136997; MIM:190080)
Features: BD=DJ-1s (−40/+4)
ED=IRES c-MYC (48 ntds) (SEQ ID NO:51)
Backbone=Delta5'ASUchl1
IRES orientation: inverted (reverse complement)
SEQ ID NO: 17
Definition: IRUP Functional Nucleic Acid Molecule
IRES: cellular IRES, Human dystrophin (DMD), 71 nucleotides, direct orientation
(Ensembl: ENSG00000198947; MIM:300377)
Features: BD=DJ-1s (−40/+4)
ED=IRES DMD (71 ntds) (SEQ ID NO:52)
Backbone=Delta5'ASUchl1
IRES orientation: direct
SEQ ID NO: 18
Definition: IRUP Functional Nucleic Acid Molecule
IRES: cellular IRES, Human dystrophin (DMD), 71 nucleotides, inverted orientation
(Ensembl: ENSG00000198947; MIM:300377)
Features: BD=DJ-1s (−40/+4)
ED=IRES DMD (71 ntds) (SEQ ID NO:53)
Backbone=Delta5'ASUchl1
IRES orientation: inverted (reverse complement)
SEQ ID NO: 19
Definition: IRUP Functional Nucleic Acid Molecule
IRES: viral IRES, Human Hepatitis C Virus, HCV mutant #1, 303 nucleotides, delta II (40-119), interaction with ribosomal proteins
Features: BD=DJ-1s (−40/+4)
ED=HCV IRES direct, deltaII (SEQ ID NO:54)
Backbone=Delta5'ASUchl1
Mutant #1: delta II (40-119), interaction with ribosomal proteins
SEQ ID NO: 20
Definition: IRUP Functional Nucleic Acid Molecule
IRES: viral IRES, Human Hepatitis C Virus, HCV mutant #2, 367 nucleotides, delta IIIa (156-171), eIF3 binding site
Features: BD=DJ-1s (−40/+4)
ED=HCV IRES direct, deltaIIIa (SEQ ID NO:55)
Backbone=Delta5'ASUchl1
Mutant #2: delta IIIa (156-171), eIF3 binding site
SEQ ID NO: 21
Definition: IRUP Functional Nucleic Acid Molecule
IRES: viral IRES, Human Hepatitis C Virus, HCV mutant #3, 356 nucleotides, delta IIId (253-279), 18S rRNA binding region
Features: BD=DJ-1s (−40/+4)
ED=HCV IRES direct, deltaIIId (SEQ ID NO:56)
Backbone=Delta5'ASUchl1
Mutant #3: delta IIId (253-279), 18S rRNA binding region
SEQ ID NO: 22
Definition: IRUP Functional Nucleic Acid Molecule
IRES: viral IRES, Human Hepatitis C Virus, HCV mutant #4, 330 nucleotides, delta IV (331-383), AUG-containing terminal sequence
Features: BD=DJ-1s (−40/+4)
ED=HCV IRES direct, deltaIV (SEQ ID NO:57)
Backbone=Delta5'ASUchl1
Mutant #4: delta IV (331-383), AUG-containing terminal sequence
SEQ ID NO: 23
Definition: IRUP Functional Nucleic Acid Molecule
IRES: viral IRES, Human Hepatitis C Virus, HCV mutant #5, 383 nucleotides, G266→C; single point mutation, contact with 18S rRNA
Features: BD=DJ-1s (−40/+4)
ED=HCV IRES direct, G266→C (SEQ ID NO:58)
Backbone=Delta5'ASUchl1
Mutant #5: G266→C; single point mutation, contact with 18S rRNA
SEQ ID NO: 24

Definition: IRUP Functional Nucleic Acid Molecule
IRES: viral IRES, Human Hepatitis C Virus, HCV mutant #6, 383 nucleotides, U228→C; control single point mutation in another site of HCV IRES, decreases IRES activity without disrupting formation of pre-initiation complex
Features: BD=DJ-1s (−40/+4)
ED=HCV IRES direct, U228→C (SEQ ID NO:59)
Backbone=Delta5'ASUchl1
Mutant #6: U228→C; control single point mutation in another site of HCV IRES, decreases IRES activity without disrupting formation of pre-initiation complex. Mutated version has reduced affinity for eIF3.
SEQ ID NO: 25
Definition: IRUP Functional Nucleic Acid Molecule
IRES: viral IRES, Human Hepatitis C Virus, HCV mutant #7, 383 nucleotides, G267→C; IIId loop, single point mutation, contact with 18S rRNA
Features: BD=DJ-1s (−40/+4)
ED=HCV IRES direct, G267→C (SEQ ID NO:60)
Backbone=Delta5'ASUchl1
Mutant #7: G267→C; IIId loop, single point mutation, contact with 18S rRNA
SEQ ID NO: 26
Definition: IRUP Functional Nucleic Acid Molecule
IRES: viral IRES, Human Hepatitis C Virus, HCV mutant #8, 383
nucleotides, G268→C; IIId loop, single point mutation, contact with 18S rRNA
Features: BD=DJ-1s (−40/+4)
ED=HCV IRES direct, G268→C (SEQ ID NO:61)
Backbone=Delta5'ASUchl1
Mutant #8: G268→C; IIId loop, single point mutation, contact with 18S rRNA
SEQ ID NO: 27
Definition: IRUP Functional Nucleic Acid Molecule
IRES: viral IRES, Human Hepatitis C Virus, HCV mutant #9, 383 nucleotides, $G_{266}G_{267}G_{268}$→$C_{266}C_{267}C_{268}$; IIId loop, triple point mutation, contact with 18S rRNA
Features: BD=DJ-1s (−40/+4)
ED=HCV IRES direct, $G_{266}G_{267}G_{268}$→$C_{266}C_{267}C_{268}$ (SEQ ID NO:62)
Backbone=Delta5'ASUchl1
Mutant #9: $G_{266}G_{267}G_{268}$→$C_{266}C_{267}C_{268}$; IIId loop, triple point mutation, contact with 18S rRNA
SEQ ID NO: 28
Definition: IRUP Functional Nucleic Acid Molecule
IRES: viral IRES, Human Hepatitis C Virus, HCV mutant #10, 383 nucleotides, G266→A/G268→T; double point mutant; HCV 5a isolate with poor infectivity
Features: BD=DJ-1s (−40/+4)
ED=HCV IRES direct, G266→A/G268→T (SEQ ID NO:63)
Backbone=Delta5'ASUchl1
Mutant #10: G266→A/G268→T; double point mutant; HCV 5a isolate with poor infectivity
SEQ ID NO: 29
Definition: IRUP Functional Nucleic Acid Molecule
IRES: viral IRES, Human Hepatitis C Virus, HCV mutant #11, 383 nucleotides, IIIa→IIIa-comp; AGTA→TCAT
Features: BD=DJ-1s (−40/+4)
ED=HCV IRES direct, IIIa→IIIa-comp; AGTA→TCAT (SEQ ID NO:64)
Backbone=Delta5'ASUchl1
Mutant #11: HCV IRES direct, IIIa→IIIa-comp; AGTA→TCAT)
SEQ ID NO: 30
Definition: IRUP Functional Nucleic Acid Molecule
IRES: viral IRES, Human Hepatitis C Virus, HCV mutant #12, 383 nucleotides, IIe→IIIe-comp; TGATAG→ACTATC
Features: BD=DJ-1s (−40/+4)
ED=HCV IRES direct, IIIe→IIIe-comp; TGATAG→ACTATC (SEQ ID NO:65)
Backbone=Delta5'ASUchl1
Mutant #12: HCV IRES direct, IIIe→IIIe-comp; TGATAG→ACTATC
SEQ ID NO: 31
Definition: miniIRUP Functional Nucleic Acid Molecule
IRES: viral IRES, Human Hepatitis C Virus, HCV, 383 nucleotides, direct orientation
Features: BD=DJ-1s (−40/+4)
ED=IRES HCV (383 ntds) (SEQ ID NO:36)
IRES orientation: direct
SEQ ID NO: 32
Definition: miniIRUP Functional Nucleic Acid Molecule
IRES: viral IRES, Human Polio Virus, 312 nucleotides, direct orientation
Features: BD=DJ-1s (−40/+4)
ED=IRES poliovirus (312 ntds) (SEQ ID NO:38)
IRES orientation: direct
SEQ ID NO: 33
Definition: miniIRUP Functional Nucleic Acid Molecule
IRES: viral IRES, Human Polio Virus, 312 nucleotides, inverted orientation
Features: BD=DJ-1s (−40/+4)
ED=IRES poliovirus (312 ntds) (SEQ ID NO:39)
IRES orientation: inverted (reverse complement)
SEQ ID NO: 34
Definition: miniIRUP Functional Nucleic Acid Molecule
IRES: cellular IRES, Human c-MYC, 48 nucleotides, direct orientation) (Ensembl: ENSG00000136997; MIM:190080)
Features: BD=DJ-1s (−40/+4)
ED=IRES c-MYC (48 ntds) (SEQ ID NO:50)
IRES orientation: direct
SEQ ID NO: 35
Definition: miniIRUP Functional Nucleic Acid Molecule
IRES: viral IRES, Human Hepatitis C Virus, HCV, 383 nucleotides, direct orientation
Features: BD=GFP (−40/+32)
ED=IRES HCV (383 ntds) (SEQ ID NO:36)
IRES orientation: direct A DNA molecule according to the present invention encodes any of the above disclosed trans-acting functional nucleic acid molecules.

An expression vector according to the present invention comprises the above said DNA molecule. In particular, the following plasmids have been used for efficient expression of functional nucleic acid molecules.

Mammalian Expression Plasmids:
Plasmid Name: pCS2+
Expression: CMVie92 promoter
SV40polyA terminator
Plasmid Name: pCDN3.1 (−)
Expression: CMV promoter
BGH terminator
Plasmid Name: pDUAL-eGFPΔ (modified from peGFP-C1)
Expression: H1 promoter; CMV promoter
BGH terminator; SV40 terminator
Viral Vectors:
Vector Name: pAAV
Virus: Adeno-Associated Virus
Expression: CAG promoter/CMV enhancer
SV40polyA terminator
Vector Name: pLVX-TetOne-Puro
Virus: Lentivirus Expression: TRE3G promoter (inducible expression)

SV40polyA terminator

It should be noted that the experiments carried out have highlighted that the function of the trans-acting functional nucleic acid molecule is not influenced by the plasmid used.

A method for enhancing protein translation according to the invention comprises transfecting into a cell the above disclosed trans-acting functional nucleic acid molecule or DNA molecule or expression vector.

A composition according to the present invention comprises the above disclosed trans-acting functional nucleic acid molecule or DNA molecule or expression vector. The trans-acting functional nucleic acid molecule can be delivered as naked RNA, the RNA optionally including modifications adapted to increase RNA stability. As an alternative the trans-acting functional nucleic acid molecule can be an in vitro transcribed RNA encapsulated in an array of lipid-based nanoparticles or an in vitro transcribed RNA encapsulated in exosome-based particles.

The above disclosed trans-acting functional nucleic acid molecule or DNA molecule or expression vector can be used for enhancing translation of a target mRNA sequence. The examples show enhancement of translation of two different target mRNA sequences, PARK7/DJ-1 (also referred to as DJ-1) and GFP, but any other mRNA sequence could be targeted with success without influencing mRNA levels.

It should be noted that IRUPs can enhance translation of the gene of interest with no effects on its own mRNA quantities.

The above disclosed trans-acting functional nucleic acid molecule or DNA molecule or expression vector can therefore be successfully used as molecular tools to validate gene function in cells as well as to implement the pipelines of recombinant protein production.

The above disclosed trans-acting functional nucleic acid molecule or DNA molecule or expression vector can be used for treating a genetic disease caused by down-regulation of a protein-coding mRNA or a sporadic disease where reduced levels of a certain protein-coding mRNA is detrimental. The following are examples of such diseases. Haploinsufficiency is a condition that arises when the normal phenotype requires the protein product of both alleles, and reduction to 50% or less of gene function results in an abnormal phenotype. This is the cause of a wide spectrum of diseases including specific types of cancers, ataxias and those due to failures of developmental programs. A large number of Rare Diseases are caused by mutations or microdeletions that lead to reduced gene dosage. Transcription factors, synaptic proteins and chromatin remodeling enzymes seem to be particularly sensitive to gene dosage. Reduced gene expression can be also observed during aging.

EXAMPLES

Example 1

Figure 2:
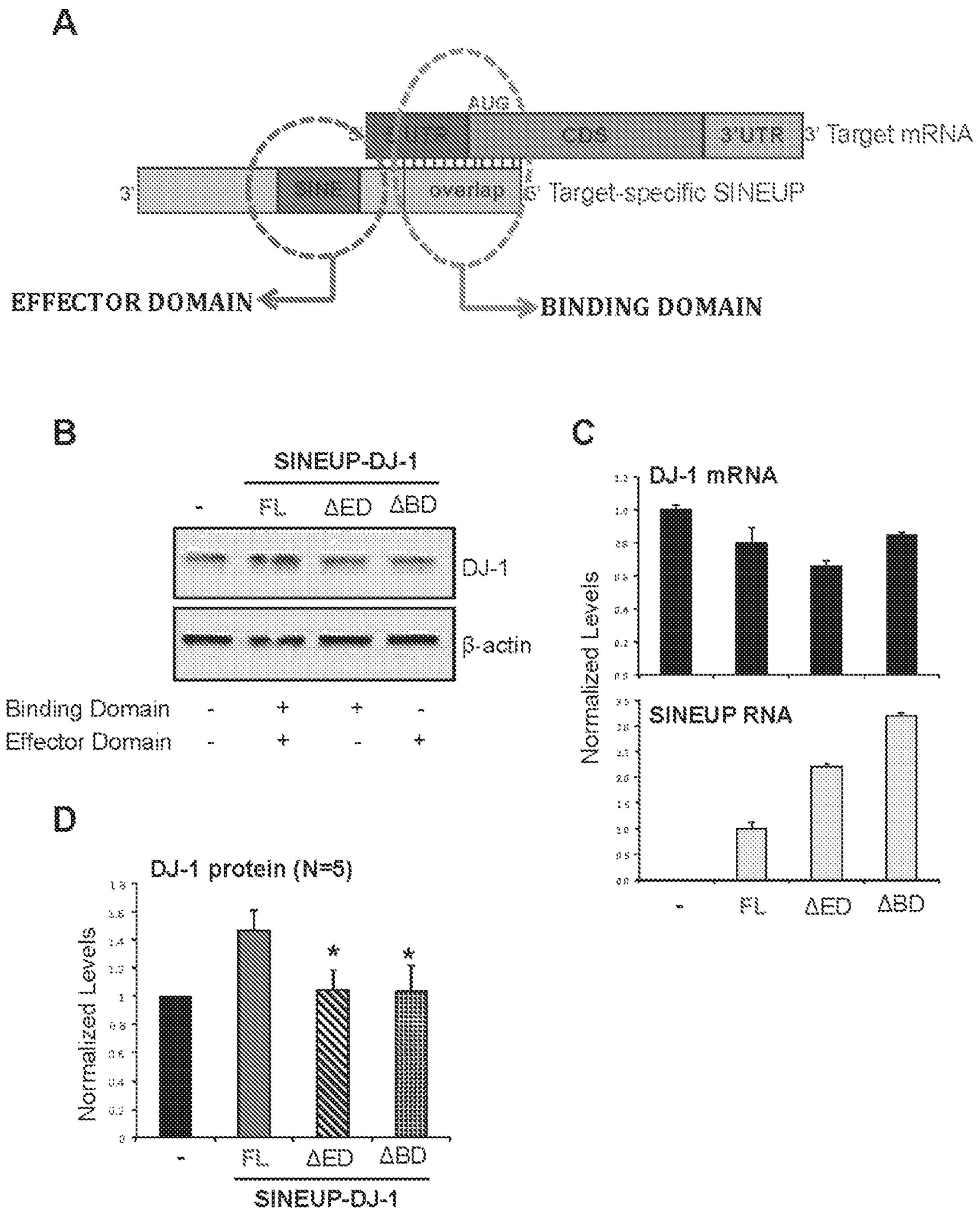
FIG. 2A shows a schematic diagram of a functional nucleic acid molecule according to the prior art (SINEUP).
FIG. 2B shows the results of a Western blot carried out on lysates of human embryonic kidney 293T/17 cells (hereinafter also referred to as HEK 293T/17 cells) transfected respectively with empty control plasmid (–), full-length SINEUP-DJ-1 (FL) and its deletion mutants (ΔED=mutant with deleted effector domain, ΔBD=mutant with deleted binding domain).
FIG. 2C shows the results of a qRT-PCR to quantify expression of endogenous DJ-1 mRNA (top panel) and SINEUP RNA (bottom panel) carried out on samples as in FIG. 2B.
FIG. 2D shows a graphical representation of full-length SINEUP-DJ-1, ΔED and ΔBD translation enhancement activity on endogenous DJ-1 mRNA in HEK 293T/17 cells (N=5). $p<0.05$

FIG. 2 shows that the embedded Effector Domain (ED) is required for translation up-regulation function of an antisense long non-coding RNA (lncRNA) targeting endogenous human DJ-1 mRNA.

FIG. 2A shows a schematic diagram of a functional antisense lncRNA molecule that up-regulates translation of target-specific mRNAs. The original molecule that uses an embedded murine transposable element of the SINE B2 family is indicated (SINEUP). SINEUP functional domains are highlighted: SINEUP Binding Domain (BD): SINEUP sequence that overlaps, in antisense orientation, to the sense protein-coding mRNA; SINEUP Effector Domain (ED): the inverted SINEB2 element (SINE) in the non-overlapping portion of SINEUPs, that confers activation of protein synthesis. 5' to 3' orientation of sense and antisense RNA molecules is indicated. Target-specific mRNA includes 5' untranslated region (5'UTR), coding sequence (CDS) and 3' untranslated region (3'UTR). Translation initiating AUG codon is also shown.

A synthetic SINEUP was designed to target endogenous human DJ-1 mRNA (SINEUP-DJ-1). SINEUP-DJ-1 mutants were generated lacking the Binding Domain (ΔBD) or the Effector Domain (ΔED). Human embryonic kidney (HEK) 293T/17 cells were transfected with plasmids encoding for SINEUP-DJ-1 full length (FL) or its deletion mutants (ΔED=mutant with deleted effector domain, ΔBD=mutant with deleted binding domain). Control cells were transfected with an empty control plasmid (−). 48 hours after transfection, cells were lysed and processed for protein quantities. Western blot (FIG. 2B) was performed with anti-DJ-1 antibody. β-actin was used as loading control. Fold-induction was calculated on Western blot images normalized to β-actin and relative to empty control samples.

RNA was purified from transfected cells. Expression of endogenous DJ-1 mRNA and SINEUP RNA was monitored by qRT-PCR using specific primers (FIG. 2C). Data indicate mean±st. dev. Data are representative of N=5 independent replicas.

FIG. 2D shows a graphical representation of SINEUP-DJ-1 FL, ΔBD and ΔED translation enhancement activity on endogenous DJ-1 mRNA in HEK 293T/17 cells (N=5). $p<0.05$

Example 2

Figure 3:
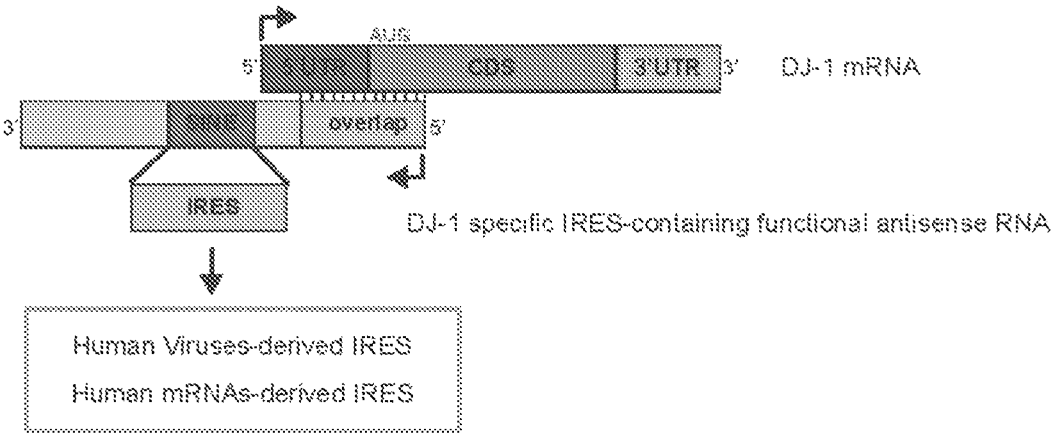
FIG. 3 shows a schematic diagram of a generic trans-acting functional nucleic acid molecule according to the present invention (IRUP) targeting DJ-1 mRNA.

Synthetic IRUPs were designed as follows to target endogenous human DJ-1 mRNA. As shows in FIG. 3, IRES-containing functional nucleic acid molecules were generated by swapping the original SINE B2 sequence with IRES sequences derived from human viruses or human mRNAs having IRES activity.

Table 1 includes the list of some of the IRES sequences used in the trans-acting functional nucleic acid molecule according to the present invention.

IRES name, IRES origin, cloning orientation and IRES length are indicated.

TABLE 1

| IRES | Origin | Orientation | Length (nt) |
|---|---|---|---|
| HCV | Human Virus | Direct | 383 |
| HCV | Human Virus | Inverted | 383 |
| Polio | Human Virus | Direct | 312 |
| Polio | Human Virus | Inverted | 312 |
| EMCV | Human Virus | Direct | 576 |
| EMCV | Human Virus | Inverted | 576 |
| CrPV | Human Virus | Direct | 192 |
| CrPV | Human Virus | Inverted | 192 |
| Apaf-1 | Human mRNA | Direct | 231 |
| Apaf-1 | Human mRNA | Inverted | 231 |
| ELG-1 | Human mRNA | Direct | 460 |
| ELG-1 | Human mRNA | Inverted | 460 |
| cMYC (long) | Human mRNA | Direct | 395 |
| cMYC (long) | Human mRNA | Inverted | 395 |
| cMYC (short) | Human mRNA | Direct | 48 |
| cMYC (short) | Human mRNA | Inverted | 48 |
| DMD | Human mRNA | Direct | 71 |
| DMD | Human mRNA | Inverted | 71 |

Figure 4:
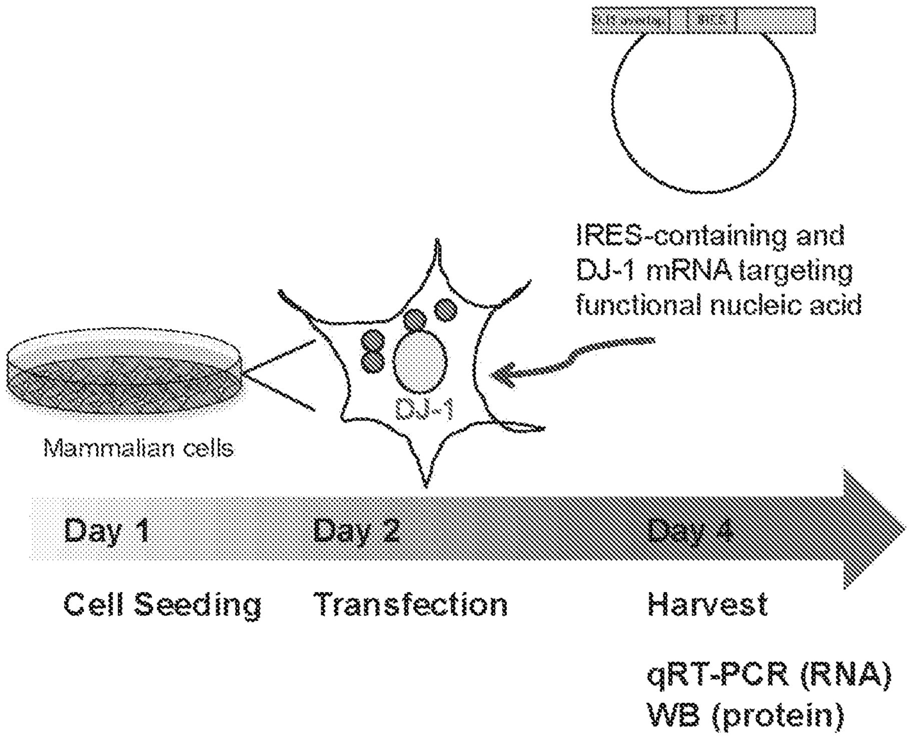
FIG. 4 shows a schematic diagram of the experimental procedure for testing translation up-regulation activity of IRES-containing functional antisense nucleic acid molecules.

FIG. 4 shows a schematic diagram of the experimental procedure for testing translation up-regulation activity of IRES-containing functional antisense nucleic acid molecules. Antisense functional nucleic acid molecules for translation activation were generated with human DJ-1 overlapping sequence (Binding Domain) and IRES sequences (Effector Domain). IRES-containing functional nucleic acid molecules were cloned into mammalian expression vectors for expression in mammalian cells in culture in vitro. Cells that express endogenous quantities of human DJ-1 mRNA were used. Timing for cell seeding, cell transfection and harvesting are shown. Cells were harvested to purify RNA (for quantitative real-time PCR, qRT-PCR) and proteins (for Western blot, WB).

Figure 5:
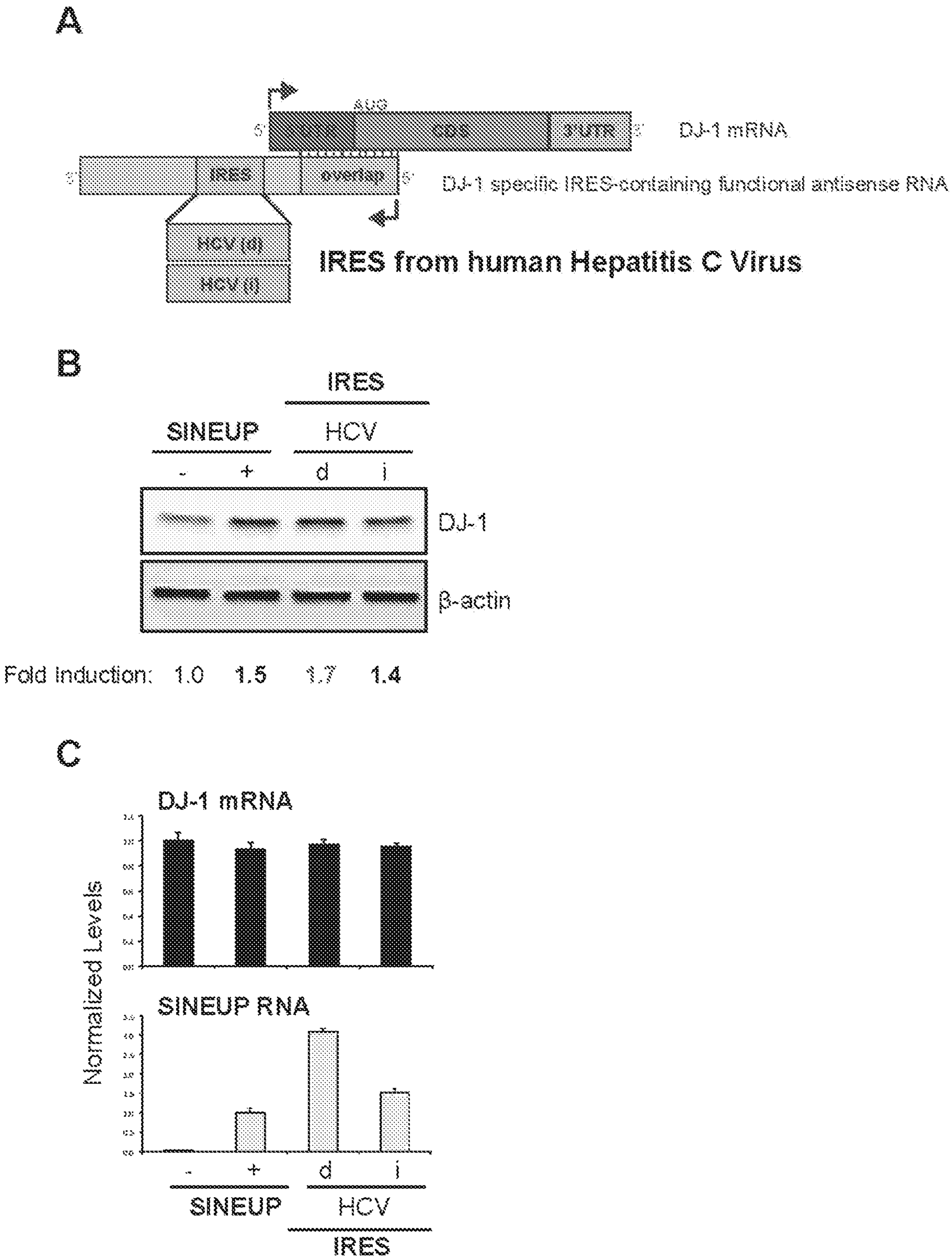
FIG. 5A shows a schematic diagram of a functional nucleic acid molecule according to the present invention (IRUP) targeting the DJ-1 gene and including an HCV IRES.
FIG. 5B shows the results of a Western blot carried out on lysates of HEK 293T/17 cells transfected respectively with empty control plasmid, SINEUP-DJ-1, and an IRUP including an HCV IRES in direct (HCV(d)) and inverted orientation (HCV(i)).
FIG. 5C shows the results of a qRT-PCR to quantify expression of endogenous DJ-1 mRNA (top panel) and IRUP RNA (bottom panel) carried out on samples as in FIG. 5B.

FIG. 5A shows a schematic diagram of a trans-acting functional nucleic acid molecule in which the effector domain is an IRES sequence from human Hepatitis C virus (HCV). IRES-containing functional nucleic acid molecules were generated with the HCV IRES sequence cloned in direct (HCV(d)—SEQ ID NO:1) or inverted (HCV(i)—SEQ ID NO:2) orientation relative to the 5' to 3' orientation of the functional nucleic acid molecule.

HEK 293T/17 cells were transfected with plasmids encoding for IRES-containing functional nucleic acid molecules with HCV IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 5B) was performed with anti-DJ-1 antibody. β-actin was used as loading control. Fold-induction was calculated on Western blot images normalized to β-actin and relative to empty control samples. Potency of IRES-containing functional nucleic acid molecules was higher or similar with respect to SINE-containing functional nucleic acid molecules.

RNA was purified from transfected cells. Expression of endogenous DJ-1 mRNA and IRUP RNA was monitored by qRT-PCR using specific primers (FIG. 5C). To compare RNA quantities across SINE- and IRES-containing functional nucleic acid molecules, primers were positioned at the 3' end of the Effector Domain. Data indicate mean±st. dev. Data are representative of N>5 independent replicas.

Example 3

Figure 6:
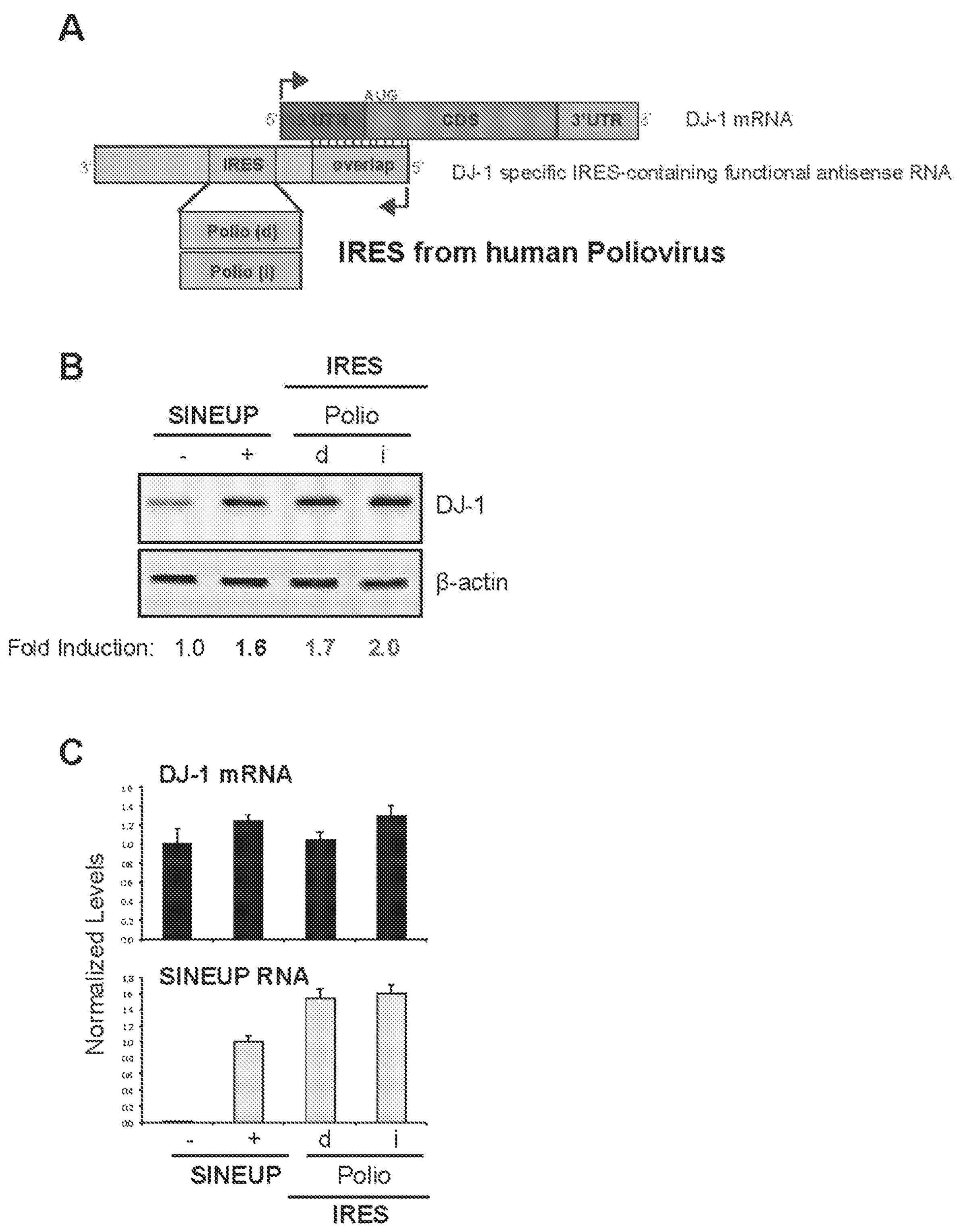
FIG. 6A shows a schematic diagram of a functional nucleic acid molecule according to the present invention (IRUP) targeting the DJ-1 gene and including a Poliovirus IRES.
FIG. 6B shows the results of a Western blot carried out on lysates of HEK 293T/17 cells transfected respectively with empty control plasmid, SINEUP-DJ-1, and an IRUP including a Poliovirus IRES in direct (Polio (d)) and inverted orientation (Polio(i)).
FIG. 6C shows the results of a qRT-PCR to quantify expression of endogenous DJ-1 mRNA (top panel) and IRUP RNA (bottom panel) carried out on samples as in FIG. 6B.

FIG. 6A shows a schematic diagram of a trans-acting functional nucleic acid molecule in which the effector domain is an IRES sequence from human Poliovirus. IRES-containing functional nucleic acid molecules were generated with the Polio IRES sequence cloned in direct (Polio(d)—SEQ ID NO:3) or inverted (Polio(i)—SEQ ID NO:4) orientation relative to the 5' to 3' orientation of the functional nucleic acid molecule.

HEK 293T/17 cells were transfected with plasmids encoding for IRES-containing functional nucleic acid molecules with Polio IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 6B) was performed with anti-DJ-1 antibody. β-actin was used as loading control. Fold-induction was calculated on Western blot images normalized to β-actin and relative to empty control samples. Potency of IRES-containing functional nucleic acid molecules was higher than SINE-containing functional nucleic acid molecules.

RNA was purified from transfected cells. Expression of endogenous DJ-1 mRNA and IRUP RNA was monitored by qRT-PCR using specific primers (FIG. 6C). To compare RNA quantities across SINE- and IRES-containing functional nucleic acid molecules, primers were positioned at the 3' end of the Effector Domain. Data indicate mean±st. dev. Data are representative of N>5 independent replicas.

Example 4

Figure 7:
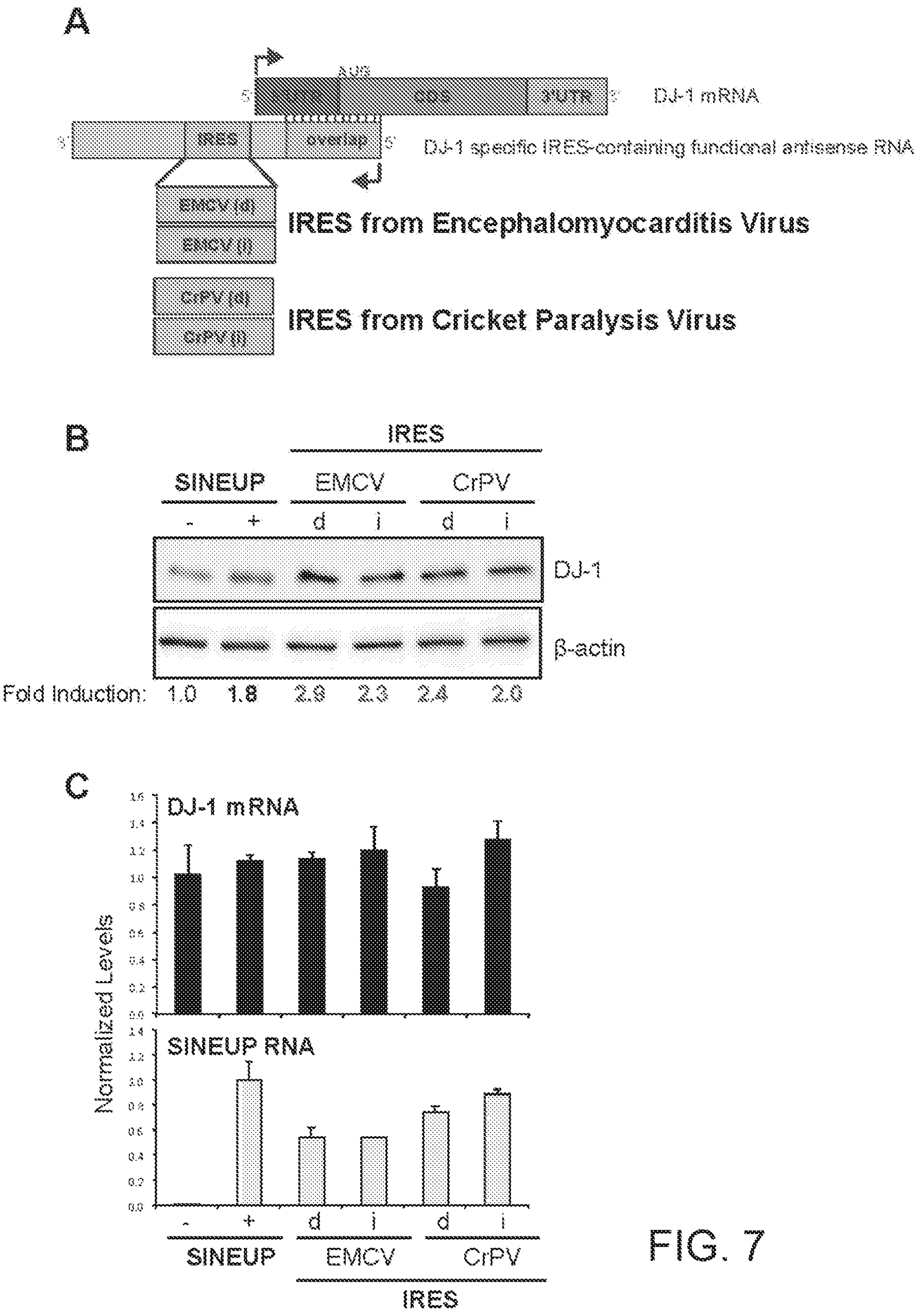
FIG. 7A shows a schematic diagram of a functional nucleic acid molecule according to the present invention (IRUP) targeting the DJ-1 gene and including an encephalomyocarditis virus (EMCV) IRES and a cricket paralysis virus (CrPV) IRES.
FIG. 7B shows the results of a Western blot carried out on lysates of HEK 293T/17 cells transfected respectively with empty control plasmid, SINEUP-DJ-1, and an IRUP including an EMCV IRES in direct (EMCV(d)) and inverted orientation (EMCV(i)), and a CrPV IRES in direct (CrPV (d)) and inverted orientation (CrPV(i)).
FIG. 7C shows the results of a qRT-PCR to quantify expression of endogenous DJ-1 mRNA (top panel) and IRUP RNA (bottom panel) carried out on samples as in FIG. 7B.

FIG. 7A shows a schematic diagram of a trans-acting functional nucleic acid molecules in which the effector domain is respectively an IRES sequence from human Encephalomyocarditis virus (EMCV) and an IRES sequence from Cricket Paralysis virus (CrPV). IRES-containing functional nucleic acid molecules were generated with the EMCV IRES sequence cloned in direct (EMCV(d)—SEQ ID NO:5) or inverted (EMCV(i)—SEQ ID NO:6) orientation relative to the 5' to 3' orientation of the functional nucleic acid molecule and with the CrPV IRES sequence cloned in direct (CrPV(d)—SEQ ID NO:7) or inverted (CrPV(i)—SEQ ID NO:8) orientation relative to the 5' to 3' orientation of the functional nucleic acid molecule.

HEK 293T/17 cells were transfected with plasmids encoding for IRES-containing functional nucleic acid molecules with EMCV and CrPV IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 7B) was performed with anti-DJ-1 antibody. β-actin was used as loading control. Fold-induction was calculated on Western blot images normalized to β-actin and relative to empty control samples. Potency of IRES-containing functional nucleic acid molecules was higher than SINE-containing functional nucleic acid molecules.

RNA was purified from transfected cells. Expression of endogenous DJ-1 mRNA and IRUP RNA was monitored by qRT-PCR using specific primers (FIG. 7C). To compare RNA quantities across SINE- and IRES-containing functional nucleic acid molecules, primers were positioned at the 3' end of the Effector Domain. Data indicate mean±st. dev. Data are representative of N>5 independent replicas.

Example 5

The increase in quantities of endogenous DJ-1 protein in HEK 293T/17 cells transfected with HCV(d) and HCV(i) IRUPs of example 2, Polio(d) and Polio(i) IRUPs of example 3 and EMCV(d), EMCV(i), CrPV(d) and CrPV(i) IRUPs of example 4 relative to empty vector transfected HEK 293T/17 cells was measured by Western blot.

Figure 8:
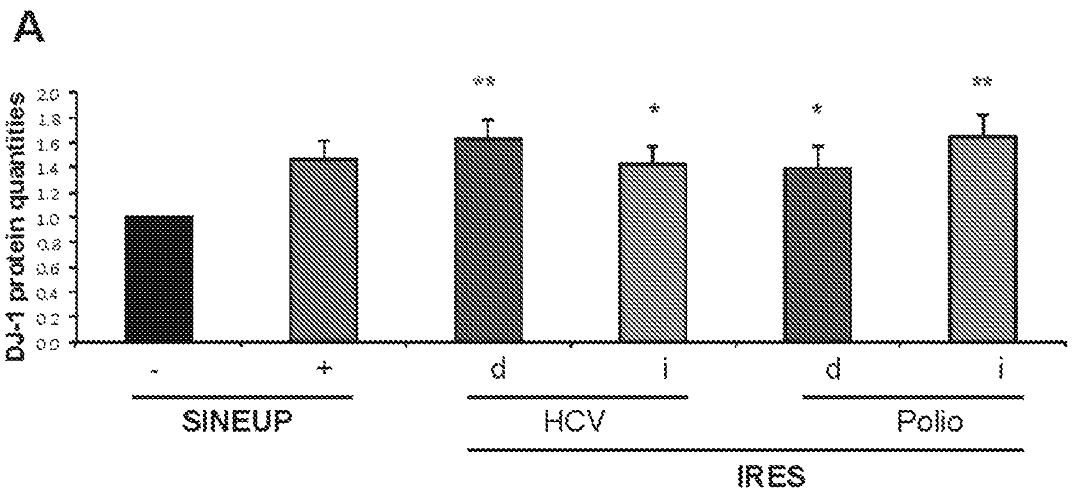
FIGS. 8A and 8B show graphs summarising the increase in quantities of DJ-1 protein in HEK 293T/17 cells transfected with HCV(d) and HCV(i) IRUPs, Polio(d) and Polio (i) IRUPs and EMCV(d), EMCV(i), CrPV(d) and CrPV(i) IRUPs of the present invention relative to empty vector transfected 293T/17 cells.
Figure 8:
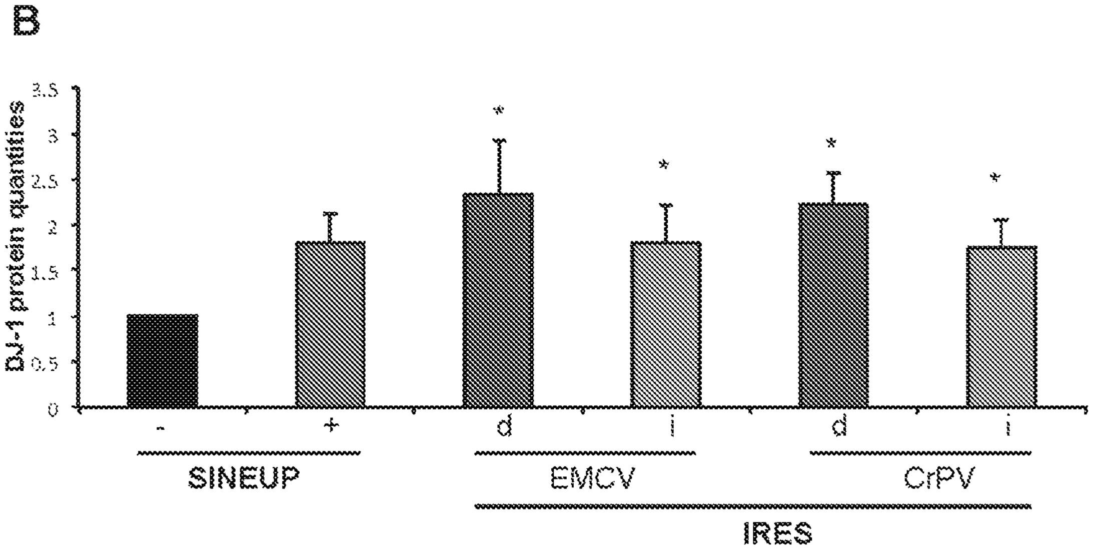

The results are summarised in FIGS. 8A and 8B. As evident, IRES-containing functional nucleic acid molecules activate translation in trans and are more active than SINE-containing molecules. Data represents average and stdev of N>5 biological replicas. Single asterisks (*) indicate IRES sequences that have statistically significant translation enhancement activity in trans relative to empty control cells; double asterisks indicate IRES sequences that show statistically significant increased potency relative to SINE-containing functional nucleic acid molecules.

Example 6

Figure 9:
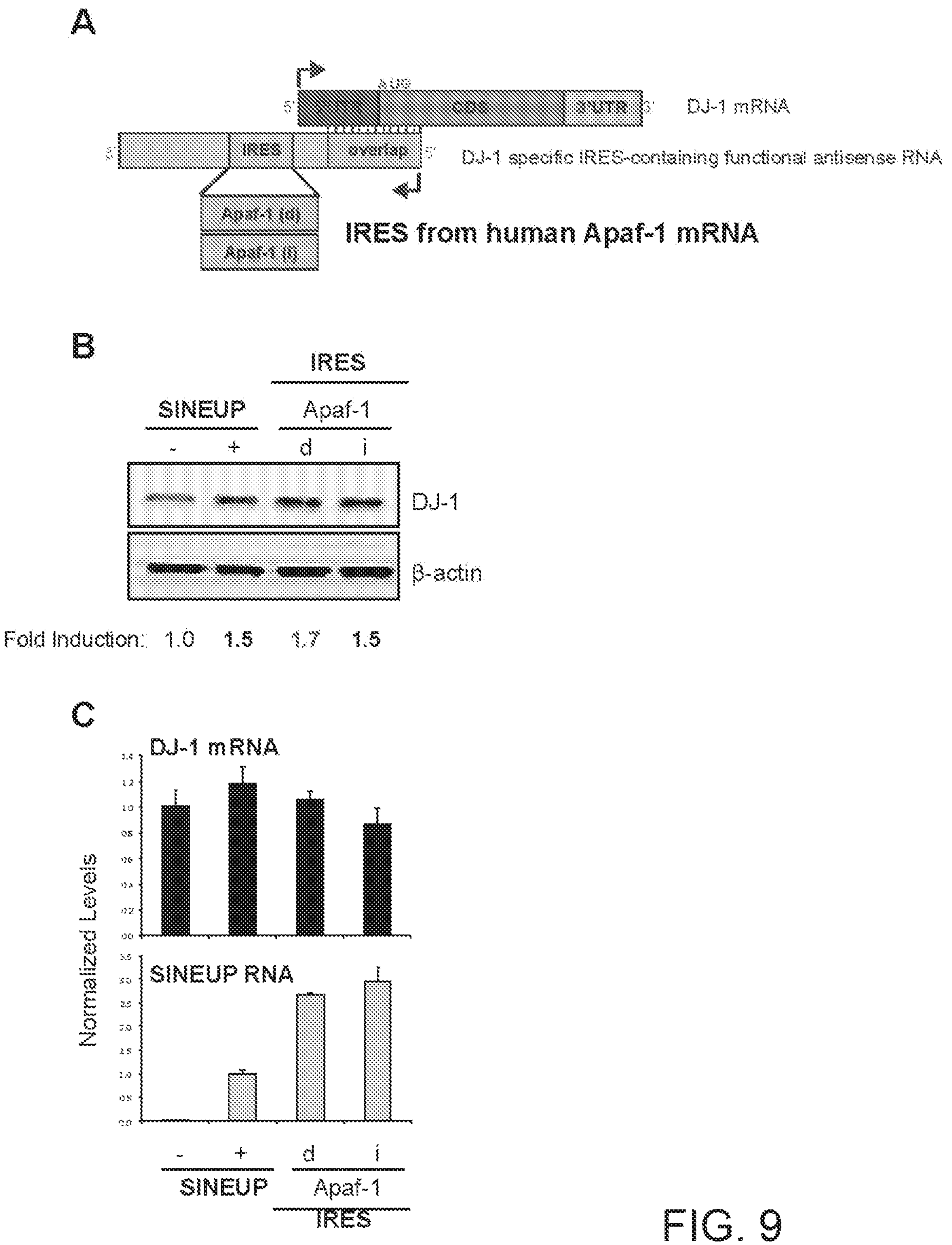
FIG. 9A shows a schematic diagram of a functional nucleic acid molecule according to the present invention (IRUP) targeting the DJ-1 gene and including a human Apoptotic Peptidase Activating Factor 1 (Apaf-1) mRNA IRES.
FIG. 9B shows the results of a Western blot carried out on lysates of HEK 293T/17 cells transfected respectively with empty control plasmid, SINEUP-DJ-1, and an IRUP including an Apaf-1 IRES in direct (Apaf-1(d)) and inverted orientation (Apaf-1(i)).
FIG. 9C shows the results of a qRT-PCR to quantify expression of endogenous DJ-1 mRNA (top panel) and IRUP RNA (bottom panel) carried out on samples as in FIG. 9B.

FIG. 9A shows a schematic diagram of a trans-acting functional nucleic acid molecule in which the effector domain is an IRES sequence from human Apoptotic Peptidase Activating Factor 1 (Apaf-1) mRNA. IRES-containing functional nucleic acid molecules were generated with the Apaf-1 IRES sequence cloned in direct (Apaf-1(d)—SEQ ID NO:9) or inverted (Apaf-1(i)—SEQ ID NO:10) orientation relative to the 5' to 3' orientation of the functional nucleic acid molecule.

HEK 293T/17 cells were transfected with plasmids encoding for IRES-containing functional nucleic acid molecules with Apaf-1 IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 9B) was performed with anti-DJ-1 antibody. β-actin was used as loading control. Fold-induction was calculated on Western blot images normalized to β-actin and relative to empty control samples. Potency of IRES-containing functional nucleic acid molecules was higher or similar with respect to SINE-containing functional nucleic acid molecules.

RNA was purified from transfected cells. Expression of endogenous DJ-1 mRNA and IRUP RNA was monitored by qRT-PCR using specific primers (FIG. 9C). To compare RNA quantities across SINE- and IRES-containing functional nucleic acid molecules, primers were positioned at the 3' end of the Effector Domain. Data indicate mean±st. dev. Data are representative of N>5 independent replicas.

Example 7

Figure 10:
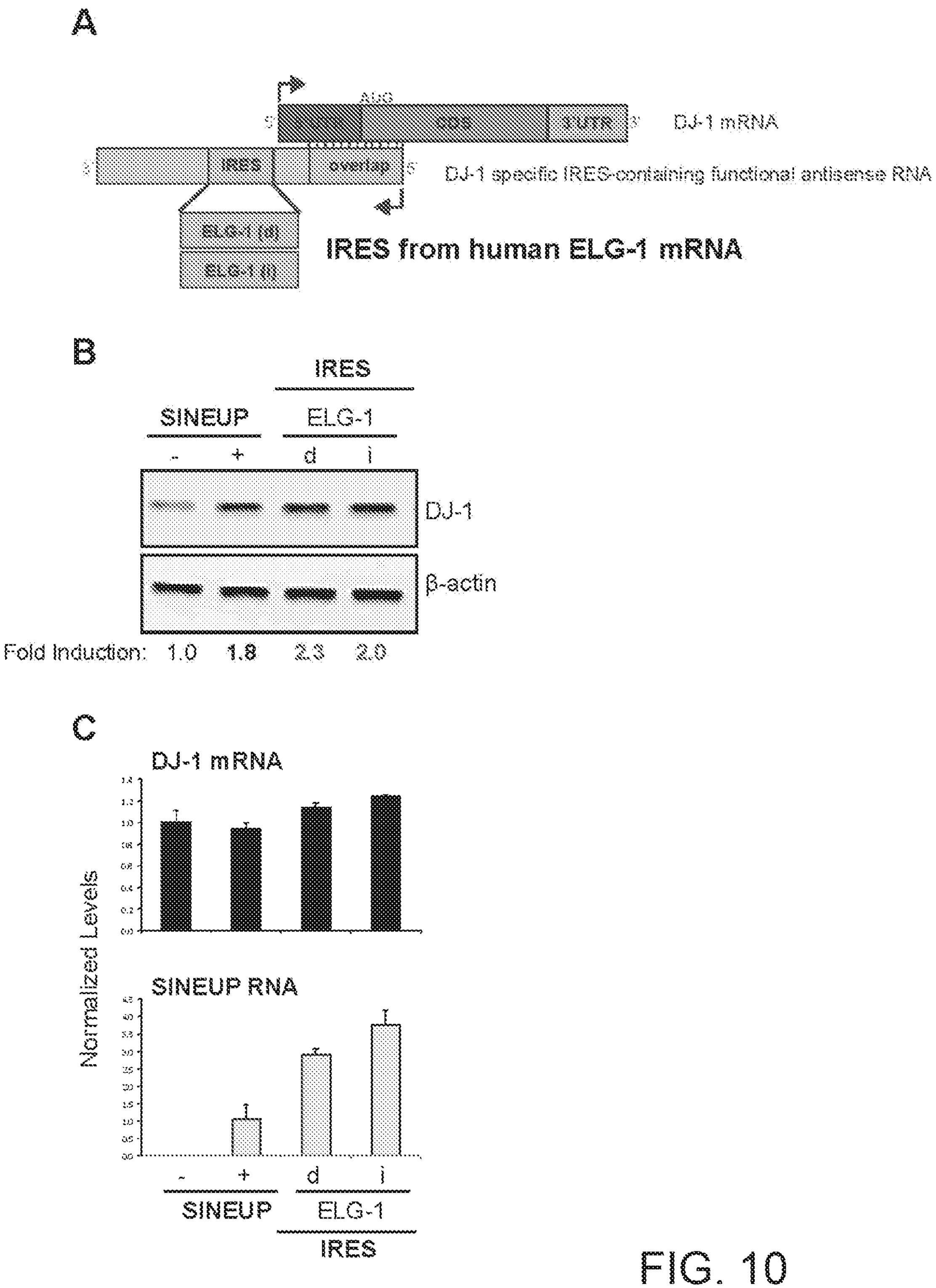
FIG. 10A shows a schematic diagram of a functional nucleic acid molecule according to the present invention (IRUP) targeting the DJ-1 gene and including a human Enhanced Level of Genomic instability 1 (ELG-1) mRNA IRES.
FIG. 10B shows the results of a Western blot carried out on lysates of HEK 293T/17 cells transfected respectively with empty control plasmid, SINEUP-DJ-1, and an IRUP including an ELG-1 IRES in direct (ELG-1(d)) and inverted orientation (ELG-1(i)).
FIG. 10C shows the results of a qRT-PCR to quantify expression of endogenous DJ-1 mRNA (top panel) and IRUP RNA (bottom panel) carried out on samples as in FIG. 10B.

FIG. 10A shows a schematic diagram of a trans-acting functional nucleic acid molecule in which the effector domain is an IRES sequence from human Enhanced Level of Genomic instability 1 (ELG-1) mRNA. IRES-containing functional nucleic acid molecules were generated with the ELG-1 IRES sequence cloned in direct (ELG-1(d)—SEQ ID NO:11) or inverted (ELG-1(i)—SEQ ID NO:12) orientation relative to the 5' to 3' orientation of the functional nucleic acid molecule.

HEK 293T/17 cells were transfected with plasmids encoding for IRES-containing functional nucleic acid molecules with ELG-1 IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 10B) was performed with anti-DJ-1 antibody. β-actin was used as loading control. Fold-induction was calculated on Western blot images normalized to β-actin and relative to empty control samples. Potency of IRES-containing functional nucleic acid molecules was higher with respect to SINE-containing functional nucleic acid molecules.

RNA was purified from transfected cells. Expression of endogenous DJ-1 mRNA and IRUP RNA was monitored by qRT-PCR using specific primers (FIG. 10C). To compare RNA quantities across SINE- and IRES-containing functional nucleic acid molecules, primers were positioned at the 3' end of the Effector Domain. Data indicate mean±st. dev. Data are representative of N>5 independent replicas.

Example 8

Figure 11:
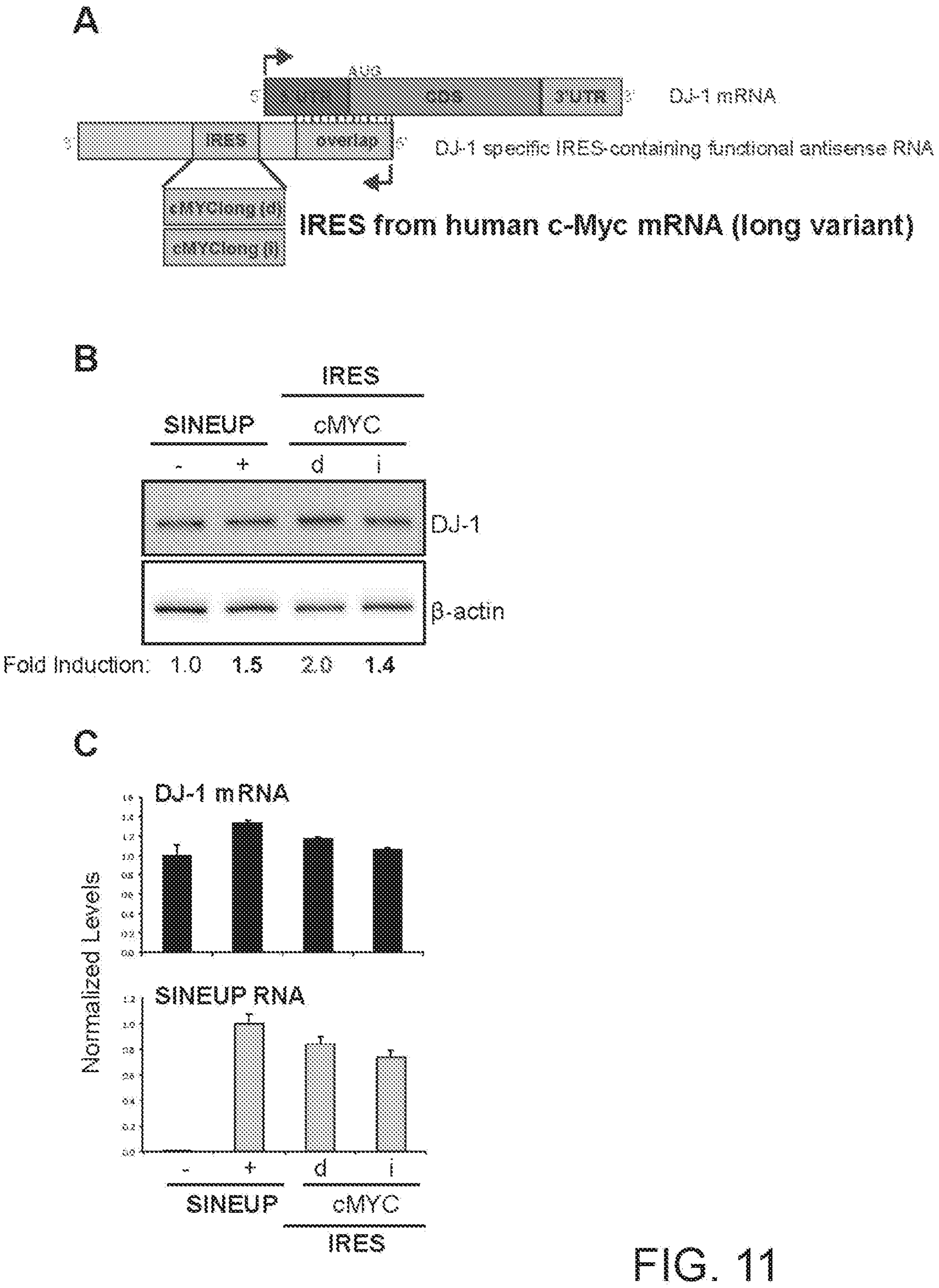
FIG. 11A shows a schematic diagram of a functional nucleic acid molecule according to the present invention (IRUP) targeting the DJ-1 gene and including a human V-Myc Avian Myelocytomatosis Viral Oncogene Homolog (cMYC) mRNA IRES.
FIG. 11B shows the results of a Western blot carried out on lysates of HEK 293T/17 cells transfected respectively with empty control plasmid, SINEUP-DJ-1, and an IRUP including an cMYC IRES in direct (cMYC(d)) and inverted orientation (cMYC(i)).
FIG. 11C shows the results of a qRT-PCR to quantify expression of endogenous DJ-1 mRNA (top panel) and IRUP RNA (bottom panel) carried out on samples as in FIG. 11B.

FIG. 11A shows a schematic diagram of a trans-acting functional nucleic acid molecule in which the effector domain is an IRES sequence from human V-Myc Avian Myelocytomatosis Viral Oncogene Homolog (cMYC) mRNA. IRES-containing functional nucleic acid molecules were generated with the cMYC IRES sequence (long variant) cloned in direct (cMYC full length(d)—SEQ ID NO:13) or inverted (cMYC full length(i)—SEQ ID NO:14) orientation relative to the 5' to 3' orientation of the functional nucleic acid molecule.

HEK 293T/17 cells were transfected with plasmids encoding for IRES-containing functional nucleic acid molecules with cMYC IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 11B) was performed with anti-DJ-1 antibody. β-actin was used as loading control. Fold-induction was calculated on Western blot images normalized to β-actin and relative to empty control samples. Potency of IRES-containing functional nucleic acid molecules was higher or similar with respect to SINE-containing functional nucleic acid molecules.

RNA was purified from transfected cells. Expression of endogenous DJ-1 mRNA and IRUP RNA was monitored by qRT-PCR using specific primers (FIG. 11C). To compare RNA quantities across SINE- and IRES-containing functional nucleic acid molecules, primers were positioned at the 3' end of the Effector Domain. Data indicate mean±st. dev. Data are representative of N>5 independent replicas.

Example 9

Figure 12:
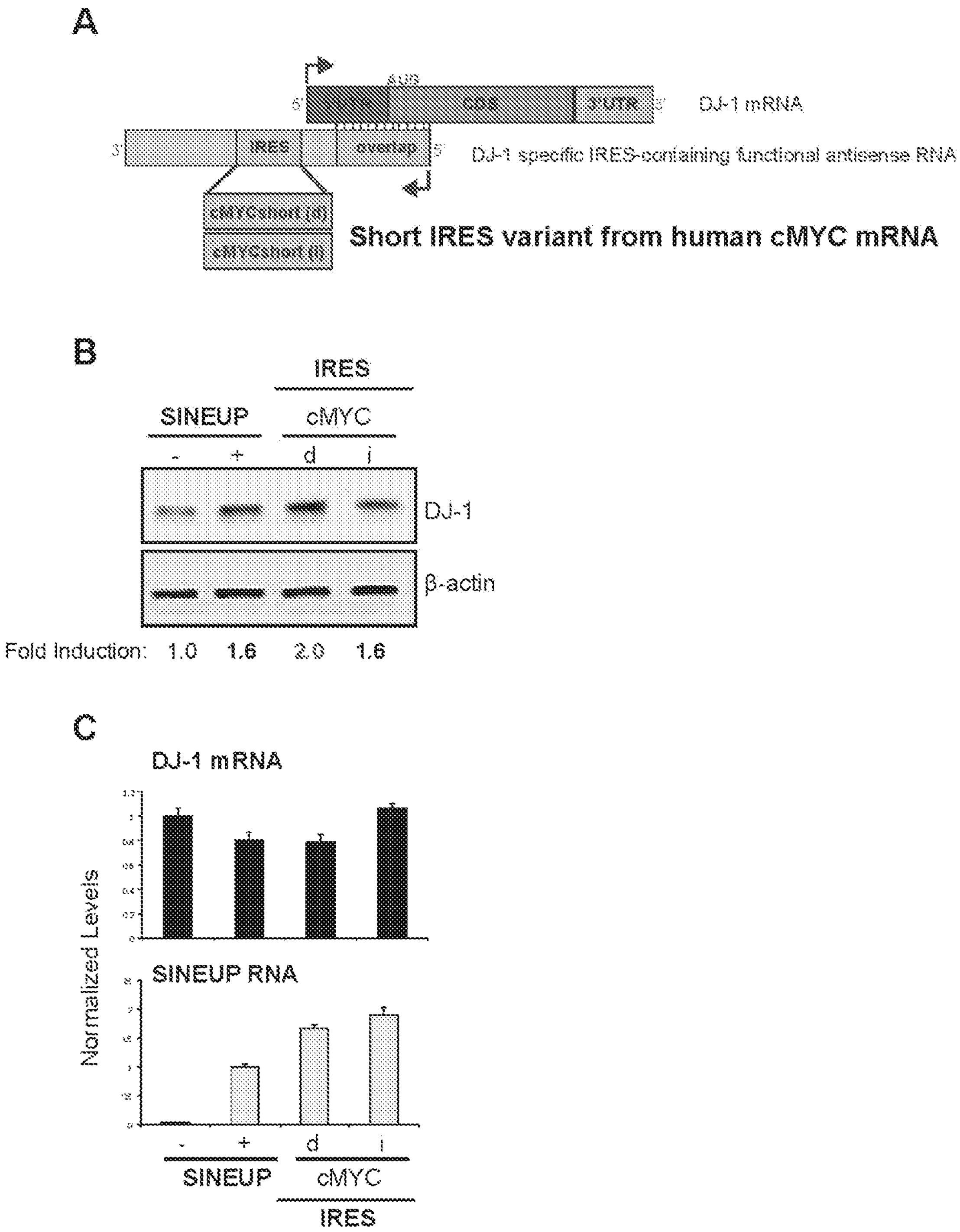
FIG. 12A shows a schematic diagram of a functional nucleic acid molecule according to the present invention (IRUP) targeting the DJ-1 gene and including a shorter version of the human V-Myc Avian Myelocytomatosis Viral Oncogene Homolog (cMYC) mRNA IRES of FIGS. 11A to 11C.
FIG. 12B shows the results of a Western blot carried out on lysates of HEK 293T/17 cells transfected respectively with empty control plasmid, SINEUP-DJ-1, and an IRUP including an cMYC IRES (short variant) in direct (cMYC (d)) and inverted orientation (cMYC(i)).
FIG. 12C shows the results of a qRT-PCR to quantify expression of endogenous DJ-1 mRNA (top panel) and IRUP RNA (bottom panel) carried out on samples as in FIG. 12B.

FIG. 12A shows a schematic diagram of a trans-acting functional nucleic acid molecule in which the effector domain is a shorter version of the IRES sequence from human V-Myc Avian Myelocytomatosis Viral Oncogene Homolog (cMYC) mRNA of Example 8. IRES-containing functional nucleic acid molecules were generated with the cMYC IRES sequence (short variant) cloned in direct (cMYC short variant(d)—SEQ ID NO:15) or inverted (cMYC short variant(i)—SEQ ID NO:16) orientation relative to the 5' to 3' orientation of the functional nucleic acid molecule.

HEK 293T/17 cells were transfected with plasmids encoding for IRES-containing functional nucleic acid molecules with cMYC IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 11B) was performed with anti-DJ-1 antibody. β-actin was used as loading control. Fold-induction was calculated on Western blot images normalized to β-actin and relative to empty control samples. Potency of IRES-containing functional nucleic acid molecules was higher or similar with respect to SINE-containing functional nucleic acid molecules.

RNA was purified from transfected cells. Expression of endogenous DJ-1 mRNA and IRUP RNA was monitored by qRT-PCR using specific primers (FIG. 12C). To compare RNA quantities across SINE- and IRES-containing functional nucleic acid molecules, primers were positioned at the 3' end of the Effector Domain. Data indicate mean±st. dev. Data are representative of N>5 independent replicas.

Example 10

Figure 13:
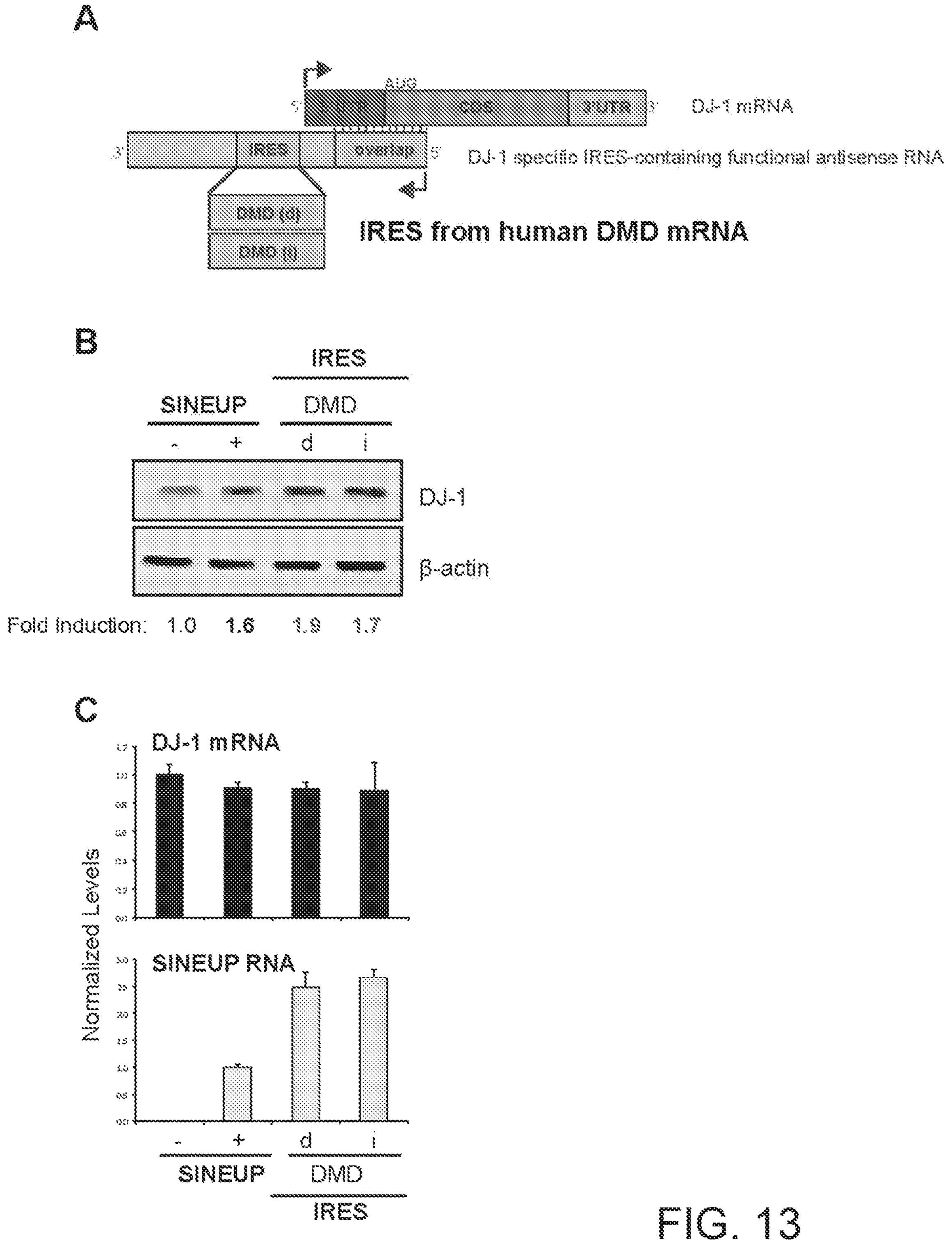
FIG. 13A shows a schematic diagram of a functional nucleic acid molecule according to the present invention (IRUP) targeting the DJ-1 gene and including a human Dystrophin (DMD) mRNA IRES.
FIG. 13B shows the results of a Western blot carried out on lysates of HEK 293T/17 cells transfected respectively with empty control plasmid, SINEUP-DJ-1, and an IRUP including an DMD IRES in direct (DMD(d)) and inverted orientation (DMD(i)).
FIG. 13C shows the results of a qRT-PCR to quantify expression of endogenous DJ-1 mRNA (top panel) and IRUP RNA (bottom panel) carried out on samples as in FIG. 13B.

FIG. 13A shows a schematic diagram of a trans-acting functional nucleic acid molecule in which the effector domain is an IRES sequence from human Dystrophin (DMD) mRNA. IRES-containing functional nucleic acid molecules were generated with the DMD IRES sequence cloned in direct (DMD(d)—SEQ ID NO:17) or inverted (DMD(i)—SEQ ID NO:18) orientation relative to the 5' to 3' orientation of the functional nucleic acid molecule.

HEK 293T/17 cells were transfected with plasmids encoding for IRES-containing functional nucleic acid molecules with DMD IRES sequence in direct (d) or inverted (i) orientation, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 13B) was performed with anti-DJ-1 antibody. β-actin was used as loading control. Fold-induction was calculated on Western blot images normalized to β-actin and relative to empty control samples. Potency of IRES-containing functional nucleic acid molecules was higher with respect to SINE-containing functional nucleic acid molecules.

RNA was purified from transfected cells. Expression of endogenous DJ-1 mRNA and IRUP RNA was monitored by qRT-PCR using specific primers (FIG. 13C). To compare RNA quantities across SINE- and IRES-containing functional nucleic acid molecules, primers were positioned at the 3' end of the Effector Domain. Data indicate mean±st. dev. Data are representative of N>5 independent replicas.

Example 11

The increase in quantities of endogenous DJ-1 protein in HEK 293T/17 cells transfected with Apaf-1(d) and Apaf-1(i) IRUPs of Example 6, ELG-1(d) and ELG-1(i) IRUPs of Example 7, cMYC full length(d) and cMYC full length(i) IRUPs of Example 8, cMYC short variant(d) and cMYC short variant(i) IRUPs of Example 9, and DMD(d) and DMD(i) IRUPs of Example 10 relative to empty vector transfected HEK 293T/17 cells was measured by Western blot.

Figure 14:
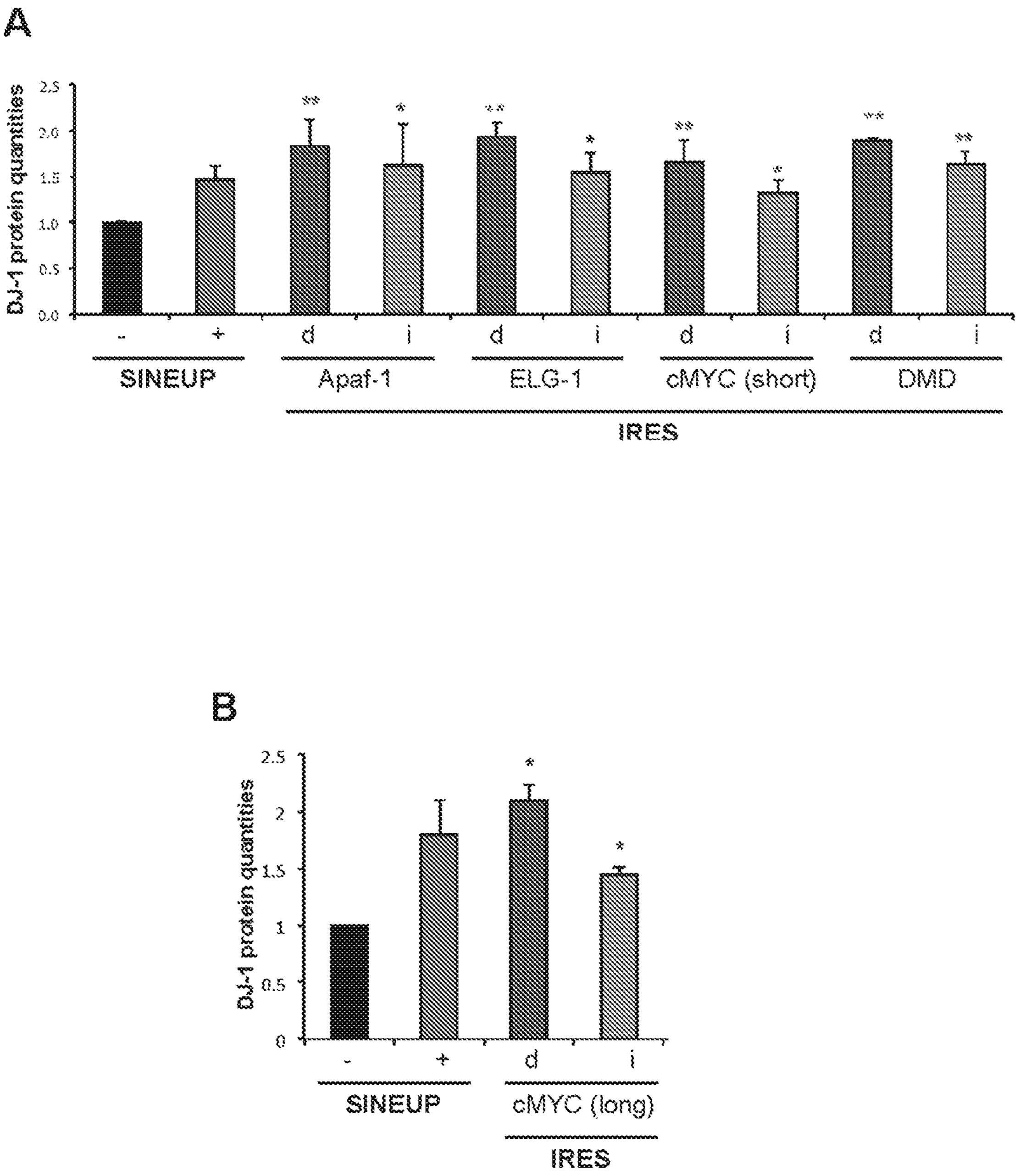
FIGS. 14A and 14B show graphs summarising the increase in quantities of DJ-1 protein in HEK 293T/17 cells transfected with Apaf-1(d) and Apaf-1(i) IRUPs, ELG-1(d) and ELG-1(i) IRUPs, cMYC(d) short version and cMYC(i) short version IRUPs, DMD(d) and DMD(i) IRUPs, and cMYC(d) long version and cMYC(i) long version IRUPs of the present invention relative to empty vector transfected 293T/17 cells.

The results are summarised in FIGS. 14A and 14B. As evident, IRES-containing functional nucleic acid molecules activate translation in trans and are more active than SINE-containing molecules. Data represents average and stdev of N>5 biological replicas. Single asterisks (*) indicate IRES sequences that have statistically significant translation enhancement activity in trans relative to empty control cells; double asterisks indicate IRES sequences that show statistically significant increased potency relative to SINE-containing functional nucleic acid molecules.

Example 12

Human hepatocellular carcinoma (HepG2) cells were transfected with plasmids encoding for IRES-containing functional nucleic acid molecules with HCV (FIG. 15A) IRES sequence in direct (d) or inverted (i) orientation (SEQ ID NO:1 or SEQ ID NO:2), with Polio and cMYC (FIG. 15B) IRES sequence in direct (d) or inverted (i) orientation (SEQ ID NO:3, SEQ ID NO:4, SEQ ID NO:13 or SEQ ID NO:14), with Apaf-1 and ELG-1 (FIG. 15C) IRES sequence in direct (d) or inverted (i) orientation (SEQ ID NO:9, SEQ ID NO:10, SEQ ID NO:11 or SEQ ID NO:12), and with DMD (FIG. 15D) IRES sequence in direct (d) or inverted (i) orientation (SEQ ID NO:17 or SEQ ID NO:18), as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot was performed with anti-DJ-1 antibody. β-actin was used as loading control. Fold-induction was calculated on Western blot images normalized to β-actin and relative to empty control samples. Potency of IRES-containing functional nucleic acid molecules was almost always higher than SINE-containing functional nucleic acid molecules.

Example 13

The increase in quantities of endogenous DJ-1 protein in HepG2 cells transfected with HCV(d) and HCV(i) IRUPs, Polio(d) and Polio(i) IRUPs and cMYC short variant(d) and cMYC short variant(i) IRUPs, Apaf-1(d) and Apaf-1(i) IRUPs, ELG-1(d) and ELG-1(i) IRUPs, DMD (d) and DMD (i) IRUPs relative to empty vector transfected HepG2 cells was measured by Western blot.

Figure 16:
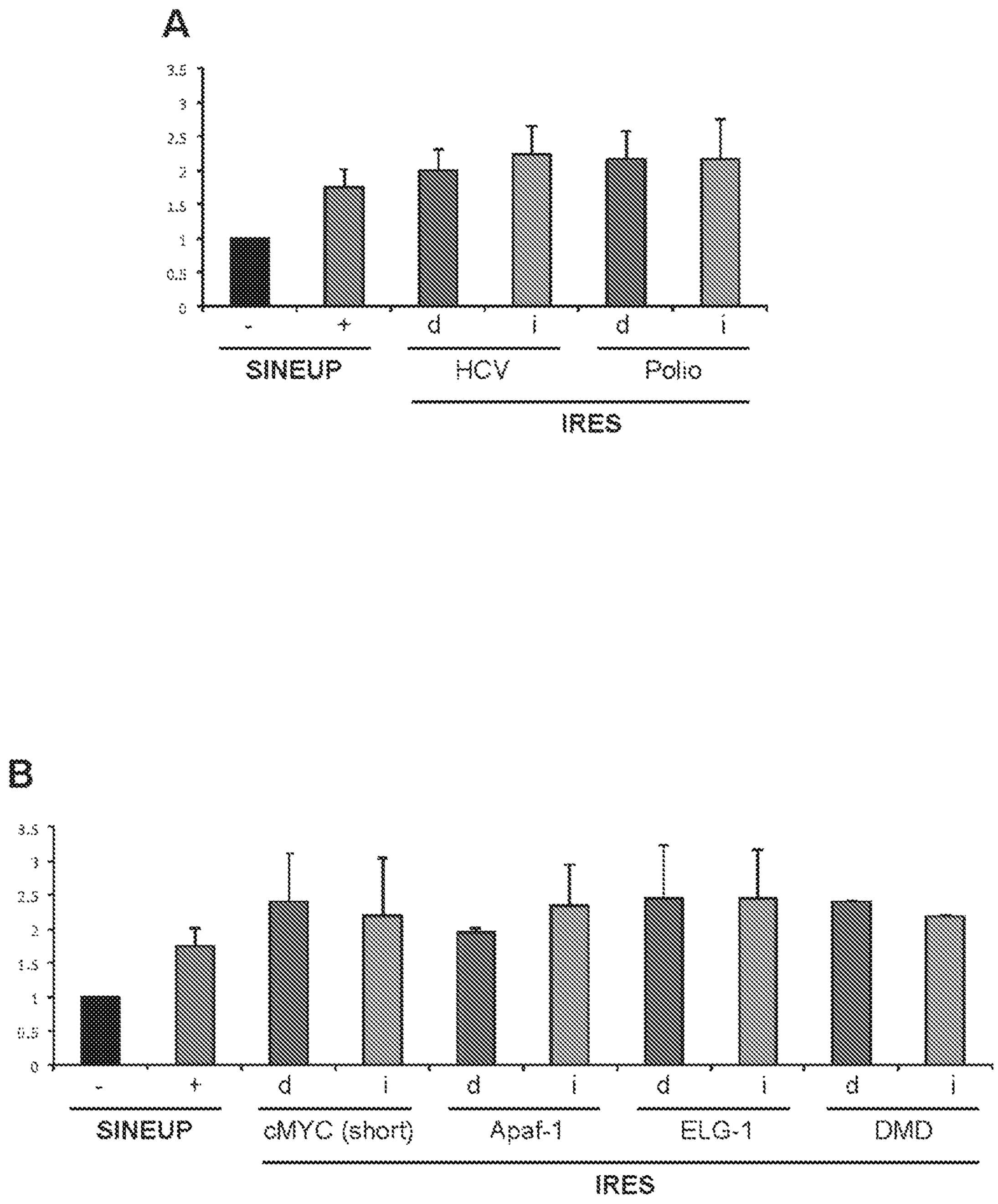
FIGS. 16A and 16B show graphs summarising the increase in quantities of DJ-1 protein in HepG2 cells transfected with HCV(d) and HCV(i) IRUPs, Polio(d) and Polio (i) IRUPs, cMYC(d) short version and cMYC(i) short version IRUPs, Apaf-1(d) and Apaf-1(i) IRUPs, ELG-1(d) and ELG-1(i) IRUPs, and DMD(d) and DMD(i) IRUPs of the present invention relative to empty vector transfected HepG2 cells.

The results are summarised in FIGS. 16A-16B. IRES-containing functional nucleic acid molecules activate translation in trans and are more active than SINE-containing molecules. Data represents average and stdev of N>2 biological replicas.

Example 14

Figure 17:
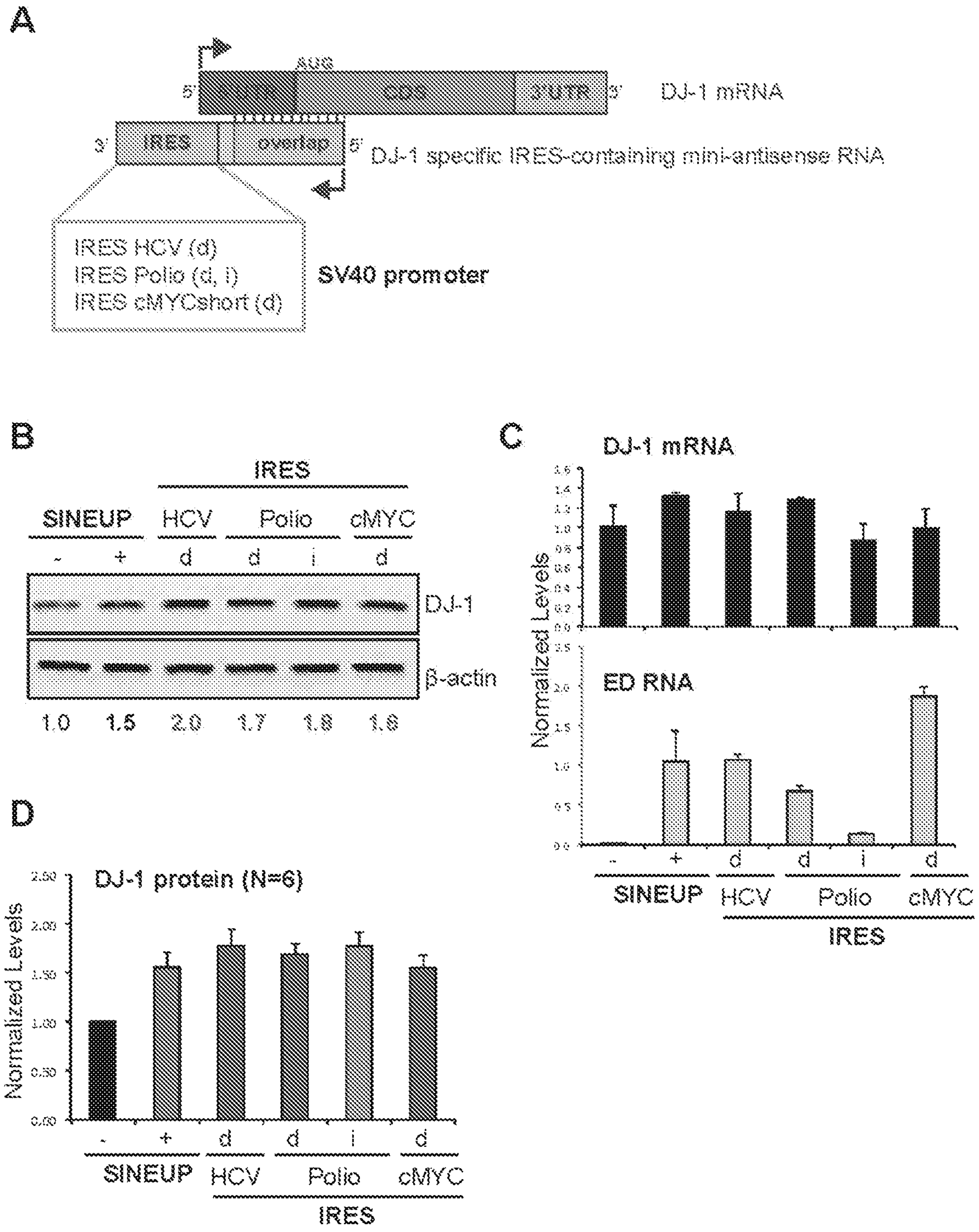
FIG. 17A shows a schematic diagram of a miniaturised version of functional nucleic acid molecules according to the present invention (miniIRUP) targeting the DJ-1 gene.
FIG. 17B shows the results of a Western blot carried out on lysates of HEK 293T/17 cells transfected respectively with empty control plasmid, SINEUP-DJ-1 and miniIRUPs including an HCV IRES in direct orientation (HCV(d)), a Poliovirus IRES in direct (Polio(d)) and inverted orientation (Polio(i)) and a cMYC short version IRES in direct orientation (cMYC short(d)).
FIG. 17C shows the results of a qRT-PCR to quantify expression of endogenous DJ-1 mRNA (top panel) and IRUP RNA (bottom panel) carried out on samples as in FIG. 17B.
FIG. 17D shows a graphical representation of SINEUP-DJ-1 and mini-IRUP translation enhancement activity on endogenous DJ-1 mRNA in HEK 293T/17 cells (N=6).

FIG. 17A shows a schematic diagram of a miniaturised version of a trans-acting functional nucleic acid molecule (miniIRUP) in which the effector domain is an IRES sequence from HCV, Poliovirus or cMYC short version. IRES-containing functional nucleic acid molecules were generated with the HCV IRES sequence cloned in direct (HCV(d)—SEQ ID NO:31) orientation, with the Polio IRES sequence cloned in direct (Polio(d)—SEQ ID NO:32) and inverted (Polio(i)—SEQ ID NO:33) orientation and with the cMYC short IRES sequence cloned in direct (cMYC short variant(d)—SEQ ID NO:34) orientation, under the control of an SV40-based promoter for expression by RNA polymerase II in mammalian cells.

HEK 293T/17 cells were transfected with plasmids encoding the above said mini IRES-containing functional nucleic acid molecules, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 17B) was performed with anti-DJ-1 antibody. β-actin was used as loading control. Fold-induction was calculated on Western blot images normalized to β-actin and relative to empty control samples. Potency of mini IRES-containing functional nucleic acid molecules was higher than SINE-containing functional nucleic acid molecules.

RNA was purified from transfected cells. Expression of endogenous DJ-1 mRNA and mini-IRUP RNA was monitored by qRT-PCR using specific primers (FIG. 17C).

FIG. 17D shows a graphical representation of SINEUP-DJ-1 and mini-IRUP translation enhancement activity on endogenous DJ-1 mRNA in HEK 293T/17 cells (N=6).

Example 15

Figure 18:
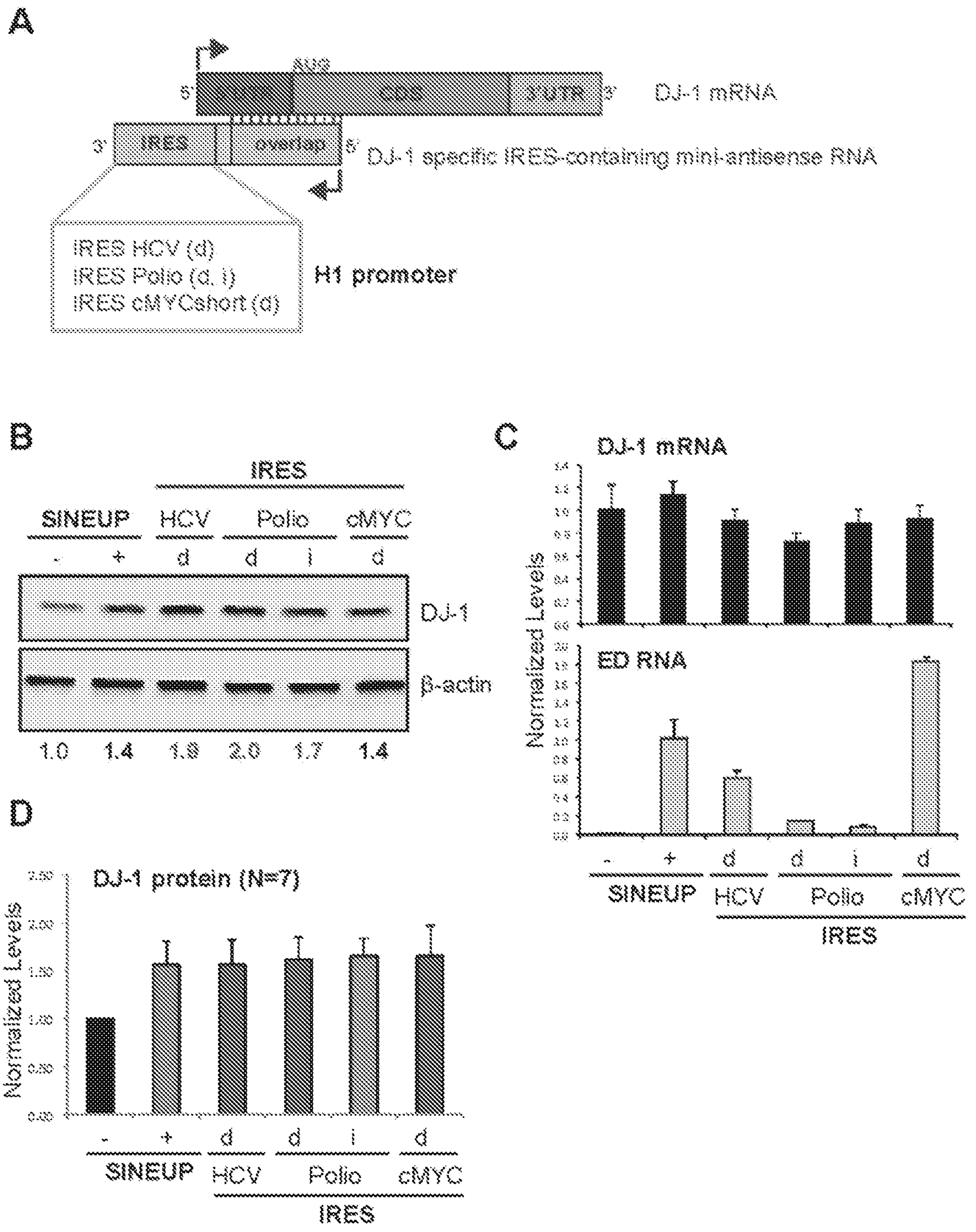
FIG. 18A shows a schematic diagram of a miniaturised version of functional nucleic acid molecules according to the present invention (miniIRUP) targeting the DJ-1 gene. With respect to the miniIRUPs of FIGS. 17A-17D, the IRES-containing functional nucleic acid sequences are cloned under the control of a different promoter.
FIG. 18B shows the results of a Western blot carried out on lysates of HEK 293T/17 cells transfected respectively with empty control plasmid, SINEUP-DJ-1 and miniIRUPs including an HCV IRES in direct orientation (HCV(d)), a Poliovirus IRES in direct (Polio(d)) and inverted orientation (Polio(i)) and a cMYC short version IRES in direct orientation.
FIG. 18C shows the results of a qRT-PCR to quantify expression of endogenous DJ-1 mRNA (top panel) and IRUP RNA (bottom panel) carried out on samples as in FIG. 18B.
FIG. 18D shows a graphical representation of SINEUP-DJ-1 and mini-IRUP translation enhancement activity on endogenous DJ-1 mRNA in HEK 293T/17 cells (N=6).

FIG. 18A shows a schematic diagram of a miniaturised version of a trans-acting functional nucleic acid molecule (miniIRUP) in which the effector domain is an IRES sequence from HCV, Poliovirus or cMYC short version. IRES-containing functional nucleic acid molecules were generated with the HCV IRES sequence cloned in direct (HCV(d)—SEQ ID NO:31) orientation, with the Polio IRES sequence cloned in direct (Polio(d)—SEQ ID NO:32) and inverted (Polio(i)—SEQ ID NO:32) orientation and with the cMYC short IRES sequence cloned in direct (cMYC short version(d)—SEQ ID NO:34) orientation, under the control of an H1-based promoter for expression by RNA polymerase III in mammalian cells.

HEK 293T/17 cells were transfected with plasmids encoding the above said mini IRES-containing functional nucleic acid molecules, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 18B) was performed with anti-DJ-1 antibody. β-actin was used as loading control. Fold-induction was calculated on Western blot images normalized to β-actin and relative to empty control samples. Potency of mini IRES-containing functional nucleic acid molecules was higher (similar in one case) with respect to SINE-containing functional nucleic acid molecules.

RNA was purified from transfected cells. Expression of endogenous DJ-1 mRNA and mini-IRUP RNA was monitored by qRT-PCR using specific primers (FIG. 18C).

FIG. 18D shows a graphical representation of SINEUP-DJ-1 and mini-IRUP translation enhancement activity on endogenous DJ-1 mRNA in HEK 293T/17 cells (N=6).

Example 16

Figure 19:
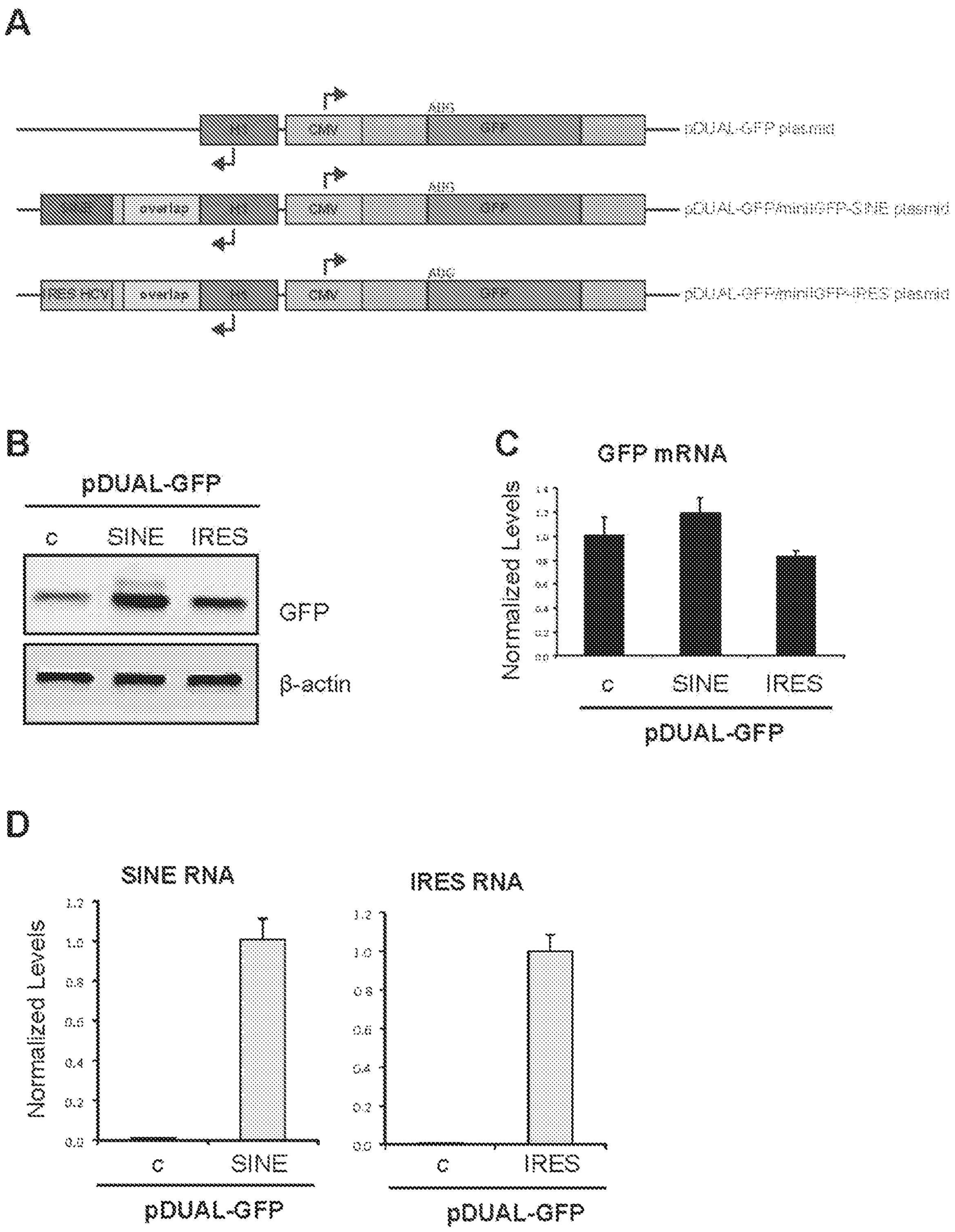
FIG. 19A shows a schematic diagram of pDUAL-GFP plasmids for the concomitant expression of functional nucleic acid molecule and genes of interest in mammalian cells.
FIG. 19B shows the results of a Western blot carried out on lysates of HEK 293T/17 cells transfected respectively with empty control plasmid, SINE-containing (SINE) or IRES-containing (IRES) mini-functional nucleic acid molecules shown in FIG. 19A.
FIG. 19C shows the results of a qRT-PCR to quantify expression of overexpressed GFP mRNA in HEK 293T/17 cells transfected with the constructs of FIG. 19A.
FIG. 19D shows the results of a qRT-PCR to quantify expression of functional nucleic acid SINE or IRES RNA.

FIG. 19A shows a schematic diagram of pDUAL-GFP plasmids for the concomitant expression of two genes of interest in mammalian cells. pDUAL-GFP plasmids contain a CMV promoter element for the expression of GFP mRNA by RNA Polymerase II and an H1 promoter (in opposite orientation) for the expression of GFP-targeting miniaturized version of functional nucleic acid molecules for GFP translation enhancement. A control plasmid is produced that lacks the translation enhancer functional nucleic acid molecule and expressed basal levels of GFP protein. pDUAL-GFP/miniGFP plasmids were created in which the effector domain is represented by a SINE B2 sequence or by the HCV IRES, as indicated.

HEK 293T/17 cells were transfected with pDUAL plasmids encoding for GFP alone or GFP in combination with SINE-containing (SINE) or IRES-containing (IRES) mini-functional nucleic acid molecules. Cells transfected with pDUAL-GFP alone were used as reference for testing the potency of IRES-containing molecules. 48 hours after transfection, cells were lysed and processed for protein quantities. Western blot (FIG. 19B) was performed with anti-GFP antibody. β-actin was used as loading control.

RNA was purified from transfected cells. Expression of overexpressed GFP mRNA (FIG. 19C) and functional nucleic acid SINE or IRES RNA (FIG. 19D) was monitored by qRT-PCR using specific primers.

The results show that IRES-containing functional nucleic acid molecules bearing a Binding Domain antisense to GFP mRNA enhance translation of GFP mRNA when GFP is overexpressed in HEK 293T/17 cells.

Example 17

Figure 20:
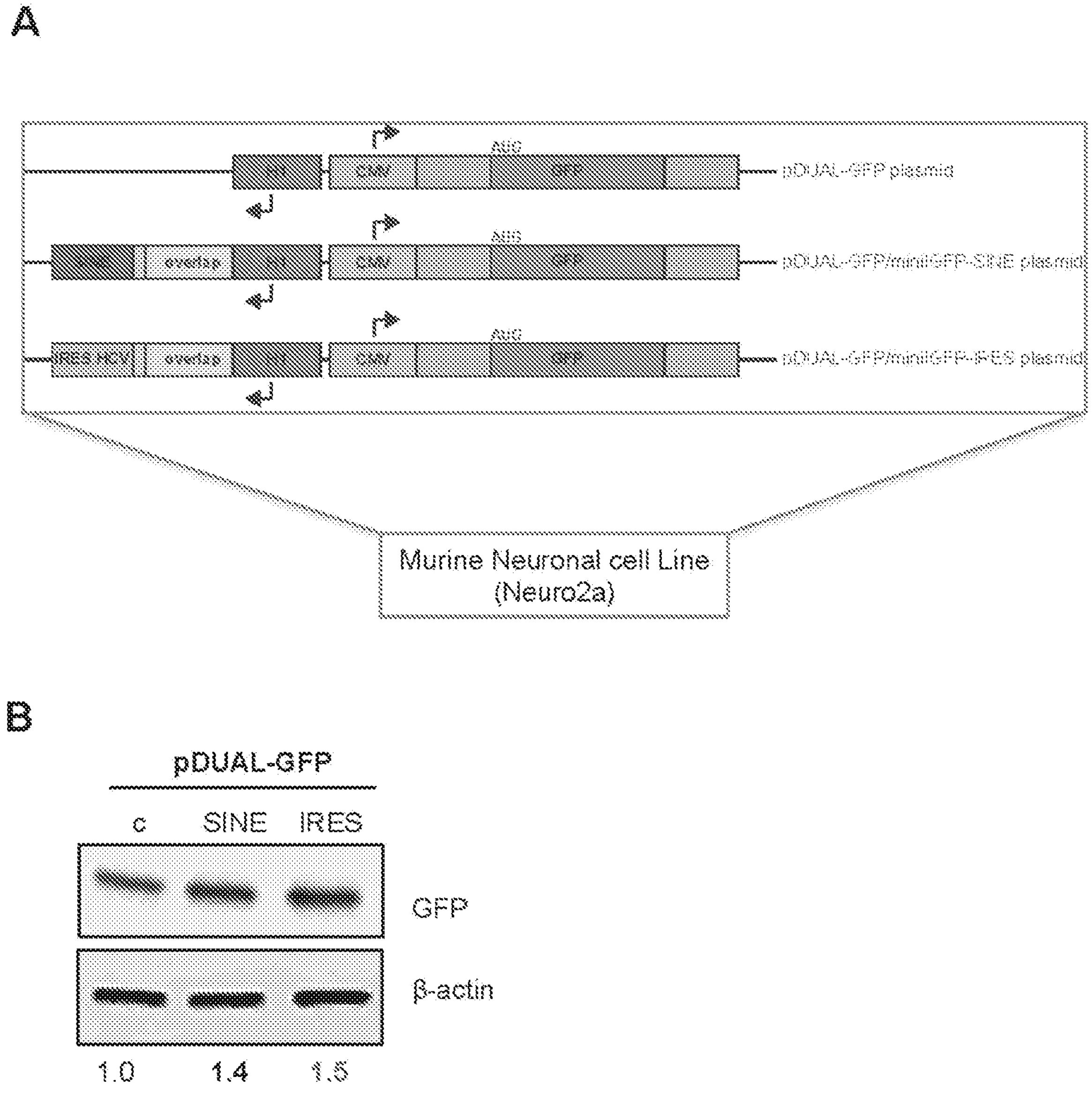
FIG. 20A shows a schematic diagram of pDUAL-GFP plasmids with GFP targeting functional nucleic acid molecules in which the Effector Domain is represented by the SINE or HCV IRES sequence.
FIG. 20B shows the results of a Western blot carried out on lysates of human neuroblastoma Neuro2a cells transfected respectively with empty control plasmid, SINE-containing (SINE) or IRES-containing (IRES) mini-functional nucleic acid molecules shown in FIG. 20A.

FIG. 20A shows a schematic diagram of pDUAL-GFP plasmids with GFP targeting functional nucleic acid molecules in which the Effector Domain is represented by the SINE or HCV IRES sequence.

Human neuroblastoma Neuro2a cells were transfected with the pDUAL-GFP plasmids shown in FIG. 20A. 48 hours after transfection, cells were lysed and processed for protein quantities. Western blot (FIG. 20B) was performed with anti-GFP antibody. β-actin was used as loading control. Fold-induction was calculated on Western blot images normalized to β-actin and relative to empty control samples. Potency of mini IRES-containing functional nucleic acid molecules was higher than SINE-containing functional nucleic acid molecules.

Example 18

Functional nucleic acid molecules containing DJ-1 targeting Binding Domain and HCV IRES Effector Domain harboring specific mutations in structural regions important for HCV IRES activity in cis were designed.

Figure 21:
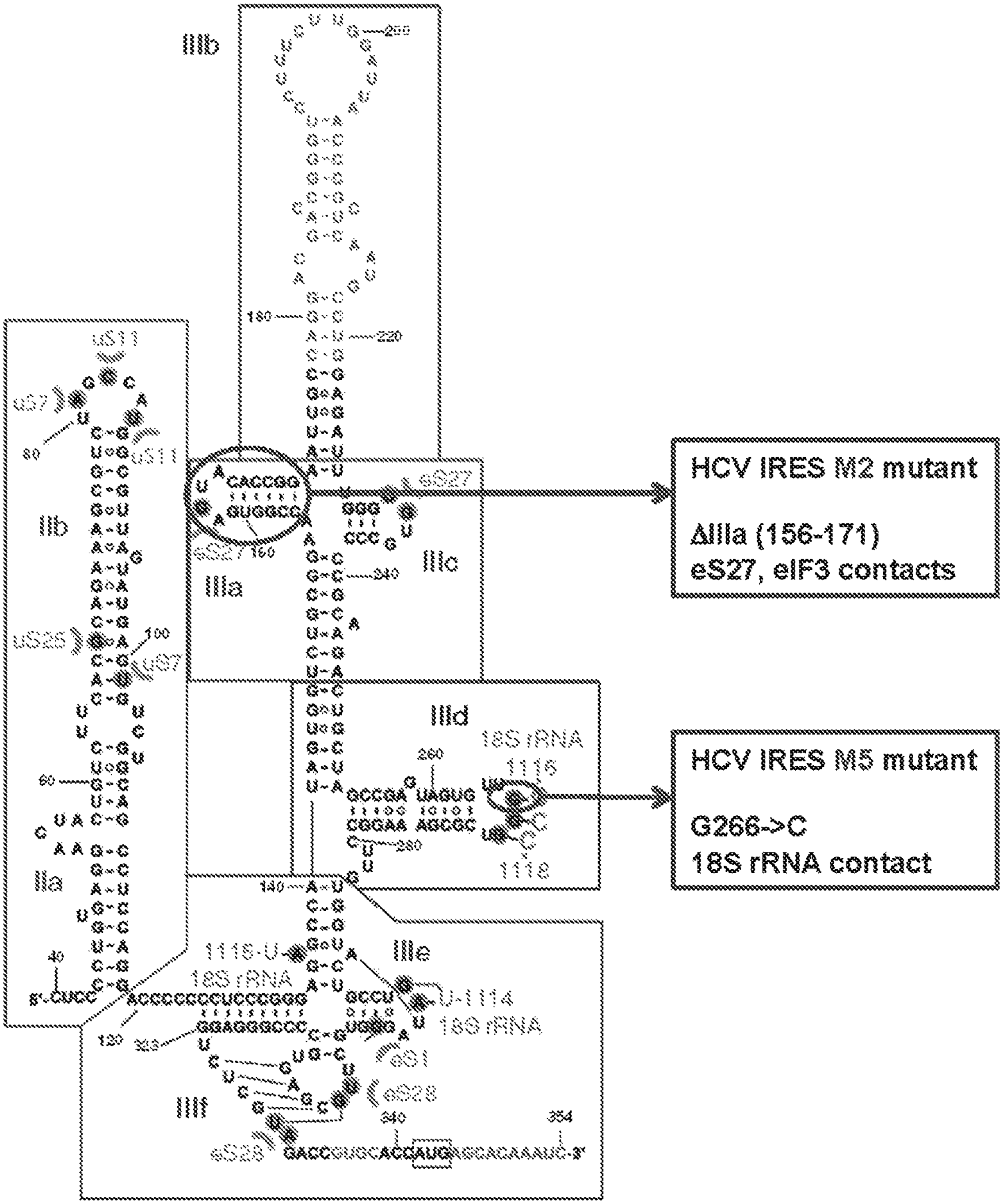
FIG. 21 shows a schematic representation of HCV IRES RNA secondary structure.

FIG. 21 shows a schematic representation of HCV IRES RNA secondary structure. HCV IRES structural domains (IIa, IIb, IIIa, IIIb, IIIc, IIId, IIIe and IIIf) are indicated in the different squares. The functionality of each structural domain for the Internal Ribosome Entry activity of the sequence is also shown, with contacts to ribosomal RNA and/or ribosomal proteins. A functional nucleic acid molecule in which the Effector Domain is represented by the IRES sequence derived from HCV and containing DJ-1 targeting Binding Domain was used as template for mutagenesis. An M2 mutant was produced by deletion of the IIIa stem loop (aminoacids 156-171 of HCV IRES sequence–IRES=SEQ ID NO:55; IRUP=SEQ ID NO:20), involved in contacts with the eukaryotic translation initiation factor eIF3 and the ribosomal protein eS27. An M5 mutant was produced by site-directed nucleotide substitution of nucleotide G266 (G266→C–IRES=SEQ ID NO:58; IRUP=SEQ ID NO:23), fundamental for base-pairing to 18S rRNA and for HCV IRES activity in cis.

Example 19

HEK 293T/17 cells were transfected with a mammalian expression plasmid encoding for IRES-containing functional nucleic acid molecule with HCV IRES sequence in direct orientation (WT) or with HCV IRES DIIIa (M2) or G266→C (M5) mutants, as indicated. Control cells were transfected with an empty control plasmid (−). Cells transfected with SINEUP-DJ-1 were used as reference for testing the potency of IRES-containing molecules. 48 hours after transfection, cells were lysed and processed for protein quantities. Western blot (FIG. 22A) was performed with anti-DJ-1 antibody. β-actin was used as loading control. Fold-induction was calculated on Western blot images normalized to β-actin and relative to empty control samples.

Potency of WT and mutated IRES-containing functional nucleic acid molecule was higher or similar with respect to SINE-containing functional nucleic acid molecule.

Figure 22:
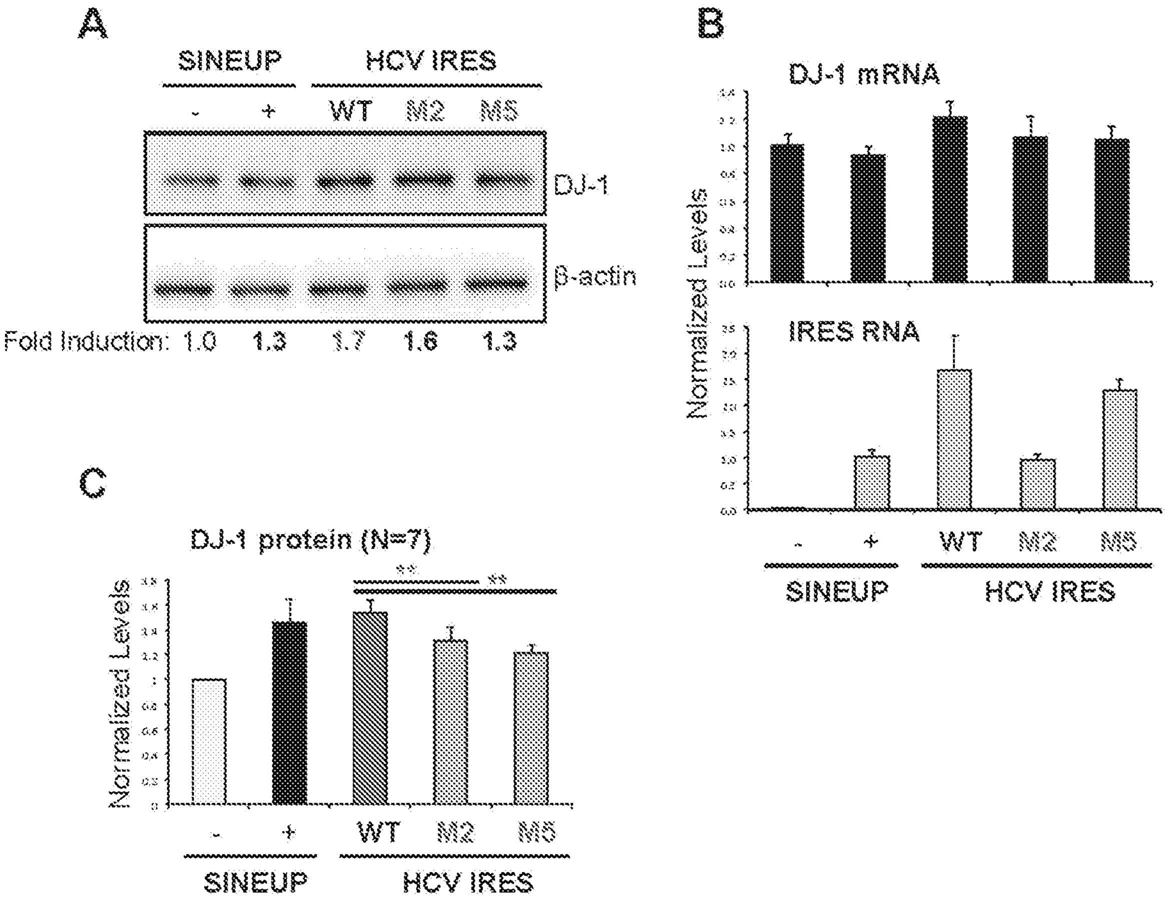
FIG. 22A shows the results of a Western blot carried out on lysates of HEK 293T/17 cells transfected respectively with empty control plasmid, SINEUP-DJ-1 and IRUPs including a WT HCV IRES and the M2 and M5 mutated HCV IRESs.
FIG. 22B shows the results of a qRT-PCR to quantify expression of endogenous DJ-1 mRNA (top panel) and IRUP RNA (bottom panel) carried out on samples as in FIG. 22A.
FIG. 22C shows a graphical representation of SINEUP-DJ-1 and IRUP translation enhancement activity on endogenous DJ-1 mRNA in HEK 293T/17 cells (N=7).

RNA was purified from transfected cells. Expression of endogenous DJ-1 mRNA and functional nucleic acid RNA was monitored by qRT-PCR using specific primers (FIG. 22B). To compare RNA quantities across SINE- and IRES-containing functional nucleic acid molecules, primers were positioned at the 3' end of the Effector Domain. Data indicate mean±st. dev.

FIG. 22C shows a graphical representation of translation enhancement activity of functional nucleic acid molecules with SINE- or HCV IRES-embedded sequences on endogenous DJ-1 mRNA in HEK 293T/17 cells (N=7). Double asterisks (**) indicate mutant IRES sequences that show statistically significant reduction in translation enhancement relative to WT HCV IRES-containing functional nucleic acid molecule.

This example shows that structural elements required for HCV IRES activity in cis contribute to the increased translation enhancement activity of HCV IRES in trans as embedded Effector Domain (ED) in a functional nucleic acid molecule containing DJ-1 targeting Binding Domain.

Example 20

This example shows that any nucleic acid sequence in the target mRNA can be recognised by the Binding Domain of an IRES-derived sequence containing a functional nucleic acid molecule.

Figure 23:
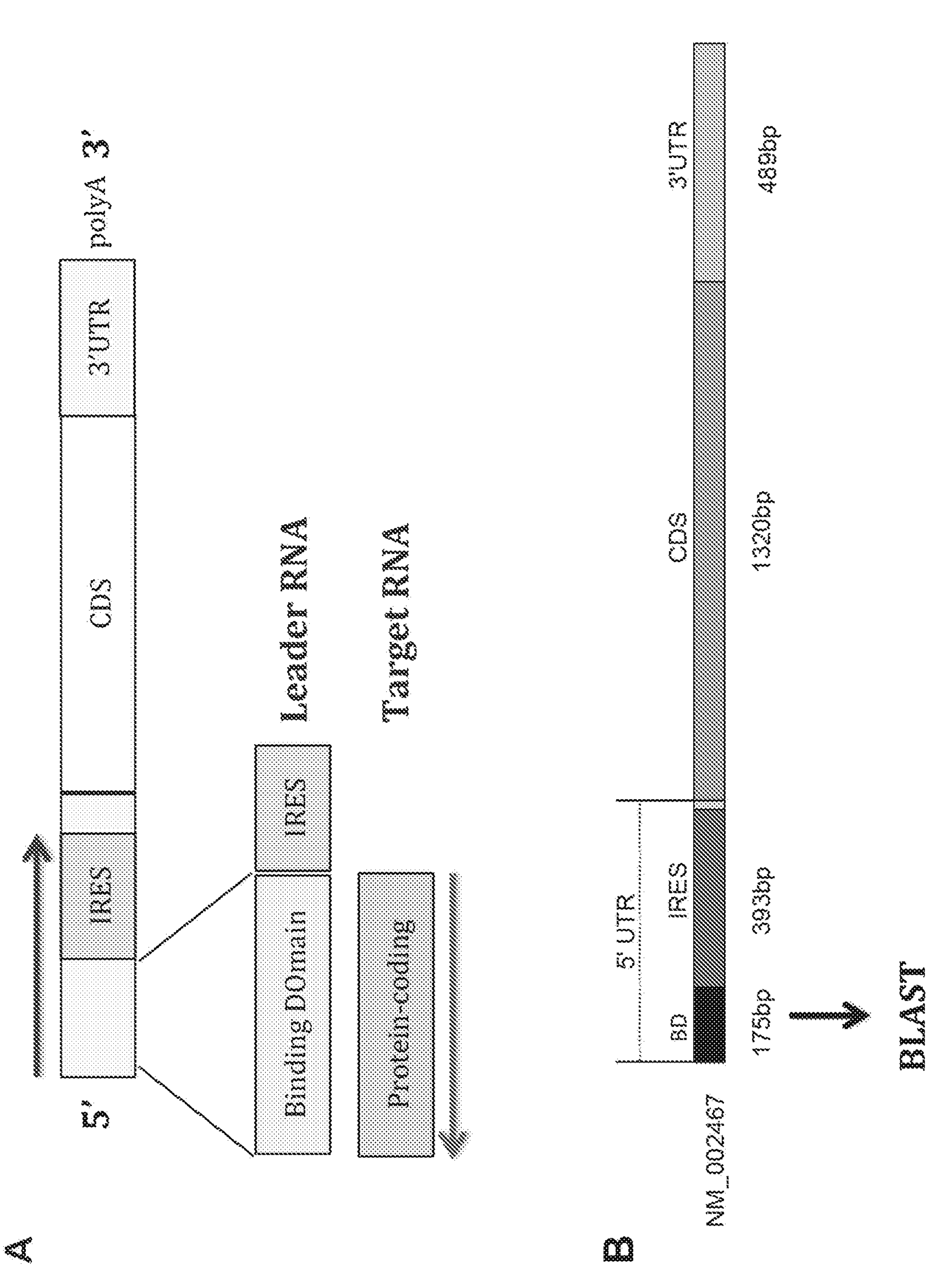
FIG. 23A shows a schematic representation of how the sequence at the 5' of an IRES sequence and within an IRES-containing cellular mRNA can be considered as Binding Domain.
FIG. 23B shows functional nucleic acid sequence elements within cMYC mRNA reference sequence (NM_002467). The Binding Domain (black), IRES sequence (dark grey), the coding sequence or CDS (light grey) and 3' untranslated region (white) are indicated.
FIG. 23C shows the results of the bioinformatics analysis (BLAST) using the c-MYC mRNA as query sequence to identify partially overlapping, in antisense orientation, target mRNA protein-coding sequences.

FIG. 23A shows a schematic representation of how the sequence at the 5' of an IRES sequence and within an IRES-containing cellular mRNA can be considered as Binding Domain and FIG. 23B shows functional nucleic acid sequence elements within cMYC mRNA reference sequence (NM 002467).

FIG. 23C shows the results of the bioinformatics analysis (BLAST) using the c-MYC mRNA as query sequence to identify partially overlapping, in antisense orientation, target mRNA protein-coding sequences. In the table, annotated gene ENSEMBL nomenclature, Gene Name and Gene pairing region are indicated. The IRES-derived Binding Domain can overlap, in antisense orientation, to target mRNA in the 5' UTR, first exon, internal exon and with different pairing length, ranging from 18 to 198.

Figure 24:
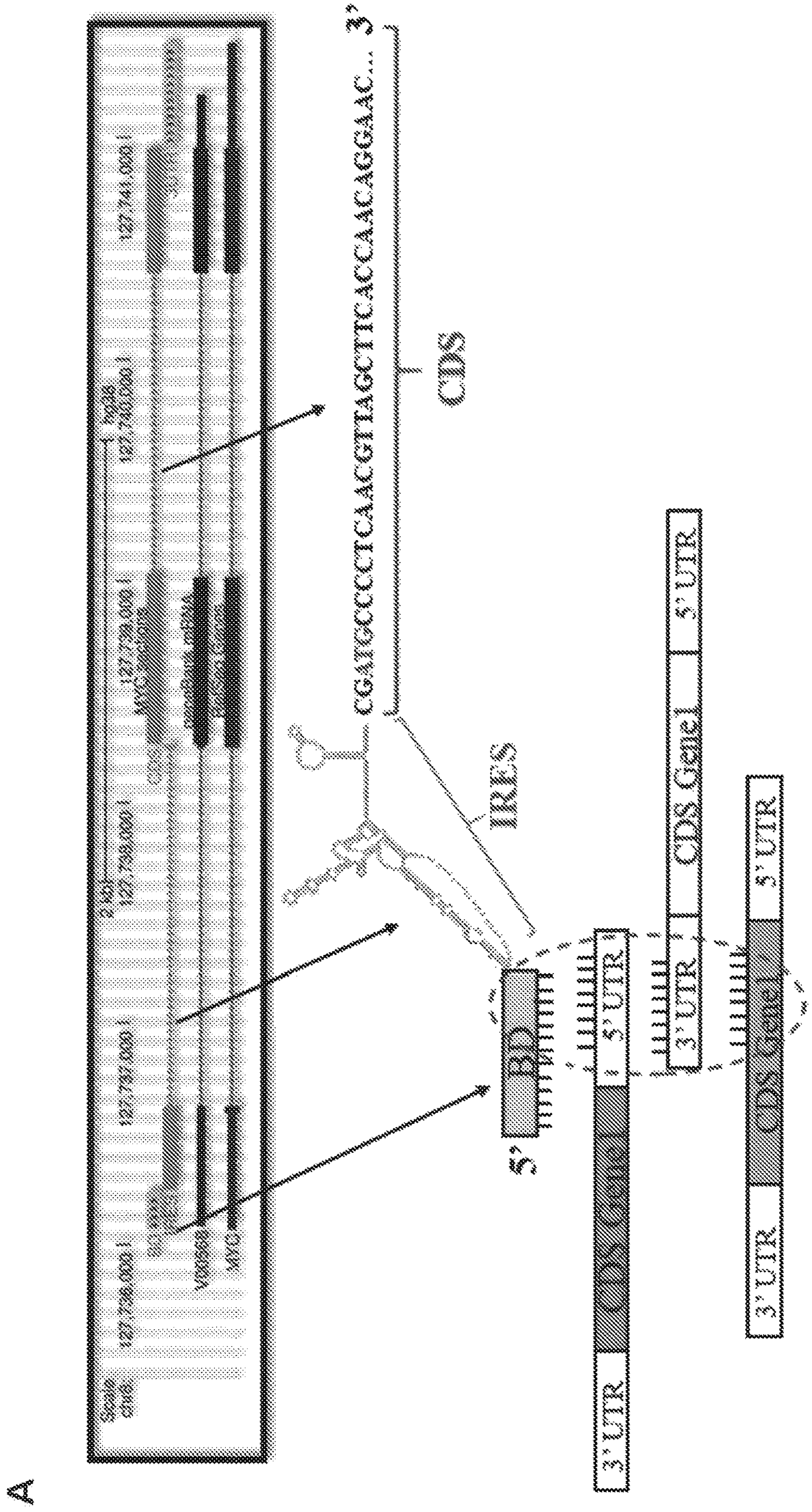
FIG. 24A shows a schematic representation of a mammalian expression plasmid encoding for full-length mRNA of MYC (cMYC-FL).
FIG. 24B shows Western blots carried out on lysates of mammalian SAGS cells with anti-JAG2, anti-DYRK2, anti-LYS, anti-UBE3A, anti-NRF1 antibodies.
FIGS. 24C and 24D show results of qRT-PCR to quantify expression of endogenous JAG2, DYRK2, LIS1, UBE3A, NRF1 and cMYC mRNAs.
FIG. 24E shows average cMyc full-length mRNA levels.
Figure 24:
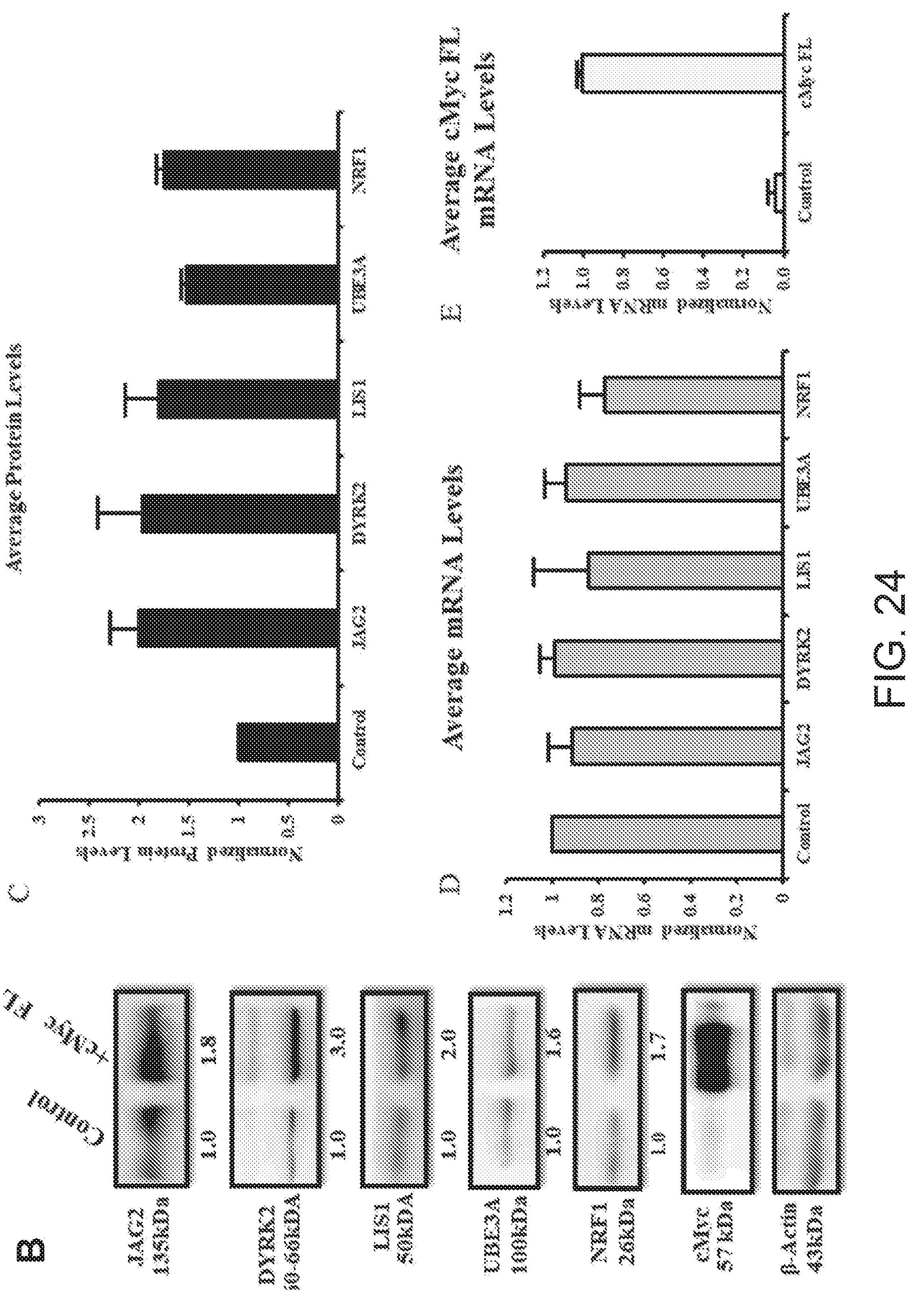

Mammalian SAGS cells were transfected with a mammalian expression plasmid encoding for full-length mRNA of MYC (cMYC-FL) (FIG. 24A). Control cells were transfected with an empty vector plasmid (control). 48 hours after transfection, cells were lysed and processed for protein quantities. Western blot (FIG. 24B) was performed with anti-JAG2, anti-DYRK2, anti-LYS, anti-UBE3A, anti-NRF1 antibodies as indicated. β-actin was used as loading control. Anti-cMYC antibody was used as additional control to verify expression of cMYC protein after transfection. Fold-induction was calculated on Western blot images normalized to β-actin and relative to empty control samples (C). Potency of cMYC IRES-containing functional nucleic acid molecules was evident for all tested target mRNAs, with binding domains ranging from 144 (JAG2) to 20 (UBE3A, NRF1) nucleotides in length.

RNA was purified from transfected cells. Expression of endogenous JAG2, DYRK2, LIS1, UBE3A, NRF1 and cMYC mRNAs was monitored by qRT-PCR using specific primers (FIG. 24C and FIG. 24D).

This example shows that the pairing region between the Binding Domain of an IRES-containing functional nucleic acid molecule and the target protein-coding mRNA can vary in position and in length, retaining its full translation enhancement activity.

Example 21

This example shows that the protein-coding CDS portion and the DNA-binding domain of cMYC are not required for the IRES-containing functional nucleic acid molecule to increase translation of partially-overlapping protein-coding mRNAs.

Figure 25:
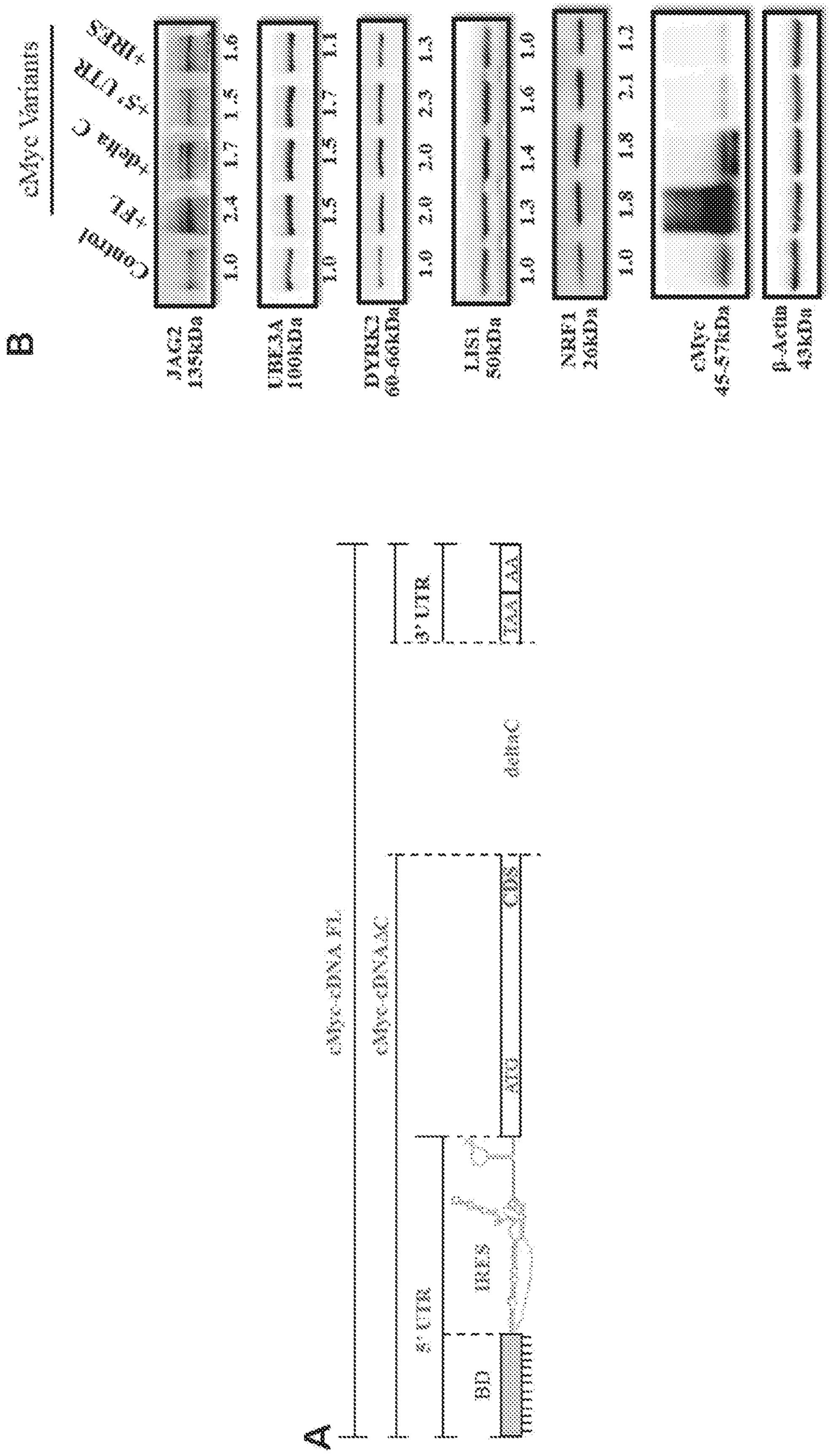
FIG. 25A shows a schematic representation of a mammalian expression plasmid encoding for full-length mRNA of MYC (cMYC-FL) or variants that lack cMYC DNA binding domain (deltaC) and are comprised of the 5'UTR only (5'UTR) or of the IRES only (IRES) domains.
FIG. 25B shows Western blots carried out on lysates of mammalian SAGS cells with anti-JAG2, anti-DYRK2, anti-LYS, anti-UBE3A, anti-NRF1 antibodies.
FIG. 25C shows results of qRT-PCR to quantify expression of endogenous JAG2, DYRK2, LIS1, UBE3A, NRF1 and cMYC mRNAs.
Figure 25:
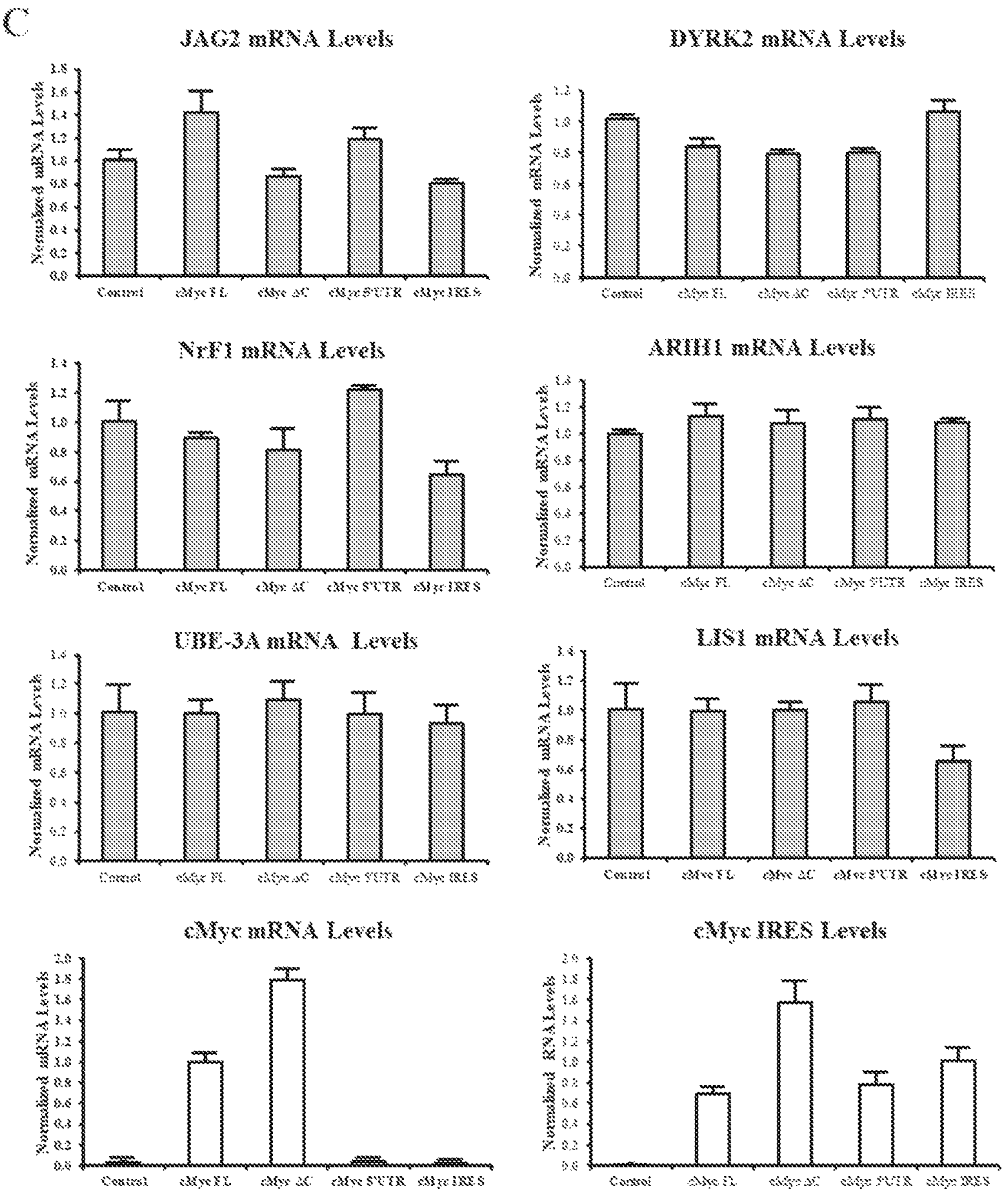

Mammalian SAGS cells were transfected with a mammalian expression plasmid encoding for full-length mRNA of MYC (cMYC-FL) or variants that lack cMYC DNA binding domain (deltaC) and are comprised of the 5'UTR only (5'UTR) or of the IRES only (IRES) domains. (FIG. 25A). Control cells were transfected with an empty vector plasmid (control). 48 hours after transfection, cells were lysed and processed for protein quantities. Western blot (FIG. 25B) was performed with anti-JAG2, anti-DYRK2, anti-LYS, anti-UBE3A, anti-NRF1 antibodies as indicated. β-actin was used as loading control. Anti-cMYC antibody was used as additional control to verify expression of cMYC protein after transfection. Fold-induction was calculated on Western blot images normalized to β-actin and relative to empty control samples. Fold-changes of protein quantities relative to control cells are indicated at the bottom of the western blot images.

RNA was purified from transfected cells. Expression of endogenous JAG2, DYRK2, LIS1, UBE3A, NRF1 and cMYC mRNAs was monitored by qRT-PCR using specific primers (FIG. 25C), proving the post-transcriptional mechanism of the IRES-containing functional nucleic acid molecule.

Advantages

The trans-acting functional nucleic acid molecule of the present invention allows to enhance the translation of virtually any target mRNA sequence without affecting target mRNA levels.

Figure 15:
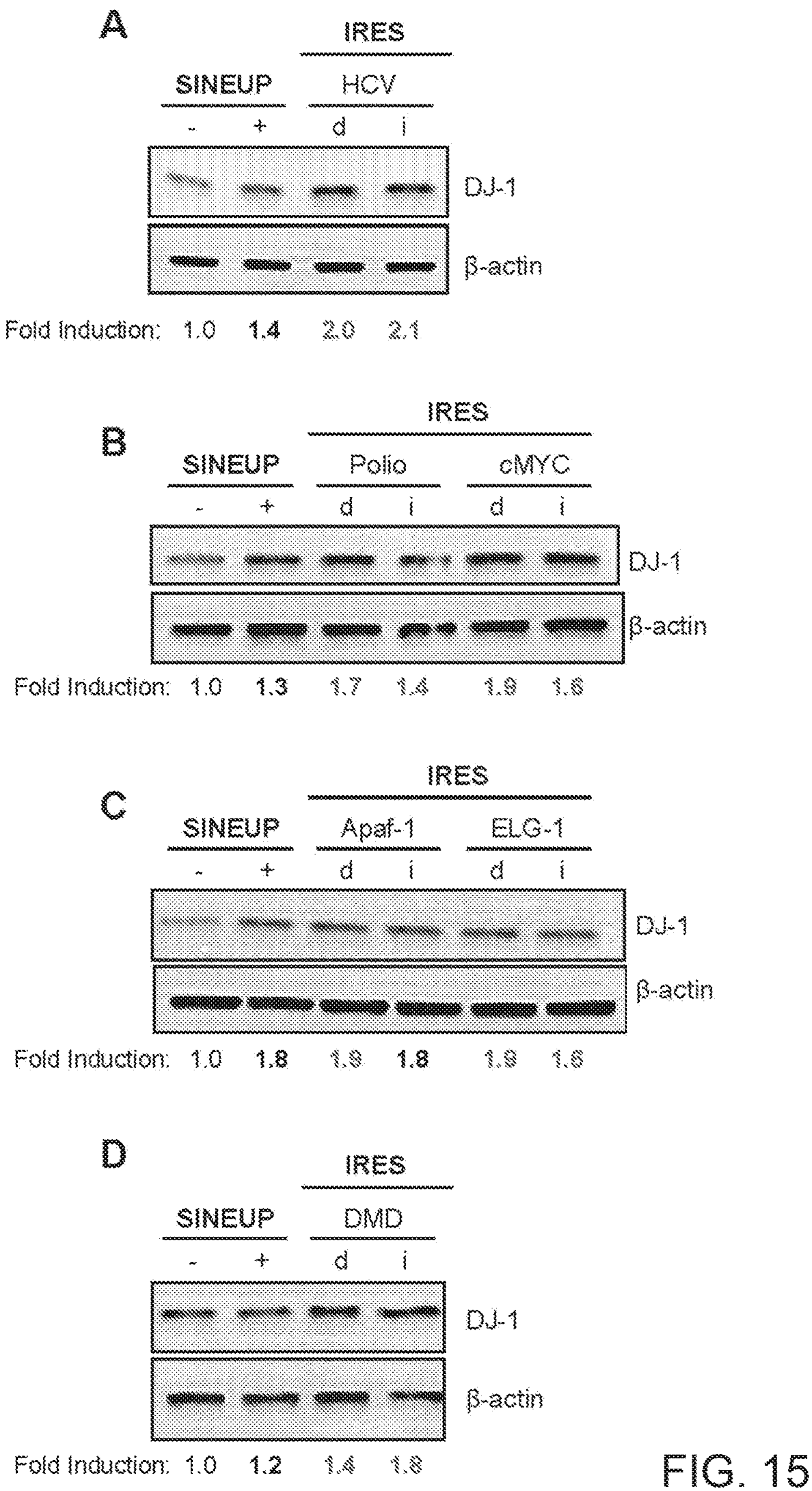
FIG. 15A-15D show the results of Western blots carried out on lysates of human hepatocellular carcinoma (HepG2) cells transfected respectively with empty control plasmid, SINEUP-DJ-1, an IRUP including an HCV IRES sequence in direct (d) or inverted (i) orientation, a Polio and cMYC IRES sequence in direct (d) or inverted (i) orientation, an Apaf-1 and ELG-1 IRES sequence in direct (d) or inverted (i) orientation, and a DMD IRES sequence in direct (d) or inverted (i) orientation.

With respect to the functional nucleic acid molecules disclosed in EP 2691522, those of the present invention avoid the risk of retrotransposition due to mouse SINE sequences and promote higher levels of enhancement of protein translation, as shown in Examples 2 to 11 in HEK 293T/17 and in Example 12 in HepG2 cells. In particular, examples of the more potent IRES sequences are given in FIG. 5 (HCV IRES, direct), in FIG. 6 (Polio IRES, direct and inverted), FIG. 7 (ECMV IRES, direct and inverted; CrPV IRES, direct and inverted), FIG. 9 (Apaf1 IRES, direct), FIG. 10 (ELG-1 IRES, direct and inverted), FIG. 11 (cMYC IRES, direct), FIG. 12 (short cMYC IRES, direct), FIG. 12 (DMD IRES, direct and inverted) in HEK cells. In addition, examples of more potent IRES sequences are given also in HepG2 cells (FIG. 15).

Some IRES sequences are as short as 40 to 50 nucleotides. This allows the engineering of very short trans-acting functional nucleic acid molecules.

In addition, the trans-acting functional nucleic acid molecules of the invention can include a particularly short target binding sequence, in particular as compared to functional nucleic acid molecules disclosed in EP2691522.

Both the limited length of the regulatory sequence and the target binding sequence contribute to keeping the length of the molecule short while allowing an optimal targeting and protein synthesis enhancement. One of the main advantages of having a short molecule, is to overcome the difficulty in synthesizing RNAs longer than 100 nucleotides.

Another advantage of the trans-acting functional nucleic acid molecules of the invention is they have a modular structure, i.e. have an independent target binding domain and an independent effector domain.

The invention claimed is:

1. A trans-acting functional nucleic acid molecule comprising:

a target binding sequence comprising a sequence reverse complementary to a eukaryotic target mRNA sequence for which protein translation is to be enhanced; and a regulatory sequence comprising an internal ribosome entry site (IRES) sequence or an internal ribosome entry site (IRES) derived sequence and enhancing translation of the target mRNA sequence, wherein the regulatory sequence is located 3' of the target binding sequence.

2. The trans-acting functional nucleic acid molecule according to claim 1, wherein the target binding sequence consists, from 3' to 5', of a sequence reverse complementary to 1 to 50 nucleotides of the 5' untranslated region (5' UTR) and 1 to 40 nucleotides of the coding sequence (CDS) of the target mRNA sequence.

3. The trans-acting functional nucleic acid molecule according to claim 2, wherein the target binding sequence consists, from 3' to 5', of a sequence reverse complementary to 10 to 45 nucleotides of the 5' untranslated region (5' UTR) and 2 to 6 nucleotides of the coding sequence (CDS) of the target mRNA sequence.

4. The trans-acting functional nucleic acid molecule according to claim 1, wherein the IRES sequence or IRES derived sequence is oriented, in the trans-acting functional nucleic acid molecule, in direct orientation relative to the 5' to 3' orientation of the functional nucleic acid molecule.

5. The trans-acting functional nucleic acid molecule according to claim 1, wherein the IRES sequence or IRES derived sequence is a sequence with 75% homology to a sequence selected from the group consisting of SEQ ID NO:36 to SEQ ID NO:65.

6. The trans-acting functional nucleic acid molecule according to claim 5, wherein the IRES sequence or IRES derived sequence is a sequence with 90% homology to a sequence selected from the group consisting of SEQ ID NO:36 to SEQ ID NO:65.

7. The trans-acting functional nucleic acid molecule according to claim 6, wherein the IRES sequence or IRES derived sequence is a sequence selected from the group consisting of SEQ ID NO:36 to SEQ ID NO:65.

8. The trans-acting functional nucleic acid molecule according to claim 1, wherein the trans-acting functional nucleic acid molecule is an RNA molecule or a modified RNA molecule.

9. The trans-acting functional nucleic acid molecule according to claim 1, further comprising a spacer sequence between the target binding sequence and the regulatory sequence.

10. A DNA molecule encoding the trans-acting functional nucleic acid molecule according to claim 1.

11. An expression vector comprising the DNA molecule according to claim 10.

12. A method for enhancing protein translation, the method comprising transfecting into a cell (a) the trans-acting functional nucleic acid molecule according to claim 1, (b) a DNA molecule encoding the trans-acting functional nucleic acid molecule according to claim 1, or (c) an expression vector comprising a DNA molecule encoding the trans-acting functional nucleic acid molecule according to claim 1.

13. A composition comprising (a) the trans-acting functional nucleic acid molecule according to claim 1, (b) a DNA molecule encoding the trans-acting functional nucleic acid molecule according to claim 1, or (c) an expression vector comprising a DNA molecule encoding the trans-acting functional nucleic acid molecule according to claim 1.

14. A method for enhancing translation of a target mRNA sequence, the method comprising hybridizing the target mRNA sequence to (a) the trans-acting functional nucleic acid molecule according to claim 1, (b) a DNA molecule encoding the trans-acting functional nucleic acid molecule according to claim 1, or (c) an expression vector comprising a DNA molecule encoding the trans-acting functional nucleic acid molecule according to claim 1.

15. A method for treating a genetic disease caused by down-regulation of a protein-coding mRNA, the method comprising administering (a) the trans-acting functional nucleic acid molecule according to claim 1, (b) a DNA molecule encoding the trans-acting functional nucleic acid molecule according to claim 1, or (c) an expression vector comprising a DNA molecule encoding the trans-acting functional nucleic acid molecule according to claim 1.

16. A method for treating a genetic or sporadic disease where reduced gene dosage is detrimental, the method comprising administering (a) the trans-acting functional nucleic acid molecule according to claim 1, (b) a DNA molecule encoding the trans-acting functional nucleic acid molecule according to claim 1, or (c) an expression vector comprising a DNA molecule encoding the trans-acting functional nucleic acid molecule according to claim 1.

* * * * *

SEQUENCE LISTING

<160> NUMBER OF SEQ ID NOS: 65

<210> SEQ ID NO 1
<211> LENGTH: 1437
<212> TYPE: RNA
<213> ORGANISM: Artificial Sequence
<220> FEATURE:
<223> OTHER INFORMATION: HCV(d) IRUP

<400> SEQUENCE: 1

```
ccauuuuuau guuauauguu uacaagcccc acaccaggcu gaaaaucugc agaauucgcc      60

cuugccagcc cccugauggg ggcgacacuc caccaugaau cacuccccug ugaggaacua     120

cugucuucac gcagaaagcg ucuagccaug gcguuaguau gagugucgug cagccuccag     180

gaccccccu cccgggagag ccauaguggu cugcggaacc ggugaguaca ccggaauugc     240

caggacgacc ggguccuuuc uuggauaaac ccgcucaaug ccuggagauu ugggcgugcc     300

cccgcaagac ugcuagccga guaguguugg gucgcgaaag gccuuguggu acugccugau     360

agggugcuug cgagugcccc gggaggucuc guagaccgug caccaugagc acgaauccua     420

aaccucaaag aaaaaccaaa cguaacaguc ucuuaaaaaa caaacaaacg aacgaacagc     480

aagggagcug gguaugacaa cacauacuau aauucuagua cucaggaugc ugaaacagga     540

ggauugccug acugggagau auaaggagaa ucuguuguca cccccacccc uccccauaaa     600

ggcagaauaa aagaacgucc uauaaacaaa uaaacaaaca acccaauaaa acaaaaccaa     660

gaucucucca ccuuuucuuu gcuuuuucag acuuuguaau aaggcccuuu ggagugcagg     720

auauucggca ggacaagcag agagggagac caucaguucu uucuuugauc aagaagacua     780

uguuccuuag caaacuggug uguauuaucu cuuaugcaau gagccuggaa agagggcaca     840

gccaccgagg augguacagc auggauggau gguacgcuac agagacucgg gagcccaacu     900

gugaguggcu gacuggcaug guagguucag ggaagaauug gccugugaag aaaauguucu     960

ugaaaaguga acaaggugca ggagguagga gugggguccug ggcaaagcag ggggugcauc    1020

ccagccucag ggaauagcac agcagagguc uguugaugca ugcgagugca ugaccugcuu    1080

gccaauagac gaucaagaau gggcaaagca ucauggguga ugagugggag aggggaugag    1140

acauuccuuu cucccugcug agacuuccau ugaaccgaug aguucugaau agaagaugcc    1200

cccccacccc cccaccagug uagaaucuga agggaggcau auauuacccu auauuacucu    1260

guguuggcgg cgagcuaucu gacagccaac cuucccauac auuucauugg gcauacacua    1320

augacaggaa guuccuuuug cuuguaugca agagauggcu cacacgaugg agaauuuaau    1380

cuugaagggc gaauuccacc acacuggacu aguggauccg agcucgguac caagcuu        1437
```

<210> SEQ ID NO 2
<211> LENGTH: 1437
<212> TYPE: RNA
<213> ORGANISM: Artificial Sequence
<220> FEATURE:
<223> OTHER INFORMATION: HCV(i) IRUP

<400> SEQUENCE: 2

```
ccauuuuuau guuauauguu uacaagcccc acaccaggcu gaaaaucugc agaauucgcc      60

cuuguuacgu uugguuuuuc uuugagguuu aggauucgug cucauggugc acggucuacg     120
```

-continued agaccucccg gggcacucgc aagcacccua ucaggcagua ccacaaggcc uuucgcgacc 180
caacacuacu cggcuagcag ucuugcgggg gcacgcccaa aucuccaggc auugagcggg 240
uuuauccaag aaaggacccg gucguccugg caauuccggu guacucaccg guuccgcaga 300
ccacuauggc ucucccggga gggggggucc uggaggcugc acgacacuca uacuaacgcc 360
auggcuagac gcuuucugcg ugaagacagu aguuccucac aggggaguga uucauggugg 420
agugucgccc ccaucagggg gcuggcaguc ucuuaaaaaa caaacaaacg aacgaacagc 480
aagggagcug gguaugacaa cacauacuau aauucuagua cucaggaugc ugaaacagga 540
ggauugccug acugggagau auaaggagaa ucuguuguca cccccacccc uccccauaaa 600
ggcagaauaa aagaacgucc uauaaacaaa uaaacaaaca acccaauaaa acaaaaccaa 660
gaucucucca ccuuuucuuu gcuuuuucag acuuuguaau aaggcccuuu ggagugcagg 720
auauucggca ggacaagcag agagggagac caucaguucu uucuuugauc aagaagacua 780
uguuccuuag caaacuggug uguauuaucu cuuaugcaau gagccuggaa agagggcaca 840
gccaccgagg augguacagc auggauggau gguacgcuac agagacucgg gagcccaacu 900
gugaguggcu gacuggcaug guagguucag ggaagaauug gccugugaag aaaauguucu 960
ugaaaaguga acaaggugca ggagguagga gugggguccug ggcaaagcag ggggugcauc 1020
ccagccucag ggaauagcac agcagagguc uguugaugca ugcgagugca ugaccugcuu 1080
gccaauagac gaucaagaau gggcaaagca ucaugggguga ugagugggag aggggaugag 1140
acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 3
<211> LENGTH: 1366
<212> TYPE: RNA
<213> ORGANISM: Artificial Sequence
<220> FEATURE:
<223> OTHER INFORMATION: Polio(d) IRUP

<400> SEQUENCE: 3
ccauuuuuau guuauauguu uacaagcccc acaccaggcu gaaaaucugc agaauucgcc 60
cuuaugaguc uggacauccc ucaccgguga cgguggucca ggcugcguug gcggccuacc 120
uauggcuaac gccaugggac gcuaguugug aacaaggugu gaagagccua uugagcuaca 180
uaagaauccu ccggccccug aaugcggcua aucccaaccu cggagcaggu ggucacaaac 240
cagugauugg ccugucguaa cgcgcaaguc cguggcggaa ccgacuacuu ugggugnccg 300
uguuuccuuu uauuuuauug uggcugcuua uggugacaau cacagauugu uaucauaaag 360
cgaauuggau uggccagucu cuuaaaaaac aaacaaacga acgaacagca agggagcugg 420
guaugacaac acauacuaua auucuaguac ucaggaugcu gaaacaggag gauugccuga 480
cugggagaua uaaggagaau cuguugucac ccccaccccu ccccauaaag gcagaauaaa 540
agaacguccu auaaacaaau aaacaaacaa cccaauaaaa caaaaccaag aucucuccac 600
cuuuucuuug cuuuuucaga cuuuguaaua aggcccuuug gagugcagga uauucggcag 660
gacaagcaga gagggagacc aucaguucuu ucuuugauca agaagacuau guuccuuagc 720

-continued

```
aaacuggugu guauuaucuc uuaugcaaug agccuggaaa gagggcacag ccaccgagga    780

ugguacagca uggauggaug guacgcuaca gagacucggg agcccaacug ugaguggcug    840

acuggcaugg uagguucagg gaagaauugg ccugugaaga aaauguucuu gaaaagugaa    900

caaggugcag gagguaggag ugggguccugg gcaaagcagg gggugcaucc cagccucagg   960

gaauagcaca gcagaggucu guugaugcau gcgagugcau gaccugcuug ccaauagacg   1020

aucaagaaug ggcaaagcau caugggugau gagugggaga ggggaugaga cauucccuuuc  1080

ucccugcuga gacuuccauu gaaccgauga guucugaaua gaagaugccc ccccaccccc   1140

ccaccagugu agaaucugaa gggaggcaua uauuacccua uauuacucug uguuggcggc   1200

gagcuaucug acagccaacc uucccauaca uuucauuggg cauacacuaa ugacaggaag   1260

uuccuuuugc uuguaugcaa gagauggcuc acacgaugga gaauuuaauc uugaagggcg   1320

aauuccacca cacuggacua guggauccga gcucgguacc aagcuu                  1366
```

<210> SEQ ID NO 4
<211> LENGTH: 1366
<212> TYPE: RNA
<213> ORGANISM: Artificial Sequence
<220> FEATURE:
<223> OTHER INFORMATION: Polio(i) IRUP

<400> SEQUENCE: 4

```
ccauuuuuau guuauauguu uacaagcccc acaccaggcu gaaaaucugc agaauucgcc     60

cuuggccaau ccaauucgcu uuaugauaac aaucugugau ugucaccaua agcagccaca    120

auaaaauaaa aggaaacacg gacacccaaa guagucgguu ccgccacgga cuugcgcguu    180

acgacaggcc aaucacuggu uugugaccac cugcuccgag guugggauua gccgcauuca    240

ggggccggag gauucuuaug uagcucaaua ggcucuucac accuuguuca caacuagcgu    300

cccauggcgu uagccauagg uaggccgcca acgcagccug gaccaccguc accggugagg    360

gauguccaga cucauagucu cuuaaaaaac aaacaaacga acgaacagca agggagcugg    420

guaugacaac acauacuaua auucuaguac ucaggaugcu gaaacaggag gauugccuga    480

cugggagaua uaaggagaau cuguugucac ccccaccccu ccccauaaag gcagaauaaa    540

agaacguccu auaaacaaau aaacaaacaa cccaauaaaa caaaaccaag aucucuccac    600

cuuuucuuug cuuuuucaga cuuuguaaua aggcccuuug gagugcagga uauucggcag    660

gacaagcaga gagggagacc aucaguucuu ucuuugauca agaagacuau guuccuuagc    720

aaacuggugu guauuaucuc uuaugcaaug agccuggaaa gagggcacag ccaccgagga    780

ugguacagca uggauggaug guacgcuaca gagacucggg agcccaacug ugaguggcug    840

acuggcaugg uagguucagg gaagaauugg ccugugaaga aaauguucuu gaaaagugaa    900

caaggugcag gagguaggag ugggguccugg gcaaagcagg gggugcaucc cagccucagg   960

gaauagcaca gcagaggucu guugaugcau gcgagugcau gaccugcuug ccaauagacg   1020

aucaagaaug ggcaaagcau caugggugau gagugggaga ggggaugaga cauucccuuuc  1080

ucccugcuga gacuuccauu gaaccgauga guucugaaua gaagaugccc ccccaccccc   1140

ccaccagugu agaaucugaa gggaggcaua uauuacccua uauuacucug uguuggcggc   1200

gagcuaucug acagccaacc uucccauaca uuucauuggg cauacacuaa ugacaggaag   1260

uuccuuuugc uuguaugcaa gagauggcuc acacgaugga gaauuuaauc uugaagggcg   1320

aauuccacca cacuggacua guggauccga gcucgguacc aagcuu                  1366
```

-continued

<210> SEQ ID NO 5
<211> LENGTH: 1630
<212> TYPE: RNA
<213> ORGANISM: Artificial Sequence
<220> FEATURE:
<223> OTHER INFORMATION: EMCV(d) IRUP

<400> SEQUENCE: 5
ccauuuuuau guuauauguu uacaagcccc acaccaggcu gaaaaucugc agaauucgcc 60
cuuccccccc ucucccuccc cccccccuaa cguuacuggc cgaagccgcu uggaauaagg 120
ccggugugcg uuugucuaua uguuauuuuc caccauauug ccgucuuuug gcaaugugag 180
ggcccggaaa ccuggcccug ucuucuugac gagcauuccu aggggucuuu ccccucucgc 240
caaaggaaug caaggucugu ugaaugucgu gaaggaagca guuccucugg aagcuucuug 300
aagacaaaca acgucuguag cgacccuuug caggcagcgg aaccccccac cuggcgacag 360
gugccucugc ggccaaaagc cacguguaua agauacaccu gcaaaggcgg cacaacccca 420
gugccacguu gugaguugga uaguugugga aagagucaaa uggcucuccu caagcguauu 480
caacaagggg cugaaggaug cccagaaggu accccauugu augggaucug aucuggggcc 540
ucggugcaca ugcuuuacau guguuuaguc gagguuaaaa aacgucuagg ccccccgaac 600
cacggggacg ugguuuuccu uugaaaaaca cgaugauaaa gucucuuaaa aaacaaacaa 660
acgaacgaac agcaagggag cuggguauga caacacauac uauaauucua guacucagga 720
ugcugaaaca ggaggauugc cugacuggga gauauaagga gaaucuguug ucacccccac 780
cccuccccau aaaggcagaa uaaaagaacg uccuauaaac aaauaaacaa acaacccaau 840
aaaacaaaac caagaucucu ccaccuuuuc uuugcuuuuu cagacuuugu aauaaggccc 900
uuuggagugc aggauauucg gcaggacaag cagagaggga gaccaucagu ucuuucuuug 960
aucaagaaga cuauguuccu uagcaaacug guguguauua ucucuuaugc aaugagccug 1020
gaaagagggc acagccaccg aggaugguac agcauggaug gaugguacgc uacagagacu 1080
cgggagccca acugugagug gcugacuggc augguagguu cagggaagaa uuggccugug 1140
aagaaaaugu ucuugaaaag ugaacaaggu gcaggaggua ggaguggguc cugggcaaag 1200
cagggggugc aucccagccu cagggaauag cacagcagag gucuguugau gcaugcgagu 1260
gcaugaccug cuugccaaua gacgaucaag aaugggcaaa gcaucauggg ugaugagugg 1320
gagaggggau gagacauucc uuucucccug cugagacuuc cauugaaccg augaguucug 1380
aauagaagau gcccccccac ccccccacca guguagaauc ugaagggagg cauauauuac 1440
ccuauauuac ucuguguugg cggcgagcua ucugacagcc aaccuuccca uacauuucau 1500
ugggcauaca cuaaugacag gaaguuccuu uugcuuguau gcaagagaug gcucacacga 1560
uggagaauuu aaucuugaag ggcgaauucc accacacugg acuaguggau ccgagcucgg 1620
uaccaagcuu 1630

<210> SEQ ID NO 6
<211> LENGTH: 1630
<212> TYPE: RNA
<213> ORGANISM: Artificial Sequence
<220> FEATURE:
<223> OTHER INFORMATION: EMCV(i) IRUP

<400> SEQUENCE: 6
ccauuuuuau guuauauguu uacaagcccc acaccaggcu gaaaaucugc agaauucgcc 60
cuuuuaucau cguguuuuuc aaaggaaaac cacguccccg ugguucgggg ggccuagacg 120

-continued uuuuuuaacc ucgacuaaac acauguaaag caugugcacc gaggccccag aucagauccc 180
auacaauggg guaccuucug ggcauccuuc agccccuugu ugaauacgcu ugaggagagc 240
cauuugacuc uuuccacaac uauccaacuc acaacguggc acuggggiuug ugccgccuuu 300 gcagguguau cuuauacacg uggcuuuugg ccgcagaggc accugucgcc aggugggggg 360
uuccgcugcc ugcaaagggu cgcuacagac guuguuuguc uucaagaagc uuccagagga 420
acugcuuccu ucacgacauu caacagaccu ugcauuccuu uggcgagagg ggaaagaccc 480
cuaggaaugc ucgucaagaa gacagggcca gguuuccggg cccucacauu gccaaaagac 540
ggcaauaugg uggaaaauaa cauauagaca aacgcacacc ggccuuauuc caagcggcuu 600
cggccaguaa cguuaggggg gggggaggga gagggggga gucucuuaaa aaacaaacaa 660
acgaacgaac agcaagggag cuggguauga caacacauac uauaauucua guacucagga 720
ugcugaaaca ggaggauugc cugacuggga gauauaagga gaaucuguug ucacccccac 780
cccuccccau aaaggcagaa uaaaagaacg uccuauaaac aaauaaacaa acaacccaau 840
aaaacaaaac caagaucucu ccaccuuuuc uuugcuuuuu cagacuuugu aauaaggccc 900
uuuggagugc aggauauucg gcaggacaag cagagaggga gaccaucagu ucuuucuuug 960
aucaagaaga cuauguuccu uagcaaacug guguguauua ucucuuaugc aaugagccug 1020
gaaagagggc acagccaccg aggaugguac agcauggaug gaugguacgc uacagagacu 1080
cgggagccca acugugagug gcugacuggc augguagguu cagggaagaa uuggccugug 1140
aagaaaaugu ucuugaaaag ugaacaaggu gcaggaggua ggagugggguc cugggcaaag 1200 caggggggugc aucccagccu cagggaauag cacagcagag gucuguugau gcaugcgagu 1260
gcaugaccug cuugccaaua gacgaucaag aaugggcaaa gcaucauggg ugaugagugg 1320
gagaggggau gagacauucc uuucucccug cugagacuuc cauugaaccg augaguucug 1380
aauagaagau gcccccccac ccccccacca guguagaauc ugaagggagg cauauauuac 1440
ccuauauuac ucuguguugg cggcgagcua ucugacagcc aaccuuccca uacauuucau 1500
ugggcauaca cuaaugacag gaaguuccuu uugcuuguau gcaagagaug gcucacacga 1560
uggagaauuu aaucuugaag ggcgaauucc accacacugg acuaguggau ccgagcucgg 1620
uaccaagcuu 1630

<210> SEQ ID NO 7
<211> LENGTH: 1140
<212> TYPE: RNA
<213> ORGANISM: Artificial Sequence
<220> FEATURE:
<223> OTHER INFORMATION: CrPV(d) IRUP

<400> SEQUENCE: 7
ccauuuuuau guuauauguu uacaagcccc acaccaggcu gaaaaucugc agaauucgcc 60
cuuaaagcaa aaaugugauc uugcuuguaa auacaauuuu gagagguuaa uaaauuacaa 120
guagugcuau uuuuguauuu agguuagcua uuuagcuuua cguuccagga ugccuagugg 180
cagccccaca auauccagga agcccucucu gcgguuuuuc agauuaggua gucgaaaaac 240
cuaagaaauu uaccuagucu cuuaaaaaac aaacaaacga acgaacagca agggagcugg 300
guaugacaac acauacuaua auucuaguac ucaggaugcu gaaacaggag gauugccuga 360
cugggagaua uaaggagaau cuguugucac ccccaccccu ccccauaaag gcagaauaaa 420
agaacguccu auaaacaaau aaacaaacaa cccaauaaaa caaaaccaag aucucuccac 480
cuuuucuuug cuuuuucaga cuuuguaaua aggcccuuug gagugcagga uauucggcag 540

```
gacaagcaga gagggagacc aucaguucuu ucuuugauca agaagacuau guuccuuagc    600

aaacuggugu guauuaucuc uuaugcaaug agccuggaaa gagggcacag ccaccgagga    660

ugguacagca uggauggaug guacgcuaca gagacucggg agcccaacug ugaguggcug    720

acuggcaugg uagguucagg gaagaauugg ccugugaaga aaauguucuu gaaaagugaa    780

caaggugcag gagguaggag ugggguccugg gcaaagcagg gggugcaucc cagccucagg    840

gaauagcaca gcagaggucu guugaugcau gcgagugcau gaccugcuug ccaauagacg    900

aucaagaaug ggcaaagcau caugggugau gagugggaga ggggaugaga cauuccuuuc    960

ucccugcuga gacuuccauu gaaccgauga guucugaaua gaagaugccc ccccaccccc   1020

ccaccagugu agaaucugaa gggaggcaua uauuacccua uauuacucug uguuggcggc   1080

gagcuaucug acagccaacc uucccauaca uuucauuggg cauacacuaa ugacaggaag   1140
```

```
<210> SEQ ID NO 8
<211> LENGTH: 1246
<212> TYPE: RNA
<213> ORGANISM: Artificial Sequence
<220> FEATURE:
<223> OTHER INFORMATION: CrPV(i) IRUP

<400> SEQUENCE: 8

ccauuuuuau guuauauguu uacaagcccc acaccaggcu gaaaaucugc agaauucgcc     60

cuuagguaaa uuucuuaggu uuuucgacua ccuaaucuga aaaaccgcag agagggcuuc    120

cuggauauug uggggcugcc acuaggcauc cuggaacgua aagcuaaaua gcuaaccuaa    180

auacaaaaau agcacuacuu guaauuuauu aaccucucaa aauuguauuu acaagcaaga    240

ucacauuuuu gcuuuagucu cuuaaaaaac aaacaaacga acgaacagca agggagcugg    300

guaugacaac acauacuaua auucuaguac ucaggaugcu gaaacaggag gauugccuga    360

cugggagaua uaaggagaau cuguugucac ccccaccccu ccccauaaag gcagaauaaa    420

agaacguccu auaaacaaau aaacaaacaa cccaauaaaa caaaaccaag aucucuccac    480

cuuuucuuug cuuuuucaga cuuuguaaua aggcccuuug gagugcagga uauucggcag    540

gacaagcaga gagggagacc aucaguucuu ucuuugauca agaagacuau guuccuuagc    600

aaacuggugu guauuaucuc uuaugcaaug agccuggaaa gagggcacag ccaccgagga    660

ugguacagca uggauggaug guacgcuaca gagacucggg agcccaacug ugaguggcug    720

acuggcaugg uagguucagg gaagaauugg ccugugaaga aaauguucuu gaaaagugaa    780

caaggugcag gagguaggag ugggguccugg gcaaagcagg gggugcaucc cagccucagg    840

gaauagcaca gcagaggucu guugaugcau gcgagugcau gaccugcuug ccaauagacg    900

aucaagaaug ggcaaagcau caugggugau gagugggaga ggggaugaga cauuccuuuc    960

ucccugcuga gacuuccauu gaaccgauga guucugaaua gaagaugccc ccccaccccc   1020

ccaccagugu agaaucugaa gggaggcaua uauuacccua uauuacucug uguuggcggc   1080

gagcuaucug acagccaacc uucccauaca uuucauuggg cauacacuaa ugacaggaag   1140

uuccuuuugc uuguaugcaa gagauggcuc acacgaugga gaauuuaauc uugaagggcg   1200

aauuccacca cacuggacua guggauccga gcucgguacc aagcuu                  1246
```

```
<210> SEQ ID NO 9
<211> LENGTH: 1285
<212> TYPE: RNA
<213> ORGANISM: Artificial Sequence
<220> FEATURE:
```

<223> OTHER INFORMATION: Apaf-1(d) IRUP

<400> SEQUENCE: 9
ccauuuuuau guuauauguu uacaagcccc acaccaggcu gaaaaucugc agaauucgcc 60
cuucagagau ccaggggagg cgccugugag gcccggaccu gccccggggc gaaggguaug 120
uggcgagaca gagcccugca ccccuaauuc ccgguggaaa acuccuguug ccguuucccu 180
ccaccggccu ggagucuccc agucuugucc cggcagugcc gcccuccccca cuaagaccua 240 ggcgcaaagg cuuggcucau gguugacagc ucagagagag aaagaucuga gggaagucuc 300
uuaaaaaaca aacaaacgaa cgaacagcaa gggagcuggg uaugacaaca cauacuauaa 360
uucuaguacu caggaugcug aaacaggagg auugccugac ugggagauau aaggagaauc 420
uguugucacc cccaccccuc cccauaaagg cagaauaaaa gaacguccua uaaacaaaua 480
aacaaacaac ccaauaaaac aaaaccaaga ucucuccacc uuuucuuugc uuuuucagac 540
uuuguaauaa ggcccuuugg agugcaggau auucggcagg acaagcagag agggagacca 600
ucaguucuuu cuuugaucaa gaagacuaug uuccuuagca aacuggugug uauuaucucu 660
uaugcaauga gccuggaaag agggcacagc caccgaggau gguacagcau ggauggaugg 720
uacgcuacag agacucggga gcccaacugu gaguggcuga cuggcauggu agguucaggg 780
aagaauuggc cugugaagaa aauguucuug aaaagugaac aaggugcagg agguaggagu 840
ggguccuggg caaagcaggg ggugcauccc agccucaggg aauagcacag cagaggucug 900
uugaugcaug cgagugcaug accugcuugc caauagacga ucaagaaugg gcaaagcauc 960
augggugaug agugggagag gggaugagac auuccuuucu cccugcugag acuuccauug 1020
aaccgaugag uucugaauag aagaugcccc cccaccccc caccagugua gaaucugaag 1080
ggaggcauau auuacccuau auuacucugu guuggcggcg agcuaucuga cagccaaccu 1140
ucccauacau uucauugggc auacacuaau gacaggaagu uccuuuugcu uguaugcaag 1200
agauggcuca cacgauggag aauuuaaucu ugaagggcga auuccaccac acuggacuag 1260
uggauccgag cucgguacca agcuu 1285

<210> SEQ ID NO 10
<211> LENGTH: 1285
<212> TYPE: RNA
<213> ORGANISM: Artificial Sequence
<220> FEATURE:
<223> OTHER INFORMATION: Apaf-1(i) IRUP

<400> SEQUENCE: 10
ccauuuuuau guuauauguu uacaagcccc acaccaggcu gaaaaucugc agaauucgcc 60
cuuucccuca gaucuuucuc ucucugagcu gucaaccaug agccaagccu uugcgccuag 120
gucuuagugg ggagggcggc acugccggga caagacuggg agacuccagg ccgguggagg 180
gaaacggcaa caggaguuuu ccaccgggaa uuaggggugc agggcucugu cucgccacau 240
acccuucgcc ccggggcagg uccgggccuc acaggcgccu ccccuggauc ucugagucuc 300
uuaaaaaaca aacaaacgaa cgaacagcaa gggagcuggg uaugacaaca cauacuauaa 360
uucuaguacu caggaugcug aaacaggagg auugccugac ugggagauau aaggagaauc 420
uguugucacc cccaccccuc cccauaaagg cagaauaaaa gaacguccua uaaacaaaua 480
aacaaacaac ccaauaaaac aaaaccaaga ucucuccacc uuuucuuugc uuuuucagac 540
uuuguaauaa ggcccuuugg agugcaggau auucggcagg acaagcagag agggagacca 600
ucaguucuuu cuuugaucaa gaagacuaug uuccuuagca aacuggugug uauuaucucu 660

-continued

```
uaugcaauga gccuggaaag agggcacagc caccgaggau gguacagcau ggauggaugg    720

uacgcuacag agacucggga gcccaacugu gaguggcuga cuggcauggu agguucaggg    780

aagaauuggc cugugaagaa aauguucuug aaaagugaac aaggugcagg agguaggagu    840

ggguccuggg caaagcaggg ggugcauccc agccucaggg aauagcacag cagaggucug    900

uugaugcaug cgagugcaug accugcuugc caauagacga ucaagaaugg gcaaagcauc    960

augggugaug agugggagag gggaugagac auuccuuucu cccugcugag acuuccauug   1020

aaccgaugag uucugaauag aagaugcccc cccaccccccc caccagugua gaaucugaag   1080

ggaggcauau auuacccuau auuacucugu guuggcggcg agcuaucuga cagccaaccu   1140

ucccauacau uucauugggc auacacuaau gacaggaagu uccuuuugcu uguaugcaag   1200

agauggcuca cacgauggag aauuuaaucu ugaagggcga auuccaccac acuggacuag   1260

uggauccgag cucgguacca agcuu                                          1285


<210> SEQ ID NO 11
<211> LENGTH: 1514
<212> TYPE: RNA
<213> ORGANISM: Artificial Sequence
<220> FEATURE:
<223> OTHER INFORMATION: ELG-1(d) IRUP

<400> SEQUENCE: 11

ccauuuuuau guuauauguu uacaagcccc acaccaggcu gaaaaucugc agaauucgcc     60

cuuacuuuug gugggcauuu aaaaaugugu guguaugugu auauauguau guguauguau    120

guguauauau guauauguau guauguaucg cguguaugug uguauguaug cauguguaug    180

uauguauaug cauguaugug uauguguaua uauguaugug uguguaugua uaugugugug    240

uauguguaug ugugugugua ugugugugug uauguaugua uguauguaua uguauuauac    300

acauauacac auauugguuu uuuuaaucau uugagaguua guugaagaua aaaacccauc    360

accccuaaau guauuccaaa gaauaagaac auuguuuuau acauagcaca cuuaacaaaa    420

ucaagaaauu uaacauuaau acaguacugu uaccuaaucc guagucgauu uucaaauuuu    480

gucaguuguu ccaauaaugu ccuuuauaua uuccccgccc agcagucucu uaaaaaaacaa    540

acaaacgaac gaacagcaag ggagcugggu augacaacac auacuauaau ucuaguacuc    600

aggaugcuga aacaggagga uugccugacu gggagauaua aggagaaucu guugucaccc    660

ccaccccucc ccauaaaggc agaauaaaag aacguccuau aaacaaauaa acaaacaacc    720

caauaaaaca aaaccaagau cucuccaccu uuucuuugcu uuuucagacu uuguaauaag    780

gcccuuugga gugcaggaua uucggcagga caagcagaga gggagaccau caguucuuuc    840

uuugaucaag aagacuaugu uccuuagcaa acuggugugu auuaucucuu augcaaugag    900

ccuggaaaga gggcacagcc accgaggaug guacagcaug gauggauggu acgcuacaga    960

gacucgggag cccaacugug aguggcugac uggcauggua gguucaggga agaauuggcc   1020

ugugaagaaa auguucuuga aaagugaaca aggugcagga gguaggagug ggguccugggc   1080

aaagcagggg gugcauccca gccucaggga auagcacagc agaggucugu ugaugcaugc   1140

gagugcauga ccugcuugcc aauagacgau caagaauggg caaagcauca ugggugauga   1200

gugggagagg ggaugagaca uuccuuucuc ccugcugaga cuuccauuga accgaugagu   1260

ucugaauaga agaugccccc ccaccccccc accaguguag aaucugaagg gaggcauaua   1320

uuacccuaua uuacucugug uuggcggcga gcuaucugac agccaaccuu cccauacauu   1380
```

-continued

```
ucauugggca uacacuaaug acaggaaguu ccuuuugcuu guaugcaaga gauggcucac   1440

acgauggaga auuuaaucuu gaagggcgaa uuccaccaca cuggacuagu ggauccgagc   1500

ucgguaccaa gcuu                                                     1514
```

<210> SEQ ID NO 12
<211> LENGTH: 1514
<212> TYPE: RNA
<213> ORGANISM: Artificial Sequence
<220> FEATURE:
<223> OTHER INFORMATION: ELG-1(i) IRUP

<400> SEQUENCE: 12

```
ccauuuuuau guuauauguu uacaagcccc acaccaggcu gaaaaucugc agaauucgcc     60

cuugcugggc ggggaauaua uaaaggacau uauuggaaca acugacaaaa uuugaaaauc    120

gacuacggau uagguaacag uacuguauua auguuaaauu ucuugauuuu guuaagugug    180

cuauguauaa aacaauguuc uuauucuuug gaauacauuu aggggugaug gguuuuuauc    240

uucaacuaac ucucaaauga uuaaaaaaac caauaugugu auauguguau aauacauaua    300

cauacauaca uacauacaca cacacauaca cacacacaua cacauacaca cacauauaca    360

uacacacaca uacauauaua cacauacaca uacaugcaua uacauacaua cacaugcaua    420

cauacacaca uacacgcgau acauacauac auauacauau auacacauac auacacauac    480

auauauacac auacacacac auuuuuaaau gcccaccaaa aguagucucu uaaaaaacaa    540

acaaacgaac gaacagcaag ggagcugggu augacaacac auacuauaau ucuaguacuc    600

aggaugcuga aacaggagga uugccugacu gggagauaua aggagaaucu guugucaccc    660

ccaccccucc ccauaaaggc agaauaaaag aacguccuau aaacaaauaa acaaacaacc    720

caauaaaaca aaaccaagau cucuccaccu uuucuuugcu uuuucagacu uuguaauaag    780

gcccuuugga gugcaggaua uucggcagga caagcagaga gggagaccau caguucuuuc    840

uuugaucaag aagacuaugu uccuuagcaa acuggugugu auuaucucuu augcaaugag    900

ccuggaaaga gggcacagcc accgaggaug guacagcaug gauggauggu acgcuacaga    960

gacucgggag cccaacugug aguggcugac uggcauggua gguucaggga agaauuggcc   1020

ugugaagaaa auguucuuga aaagugaaca aggugcagga gguaggagug gguccugggc   1080

aaagcagggg gugcauccca gccucaggga auagcacagc agaggucugu ugaugcaugc   1140

gagugcauga ccugcuugcc aauagacgau caagaauggg caaagcauca ugggugauga   1200

gugggagagg ggaugagaca uuccuuucuc ccugcugaga cuuccauuga accgaugagu   1260

ucugaauaga agaugccccc ccaccccccc accaguguag aaucugaagg gaggcauaua   1320

uuacccuaua uuacucugug uuggcggcga gcuaucugac agccaaccuu cccauacauu   1380

ucauugggca uacacuaaug acaggaaguu ccuuuugcuu guaugcaaga gauggcucac   1440

acgauggaga auuuaaucuu gaagggcgaa uuccaccaca cuggacuagu ggauccgagc   1500

ucgguaccaa gcuu                                                     1514
```

<210> SEQ ID NO 13
<211> LENGTH: 1449
<212> TYPE: RNA
<213> ORGANISM: Artificial Sequence
<220> FEATURE:
<223> OTHER INFORMATION: cMYC full length(d) IRUP

<400> SEQUENCE: 13

```
ccauuuuuau guuauauguu uacaagcccc acaccaggcu gaaaaucugc agaauucgcc     60
```

-continued

```
cuuaauucca gcgagaggca gagggagcga gcgggcggcc ggcuagggug gaagagccgg    120
gcgagcagag cugcgcugcg ggcguccugg gaagggagau ccggagcgaa uagggggcuu    180
cgccucuggc ccagcccucc cgcuugaucc cccaggccag cgguccgcaa cccuugccgc    240
auccacgaaa cuuugcccau agcagcgggc gggcacuuug cacuggaacu uacaacaccc    300
gagcaaggac gcgacucucc cgacgcgggg aggcuauucu gcccauuugg ggacacuucc    360
ccgccgcugc caggacccgc uucucugaaa ggcucuccuu gcagcugcuu agacgcugga    420
uuuuuuucgg guaguggaaa accagcagcc ucccgcgaag ucucuuaaaa aacaaacaaa    480
cgaacgaaca gcaagggagc uggguaugac aacacauacu auaauucuag uacucaggau    540
gcugaaacag gaggauugcc ugacugggag auauaaggag aaucuguugu cacccccacc    600
ccucccccaua aaggcagaau aaaagaacgu ccuauaaaca aauaaacaaa caacccaaua    660
aaacaaaacc aagaucucuc caccuuuucu uugcuuuuuc agacuuugua auaaggcccu    720
uuggagugca ggauauucgg caggacaagc agagagggag accaucaguu cuuucuuuga    780
ucaagaagac uauguuccuu agcaaacugg uguguauuau cucuuaugca augagccugg    840
aaagagggca cagccaccga ggaugguaca gcauggaugg augguacgcu acagagacuc    900
gggagcccaa cugugagugg cugacuggca ugguagguuc agggaagaau uggccuguga    960
agaaaauguu cuugaaaagu gaacaaggug caggagguag gagugggucc ugggcaaagc   1020
agggggugca ucccagccuc agggaauagc acagcagagg ucuguugaug caugcgagug   1080
caugaccugc uugccaauag acgaucaaga augggcaaag caucaugggu gaugaguggg   1140
agaggggaug agacauuccu uucucccugc ugagacuucc auugaaccga ugaguucuga   1200
auagaagaug ccccccccacc cccccaccag uguagaaucu gaagggaggc auauauuacc   1260
cuauauuacu cuguguuggc ggcgagcuau cugacagcca accuucccau acauuucauu   1320
gggcauacac uaaugacagg aaguuccuuu ugcuuguaug caagagaugg cucacacgau   1380
ggagaauuua aucuugaagg gcgaauucca ccacacugga cuaguggauc cgagcucggu   1440
accaagcuu                                                            1449
```

<210> SEQ ID NO 14
<211> LENGTH: 1449
<212> TYPE: RNA
<213> ORGANISM: Artificial Sequence
<220> FEATURE:
<223> OTHER INFORMATION: cMYC full length(i) IRUP

<400> SEQUENCE: 14

```
ccauuuuuau guuauauguu uacaagcccc acaccaggcu gaaaaucugc agaauucgcc     60
cuuucgcggg aggcugcugg uuuuccacua cccgaaaaaa auccagcguc uaagcagcug    120
caaggagagc cuuucagaga agcggguccu ggcagcggcg gggaaguguc cccaaauggg    180
cagaauagcc uccccgcguc gggagagucg cguccuugcu cggguguugu aaguuccagu    240
gcaaagugcc cgcccgcugc uaugggcaaa guuucgugga ugcggcaagg guugcggacc    300
gcuggccugg gggaucaagc gggagggcug ggccagaggc gaagccccccu auucgcuccg   360
gaucucccuu cccaggacgc ccgcagcgca gcucugcucg cccggcucuu ccacccuagc    420
cggccgcccg cucgcucccu cugccucucg cuggaauuag ucucuuaaaa aacaaacaaa    480
cgaacgaaca gcaagggagc uggguaugac aacacauacu auaauucuag uacucaggau    540
gcugaaacag gaggauugcc ugacugggag auauaaggag aaucuguugu cacccccacc    600
```

-continued

```
ccucccccaua aaggcagaau aaaagaacgu ccuauaaaca aauaaacaaa caacccaaua    660

aaacaaaacc aagaucucuc caccuuuucu uugcuuuuuc agacuuugua auaaggcccu    720

uuggagugca ggauauucgg caggacaagc agagagggag accaucaguu cuuucuuuga    780

ucaagaagac uauguuccuu agcaaacugg uguguauuau cucuuaugca augagccugg    840

aaagagggca cagccaccga ggaugguaca gcauggaugg augguacgcu acagagacuc    900

gggagcccaa cugugagugg cugacuggca ugguagguuc agggaagaau uggccuguga    960

agaaaauguu cuugaaaagu gaacaaggug caggagguag gagugggucc ugggcaaagc   1020

agggggugca ucccagccuc agggaauagc acagcagagg ucuguugaug caugcgagug   1080

caugaccugc uugccaauag acgaucaaga augggcaaag caucaugggu gaugaguggg   1140

agaggggaug agacauuccu uucucccugc ugagacuucc auugaaccga ugaguucuga   1200

auagaagaug cccccccacc cccccaccag uguagaaucu gaagggaggc auauauuacc   1260

cuauauuacu cuguguuggc ggcgagcuau cugacagcca accuucccau acauuucauu   1320

gggcauacac uaaugacagg aaguuccuuu ugcuuguaug caagagaugg cucacacgau   1380

ggagaauuua aucuugaagg gcgaauucca ccacacugga cuaguggauc cgagcucggu   1440

accaagcuu                                                           1449
```

<210> SEQ ID NO 15
<211> LENGTH: 1102
<212> TYPE: RNA
<213> ORGANISM: Artificial Sequence
<220> FEATURE:
<223> OTHER INFORMATION: cMYC short variant(d) IRUP

<400> SEQUENCE: 15

```
ccauuuuuau guuauauguu uacaagcccc acaccaggcu gaaaaucugc agaauucgcc     60

cuugggcacu uugcacugga acuuacaaca cccgagcaag gacgcgacuc uagucucuua    120

aaaaacaaac aaacgaacga acagcaaggg agcuggguau gacaacacau acuauaauuc    180

uaguacucag gaugcugaaa caggaggauu gccugacugg gagauauaag gagaaucugu    240

ugucaccccc accccucccc auaaaggcag aauaaaagaa cguccuauaa acaaauaaac    300

aaacaaccca auaaaacaaa accaagaucu cuccaccuuu ucuuugcuuu uucagacuuu    360

guaauaaggc ccuuuggagu gcaggauauu cggcaggaca agcagagagg gagaccauca    420

guucuuucuu ugaucaagaa gacuauguuc cuuagcaaac ugguguguau uaucucuuau    480

gcaaugagcc uggaaagagg gcacagccac cgaggauggu acagcaugga uggaugguac    540

gcuacagaga cucgggagcc caacugugag uggcugacug gcaugguagg uucagggaag    600

aauuggccug ugaagaaaau guucuugaaa agugaacaag gugcaggagg uaggaguggg    660

uccugggcaa agcagggggu gcaucccagc cucagggaau agcacagcag aggucuguug    720

augcaugcga gugcaugacc ugcuugccaa uagacgauca agaaugggca aagcaucaug    780

ggugaugagu gggagagggg augagacauu ccuuucuccc ugcugagacu uccauugaac    840

cgaugaguuc ugaauagaag augccccccc acccccccac caguguagaa ucugaaggga    900

ggcauauauu acccuauauu acucuguguu ggcggcgagc uaucugacag ccaaccuucc    960

cauacauuuc auugggcaua cacuaaugac aggaaguucc uuuugcuugu augcaagaga   1020

uggcucacac gauggagaau uuaaucuuga agggcgaauu ccaccacacu ggacuagugg   1080

auccgagcuc gguaccaagc uu                                            1102
```

-continued

<210> SEQ ID NO 16
<211> LENGTH: 1102
<212> TYPE: RNA
<213> ORGANISM: Artificial Sequence
<220> FEATURE:
<223> OTHER INFORMATION: cMYC short variant(i) IRUP

<400> SEQUENCE: 16
ccauuuuuau guuauauguu uacaagcccc acaccaggcu gaaaaucugc agaauucgcc 60
cuuagagucg cguccuugcu cggguguugu aaguuccagu gcaaagugcc cagucucuua 120
aaaaacaaac aaacgaacga acagcaaggg agcuggguau gacaacacau acuauaauuc 180
uaguacucag gaugcugaaa caggaggauu gccugacugg gagauauaag gagaaucugu 240
ugucaccccc accccucccc auaaaggcag aauaaaagaa cguccuauaa acaaauaaac 300
aaacaaccca auaaaacaaa accaagaucu cuccaccuuu ucuuugcuuu uucagacuuu 360
guaauaaggc ccuuuggagu gcaggauauu cggcaggaca agcagagagg gagaccauca 420
guucuuucuu ugaucaagaa gacuauguuc cuuagcaaac uggugugauu uaucucuuau 480
gcaaugagcc uggaaagagg gcacagccac cgaggauggu acagcaugga uggaugguac 540
gcuacagaga cucgggagcc caacugugag uggcugacug gcaugguagg uucagggaag 600
aauuggccug ugaagaaaau guucuugaaa agugaacaag gugcaggagg uaggaguggg 660
uccugggcaa agcagggggu gcaucccagc cucagggaau agcacagcag aggucuguug 720
augcaugcga gugcaugacc ugcuugccaa uagacgauca agaaugggca aagcaucaug 780
ggugaugagu gggagagggg augagacauu ccuuucuccc ugcugagacu uccauugaac 840
cgaugaguuc ugaauagaag augccccccc acccccccac caguguagaa ucugaaggga 900
ggcauauauu acccuauauu acucuguguu ggcggcgagc uaucugacag ccaaccuucc 960
cauacauuuc auugggcaua cacuaaugac aggaaguucc uuuugcuugu augcaagaga 1020
uggcucacac gauggagaau uuaaucuuga agggcgaauu ccaccacacu ggacuagugg 1080
auccgagcuc gguaccaagc uu 1102

<210> SEQ ID NO 17
<211> LENGTH: 1125
<212> TYPE: RNA
<213> ORGANISM: Artificial Sequence
<220> FEATURE:
<223> OTHER INFORMATION: DMD(d) IRUP

<400> SEQUENCE: 17
ccauuuuuau guuauauguu uacaagcccc acaccaggcu gaaaaucugc agaauucgcc 60
cuuguacuga caucguagau ggaaaucaua aacugacucu ugguuugauu uggaauauaa 120
uccuccacug gcagagucuc uuaaaaaaca aacaaacgaa cgaacagcaa gggagcuggg 180
uaugacaaca cauacuauaa uucuaguacu caggaugcug aaacaggagg auugccugac 240
ugggagauau aaggagaauc uguugucacc cccaccccuc cccauaaagg cagaauaaaa 300
gaacguccua uaaacaaaua aacaaacaac ccaauaaaac aaaaccaaga ucucuccacc 360
uuuucuuugc uuuuucagac uuuguaauaa ggcccuuugg agugcaggau auucggcagg 420
acaagcagag agggagacca ucaguucuuu cuuugaucaa gaagacuaug uuccuuagca 480
aacuggugug uauuaucucu uaugcaauga gccuggaaag agggcacagc caccgaggau 540
gguacagcau ggauggaugg uacgcuacag agacucggga gcccaacugu gaguggcuga 600
cuggcauggu agguucaggg aagaauuggc cugugaagaa aauguucuug aaaagugaac 660

-continued

```
aaggugcagg agguaggagu ggguccuggg caaagcaggg ggugcauccc agccucaggg    720

aauagcacag cagaggucug uugaugcaug cgagugcaug accugcuugc caauagacga    780

ucaagaaugg gcaaagcauc augggugaug agugggagag gggaugagac auuccuuucu    840

cccugcugag acuuccauug aaccgaugag uucugaauag aagaugcccc cccacccccc    900

caccagugua gaaucugaag ggaggcauau auuacccuau auuacucugu guuggcggcg    960

agcuaucuga cagccaaccu ucccauacau uucauugggc auacacuaau gacaggaagu   1020

uccuuuugcu uguaugcaag agauggcuca cacgauggag aauuuaaucu ugaagggcga   1080

auuccaccac acuggacuag uggauccgag cucgguacca agcuu                   1125
```

<210> SEQ ID NO 18
<211> LENGTH: 1125
<212> TYPE: RNA
<213> ORGANISM: Artificial Sequence
<220> FEATURE:
<223> OTHER INFORMATION: DMD(i) IRUP

<400> SEQUENCE: 18

```
ccauuuuuau guuauauguu uacaagcccc acaccaggcu gaaaaucugc agaauucgcc     60

cuucugccag uggaggauua uauuccaaau caaaccaaga gucaguuuau gauuuccauc    120

uacgauguca guacagucuc uuaaaaaaca aacaaacgaa cgaacagcaa gggagcuggg    180

uaugacaaca cauacuauaa uucuaguacu caggaugcug aaacaggagg auugccugac    240

ugggagauau aaggagaauc uguugucacc cccaccccuc cccauaaagg cagaauaaaa    300

gaacguccua uaaacaaaua aacaaacaac ccaauaaaac aaaaccaaga ucucuccacc    360

uuuucuuugc uuuuucagac uuuguaauaa ggcccuuugg agugcaggau auucggcagg    420

acaagcagag agggagacca ucaguucuuu cuuugaucaa gaagacuaug uuccuuagca    480

aacuggugug uauuaucucu uaugcaauga gccuggaaag agggcacagc caccgaggau    540

gguacagcau ggauggaugg uacgcuacag agacucggga gcccaacugu gaguggcuga    600

cuggcauggu agguucaggg aagaauuggc cugugaagaa aauguucuug aaaagugaac    660

aaggugcagg agguaggagu ggguccuggg caaagcaggg ggugcauccc agccucaggg    720

aauagcacag cagaggucug uugaugcaug cgagugcaug accugcuugc caauagacga    780

ucaagaaugg gcaaagcauc augggugaug agugggagag gggaugagac auuccuuucu    840

cccugcugag acuuccauug aaccgaugag uucugaauag aagaugcccc cccacccccc    900

caccagugua gaaucugaag ggaggcauau auuacccuau auuacucugu guuggcggcg    960

agcuaucuga cagccaaccu ucccauacau uucauugggc auacacuaau gacaggaagu   1020

uccuuuugcu uguaugcaag agauggcuca cacgauggag aauuuaaucu ugaagggcga   1080

auuccaccac acuggacuag uggauccgag cucgguacca agcuu                   1125
```

<210> SEQ ID NO 19
<211> LENGTH: 1357
<212> TYPE: RNA
<213> ORGANISM: Artificial Sequence
<220> FEATURE:
<223> OTHER INFORMATION: HCV delta II(d) IRUP

<400> SEQUENCE: 19

```
ccauuuuuau guuauauguu uacaagcccc acaccaggcu gaaaaucugc agaauucgcc     60

cuugccagcc cccugauggg ggcgacacuc caccaugaau cacccccccu cccgggagag    120

ccauaguggu cugcggaacc ggugaguaca ccggaauugc caggacgacc ggguccuuuc    180
```

uuggauaaac ccgcucaaug ccuggagauu ugggcgugcc cccgcaagac ugcuagccga 240
guaguguugg gucgcgaaag gccuuguggu acugccugau agggugcuug cgagugcccc 300
gggaggucuc guagaccgug caccaugagc acgaauccua aaccucaaag aaaaaccaaa 360
cguaacaguc ucuuaaaaaa caaacaaacg aacgaacagc aagggagcug gguaugacaa 420
cacauacuau aauucuagua cucaggaugc ugaaacagga ggauugccug acugggagau 480
auaaggagaa ucuguuguca cccccacccc uccccauaaa ggcagaauaa aagaacgucc 540
uauaaacaaa uaaacaaaca acccaauaaa acaaaaccaa gaucucucca ccuuuucuuu 600
gcuuuuucag acuuuguaau aaggcccuuu ggagugcagg auauucggca ggacaagcag 660
agagggagac caucaguucu uucuuugauc aagaagacua uguuccuuag caaacuggug 720
uguauuaucu cuuaugcaau gagccuggaa agagggcaca gccaccgagg augguacagc 780
auggauggau gguacgcuac agagacucgg gagcccaacu gugaguggcu gacuggcaug 840
guagguucag ggaagaauug gccugugaag aaaauguucu ugaaaaguga acaaggugca 900
ggagguagga gugggguccug ggcaaagcag ggggugcauc ccagccucag ggaauagcac 960
agcagagguc uguugaugca ugcgagugca ugaccugcuu gccaauagac gaucaagaau 1020
gggcaaagca ucaugggguga ugagugggag aggggaugag acauuccuuu cucccugcug 1080
agacuuccau ugaaccgaug aguucugaau agaagaugcc cccccacccc cccaccagug 1140
uagaaucuga agggaggcau auauuacccu auauuacucu guguuggcgg cgagcuaucu 1200
gacagccaac cuucccauac auuucauugg gcauacacua augacaggaa guuccuuuug 1260
cuuguaugca agagauggcu cacacgaugg agaauuuaau cuugaagggc gaauuccacc 1320
acacuggacu aguggauccg agcucgguac caagcuu 1357

<210> SEQ ID NO 20
<211> LENGTH: 1421
<212> TYPE: RNA
<213> ORGANISM: Artificial Sequence
<220> FEATURE:
<223> OTHER INFORMATION: HCV delta IIIa(d) IRUP

<400> SEQUENCE: 20
ccauuuuuau guuauauguu uacaagcccc acaccaggcu gaaaaucugc agaauucgcc 60
cuugccagcc cccugauggg ggcgacacuc caccaugaau cacuccccug ugaggaacua 120
cugucuucac gcagaaagcg ucuagccaug gcguuaguau gagugucgug cagccuccag 180
gacccccccu cccgggagag ccauaguggu cugcggaaaa uugccaggac gaccgggucc 240
uuucuuggau aaacccgcuc aaugccugga gauuugggcg ugcccccgca agacugcuag 300
ccgaguagug uugggucgcg aaaggccuug ugguacugcc ugauagggug cuugcgagug 360
ccccgggagg ucucguagac cgugcaccau gagcacgaau ccuaaaccuc aaagaaaaac 420
caaacguaac agucucuuaa aaaacaaaca aacgaacgaa cagcaaggga gcuggguaug 480
acaacacaua cuauaauucu aguacucagg augcugaaac aggaggauug ccugacuggg 540
agauauaagg agaaucuguu gucacccccca ccccuccccca uaaaggcaga auaaaagaac 600
guccuauaaa caaauaaaca aacaacccaa uaaaacaaaa ccaagaucuc uccaccuuuu 660
cuuugcuuuu ucagacuuug uaauaaggcc cuuuggagug caggauauuc ggcaggacaa 720
gcagagaggg agaccaucag uucuuucuuu gaucaagaag acuauguucc uuagcaaacu 780
gguguguauu aucucuuaug caaugagccu ggaaagaggg cacagccacc gaggauggua 840

-continued

```
cagcauggau ggaugguacg cuacagagac ucgggagccc aacugugagu ggcugacugg    900

caugguaggu ucagggaaga auuggccugu gaagaaaaug uucuugaaaa gugaacaagg    960

ugcaggaggu aggagugggu ccugggcaaa gcagggggug caucccagcc ucagggaaua   1020

gcacagcaga ggucuguuga ugcaugcgag ugcaugaccu gcuugccaau agacgaucaa   1080

gaaugggcaa agcaucaugg gugaugagug ggagagggga ugagacauuc cuuucucccu   1140

gcugagacuu ccauugaacc gaugaguucu gaauagaaga ugccccccca cccccccacc   1200

aguguagaau cugaagggag gcauauauua cccuauauua cucuguguug gcggcgagcu   1260

aucugacagc caaccuuccc auacauuuca uugggcauac acuaaugaca ggaaguuccu   1320

uuugcuugua ugcaagagau ggcucacacg auggagaauu uaaucuugaa gggcgaauuc   1380

caccacacug gacuagugga uccgagcucg guaccaagcu u                       1421


<210> SEQ ID NO 21
<211> LENGTH: 1410
<212> TYPE: RNA
<213> ORGANISM: Artificial Sequence
<220> FEATURE:
<223> OTHER INFORMATION: HCV delta IIId(d) IRUP

<400> SEQUENCE: 21

ccauuuuuau guuauauguu uacaagcccc acaccaggcu gaaaaucugc agaauucgcc     60

cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu ugggcgugcc    300

cccgcaagac ugcuacuugu gguacugccu gauagggugc uugcgagugc cccgggaggu    360

cucguagacc gugcaccaug agcacgaauc cuaaaccuca aagaaaaacc aaacguaaca    420

gucucuuaaa aaacaaacaa acgaacgaac agcaagggag cuggguauga caacacauac    480

uauaauucua guacucagga ugcugaaaca ggaggauugc cugacuggga gauauaagga    540

gaaucuguug ucacccccac cccuccccau aaaggcagaa uaaaagaacg uccuauaaac    600

aaauaaacaa acaacccaau aaaacaaaac caagaucucu ccaccuuuuc uuugcuuuuu    660

cagacuuugu aauaaggccc uuuggagugc aggauauucg gcaggacaag cagagaggga    720

gaccaucagu ucuuucuuug aucaagaaga cuauguuccu uagcaaacug guguguauua    780

ucucuuaugc aaugagccug gaaagagggc acagccaccg aggaugguac agcauggaug    840

gaugguacgc uacagagacu cgggagccca acugugagug gcugacuggc augguagguu    900

cagggaagaa uuggccugug aagaaaaugu ucuugaaaag ugaacaaggu gcaggaggua    960

ggagugggucc ugggcaaag caggggggugc aucccagccu cagggaauag cacagcagag   1020

gucuguugau gcaugcgagu gcaugaccug cuugccaaua gacgaucaag aaugggcaaa   1080

gcaucauggg ugaugagugg gagaggggau gagacauucc uuucucccug cugagacuuc   1140

cauugaaccg augaguucug aauagaagau gccccccccac cccccccacca guguagaauc   1200

ugaagggagg cauauauuac ccuauauuac ucuguguugg cggcgagcua ucugacagcc   1260

aaccuuccca uacauuucau ugggcauaca cuaaugacag gaaguuccuu uugcuuguau   1320

gcaagagaug gcucacacga uggagaauuu aaucuugaag ggcgaauucc accacacugg   1380

acuaguggau ccgagcucgg uaccaagcuu                                    1410
```

-continued

<210> SEQ ID NO 22
<211> LENGTH: 1384
<212> TYPE: RNA
<213> ORGANISM: Artificial Sequence
<220> FEATURE:
<223> OTHER INFORMATION: HCV delta IV(d) IRUP

<400> SEQUENCE: 22

```
ccauuuuuau guuauauguu uacaagcccc acaccaggcu gaaaaucugc agaauucgcc     60

cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu ugggcgugcc    300

cccgcaagac ugcuagccga guaguguugg gucgcgaaag gccuuguggu acugccugau    360

agggugcuug cgagugcccc gggaggucuc guaagucucu uaaaaaacaa acaaacgaac    420

gaacagcaag ggagcugggu augacaacac auacuauaau ucuaguacuc aggaugcuga    480

aacaggagga uugccugacu gggagauaua aggagaaucu guugucaccc ccaccccucc    540

ccauaaaggc agaauaaaag aacguccuau aaacaaauaa acaaacaacc caauaaaaca    600

aaaccaagau cucuccaccu uuucuuugcu uuuucagacu uuguaauaag gcccuuugga    660

gugcaggaua uucggcagga caagcagaga gggagaccau caguucuuuc uuugaucaag    720

aagacuaugu uccuuagcaa acuggugugu auuaucucuu augcaaugag ccuggaaaga    780

gggcacagcc accgaggaug guacagcaug gauggauggu acgcuacaga gacucgggag    840

cccaacugug aguggcugac uggcauggua gguucaggga agaauuggcc ugugaagaaa    900

auguucuuga aaagugaaca aggugcagga gguaggagug gguccugggc aaagcagggg    960

gugcauccca gccucaggga auagcacagc agaggucugu ugaugcaugc gagugcauga   1020

ccugcuugcc aauagacgau caagaauggg caaagcauca ugggugauga gugggagagg   1080

ggaugagaca uuccuuucuc ccugcugaga cuuccauuga accgaugagu ucugaauaga   1140

agaugccccc ccaccccccc accaguguag aaucugaagg gaggcauaua uuacccuaua   1200

uuacucugug uuggcggcga gcuaucugac agccaaccuu cccauacauu ucauugggca   1260

uacacuaaug acaggaaguu ccuuuugcuu guaugcaaga gauggcucac acgauggaga   1320

auuuaaucuu gaagggcgaa uuccaccaca cuggacuagu ggauccgagc ucgguaccaa   1380

gcuu                                                                1384
```

<210> SEQ ID NO 23
<211> LENGTH: 1437
<212> TYPE: RNA
<213> ORGANISM: Artificial Sequence
<220> FEATURE:
<223> OTHER INFORMATION: HCV G266->C(d) IRUP

<400> SEQUENCE: 23

```
ccauuuuuau guuauauguu uacaagcccc acaccaggcu gaaaaucugc agaauucgcc     60

cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu ugggcgugcc    300

cccgcaagac ugcuagccga guaguguucg gucgcgaaag gccuuguggu acugccugau    360
```

-continued

```
agggugcuug cgagugcccc gggaggucuc guagaccgug caccaugagc acgaauccua    420

aaccucaaag aaaaaccaaa cguaacaguc ucuuaaaaaa caaacaaacg aacgaacagc    480

aagggagcug gguaugacaa cacauacuau aauucuagua cucaggaugc ugaaacagga    540

ggauugccug acugggagau auaaggagaa ucuguuguca cccccacccc uccccauaaa    600

ggcagaauaa aagaacgucc uauaaacaaa uaaacaaaca acccaauaaa acaaaaccaa    660

gaucucucca ccuuuucuuu gcuuuuucag acuuuguaau aaggcccuuu ggagugcagg    720

auauucggca ggacaagcag agagggagac caucaguucu uucuuugauc aagaagacua    780

uguuccuuag caaacuggug uguauuaucu cuuaugcaau gagccuggaa agagggcaca    840

gccaccgagg augguacagc auggauggau gguacgcuac agagacucgg gagcccaacu    900

gugaguggcu gacuggcaug guagguucag ggaagaauug gccugugaag aaaauguucu    960

ugaaaaguga acaaggugca ggagguagga gugggguccug ggcaaagcag ggggugcauc   1020

ccagccucag ggaauagcac agcagagguc uguugaugca ugcgagugca ugaccugcuu   1080

gccaauagac gaucaagaau gggcaaagca ucauggguga ugagugggag aggggaugag   1140

acauuccuuu cucccugcug agacuuccau ugaaccgaug aguucugaau agaagaugcc   1200

cccccacccc cccaccagug uagaaucuga agggaggcau auauuacccu auauuacucu   1260

guguuggcgg cgagcuaucu gacagccaac cuucccauac auuucauugg gcauacacua   1320

augacaggaa guuccuuuug cuuguaugca agagauggcu cacacgaugg agaauuuaau   1380

cuugaagggc gaauuccacc acacuggacu aguggauccg agcucgguac caagcuu      1437
```

<210> SEQ ID NO 24
<211> LENGTH: 1437
<212> TYPE: RNA
<213> ORGANISM: Artificial Sequence
<220> FEATURE:
<223> OTHER INFORMATION: HCV U228->C(d) IRUP

<400> SEQUENCE: 24

```
ccauuuuuau guuauauguu uacaagcccc acaccaggcu gaaaaucugc agaauucgcc     60

cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu cgggcgugcc    300

cccgcaagac ugcuagccga guaguguugg gucgcgaaag gccuugugguu acugccugau    360

agggugcuug cgagugcccc gggaggucuc guagaccgug caccaugagc acgaauccua    420

aaccucaaag aaaaaccaaa cguaacaguc ucuuaaaaaa caaacaaacg aacgaacagc    480

aagggagcug gguaugacaa cacauacuau aauucuagua cucaggaugc ugaaacagga    540

ggauugccug acugggagau auaaggagaa ucuguuguca cccccacccc uccccauaaa    600

ggcagaauaa aagaacgucc uauaaacaaa uaaacaaaca acccaauaaa acaaaaccaa    660

gaucucucca ccuuuucuuu gcuuuuucag acuuuguaau aaggcccuuu ggagugcagg    720

auauucggca ggacaagcag agagggagac caucaguucu uucuuugauc aagaagacua    780

uguuccuuag caaacuggug uguauuaucu cuuaugcaau gagccuggaa agagggcaca    840

gccaccgagg augguacagc auggauggau gguacgcuac agagacucgg gagcccaacu    900

gugaguggcu gacuggcaug guagguucag ggaagaauug gccugugaag aaaauguucu    960

ugaaaaguga acaaggugca ggagguagga gugggguccug ggcaaagcag ggggugcauc   1020
```

-continued ccagccucag ggaauagcac agcagagguc uguugaugca ugcgagugca ugaccugcuu 1080
gccaauagac gaucaagaau gggcaaagca ucauggguga ugagugggag aggggaugag 1140
acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 25
<211> LENGTH: 1437
<212> TYPE: RNA
<213> ORGANISM: Artificial Sequence
<220> FEATURE:
<223> OTHER INFORMATION: HCV G267->C(d) IRUP

<400> SEQUENCE: 25
ccauuuuuau guuauauguu uacaagcccc acaccaggcu gaaaaucugc agaauucgcc 60
cuugccagcc cccugauggg ggcgacacuc caccaugaau cacuccccug ugaggaacua 120
cugucuucac gcagaaagcg ucuagccaug gcguuaguau gagugucgug cagccuccag 180
gacccccccu cccgggagag ccauaguggu cugcggaacc ggugaguaca ccggaauugc 240
caggacgacc ggguccuuuc uuggauaaac ccgcucaaug ccuggagauu ugggcgugcc 300
cccgcaagac ugcuagccga guaguguugc gucgcgaaag gccuuguggu acugccugau 360
agggugcuug cgagugcccc gggaggucuc guagaccgug caccaugagc acgaauccua 420
aaccucaaag aaaaaccaaa cguaacaguc ucuuaaaaaa caaacaaacg aacgaacagc 480
aagggagcug gguaugacaa cacauacuau aauucuagua cucaggaugc ugaaacagga 540
ggauugccug acugggagau auaaggagaa ucuguuguca cccccacccc uccccauaaa 600
ggcagaauaa aagaacgucc uauaaacaaa uaaacaaaca acccaauaaa acaaaaccaa 660
gaucucucca ccuuuucuuu gcuuuuucag acuuuguaau aaggcccuuu ggagugcagg 720
auauucggca ggacaagcag agagggagac caucaguucu uucuuugauc aagaagacua 780
uguuccuuag caaacuggug uguauuaucu cuuaugcaau gagccuggaa agagggcaca 840
gccaccgagg augguacagc auggauggau gguacgcuac agagacucgg gagcccaacu 900
gugaguggcu gacuggcaug guagguucag ggaagaauug gccugugaag aaaauguucu 960
ugaaaaguga acaaggugca ggagguagga gugggguccug ggcaaagcag ggggugcauc 1020
ccagccucag ggaauagcac agcagagguc uguugaugca ugcgagugca ugaccugcuu 1080
gccaauagac gaucaagaau gggcaaagca ucauggguga ugagugggag aggggaugag 1140
acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 26
<211> LENGTH: 1437
<212> TYPE: RNA
<213> ORGANISM: Artificial Sequence
<220> FEATURE:

-continued

<223> OTHER INFORMATION: HCV G268->C(d) IRUP

<400> SEQUENCE: 26
ccauuuuuau guuauauguu uacaagcccc acaccaggcu gaaaaucugc agaauucgcc 60
cuugccagcc cccugauggg ggcgacacuc caccaugaau cacuccccug ugaggaacua 120
cugucuucac gcagaaagcg ucuagccaug gcguuaguau gagugucgug cagccuccag 180
gacccccccu cccgggagag ccauaguggu cugcggaacc ggugaguaca ccggaauugc 240
caggacgacc ggguccuuuc uuggauaaac ccgcucaaug ccuggagauu ugggcgugcc 300
cccgcaagac ugcuagccga guaguguugg cucgcgaaag gccuuguggu acugccugau 360
agggugcuug cgagugcccc gggaggucuc guagaccgug caccaugagc acgaauccua 420
aaccucaaag aaaaaccaaa cguaacaguc ucuuaaaaaa caaacaaacg aacgaacagc 480
aagggagcug gguaugacaa cacauacuau aauucuagua cucaggaugc ugaaacagga 540
ggauugccug acugggagau auaaggagaa ucuguuguca cccccacccc uccccauaaa 600
ggcagaauaa aagaacgucc uauaaacaaa uaaacaaaca acccaauaaa acaaaaccaa 660
gaucucucca ccuuuucuuu gcuuuuucag acuuuguaau aaggcccuuu ggagugcagg 720
auauucggca ggacaagcag agagggagac caucaguucu uucuuugauc aagaagacua 780
uguuccuuag caaacuggug uguauuaucu cuuaugcaau gagccuggaa agagggcaca 840
gccaccgagg augguacagc auggauggau gguacgcuac agagacucgg gagcccaacu 900
gugaguggcu gacuggcaug guagguucag ggaagaauug gccugugaag aaaauguucu 960
ugaaaaguga acaaggugca ggagguagga gugggguccug ggcaaagcag ggggugcauc 1020
ccagccucag ggaauagcac agcagagguc uguugaugca ugcgagugca ugaccugcuu 1080
gccaauagac gaucaagaau gggcaaagca ucaugggu ga ugagugggag aggggaugag 1140
acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 27
<211> LENGTH: 1437
<212> TYPE: RNA
<213> ORGANISM: Artificial Sequence
<220> FEATURE:
<223> OTHER INFORMATION: HCV G266G267G268-> C266C267C268(d) IRUP

<400> SEQUENCE: 27
ccauuuuuau guuauauguu uacaagcccc acaccaggcu gaaaaucugc agaauucgcc 60
cuugccagcc cccugauggg ggcgacacuc caccaugaau cacuccccug ugaggaacua 120
cugucuucac gcagaaagcg ucuagccaug gcguuaguau gagugucgug cagccuccag 180
gacccccccu cccgggagag ccauaguggu cugcggaacc ggugaguaca ccggaauugc 240
caggacgacc ggguccuuuc uuggauaaac ccgcucaaug ccuggagauu ugggcgugcc 300
cccgcaagac ugcuagccga guaguguucc cucgcgaaag gccuuguggu acugccugau 360
agggugcuug cgagugcccc gggaggucuc guagaccgug caccaugagc acgaauccua 420
aaccucaaag aaaaaccaaa cguaacaguc ucuuaaaaaa caaacaaacg aacgaacagc 480
aagggagcug gguaugacaa cacauacuau aauucuagua cucaggaugc ugaaacagga 540

```
ggauugccug acugggagau auaaggagaa ucuguuguca cccccacccc uccccauaaa    600
ggcagaauaa aagaacgucc uauaaacaaa uaaacaaaca acccaauaaa acaaaaccaa    660
gaucucucca ccuuuucuuu gcuuuuucag acuuuguaau aaggcccuuu ggagugcagg    720
auauucggca ggacaagcag agagggagac caucaguucu uucuuugauc aagaagacua    780
uguuccuuag caaacuggug uguauuaucu cuuaugcaau gagccuggaa agagggcaca    840
gccaccgagg augguacagc auggauggau gguacgcuac agagacucgg gagcccaacu    900
gugaguggcu gacuggcaug guagguucag ggaagaauug gccugugaag aaaauguucu    960
ugaaaaguga acaaggugca ggagguagga gugggguccug ggcaaagcag ggggugcauc   1020
ccagccucag ggaauagcac agcagagguc uguugaugca ugcgagugca ugaccugcuu   1080
gccaauagac gaucaagaau gggcaaagca ucauggguga ugagugggag aggggaugag   1140
acauuccuuu cucccugcug agacuuccau ugaaccgaug aguucugaau agaagaugcc   1200
cccccacccc cccaccagug uagaaucuga agggaggcau auauuacccu auauuacucu   1260
guguuggcgg cgagcuaucu gacagccaac cuucccauac auuucauugg gcauacacua   1320
augacaggaa guuccuuuug cuuguaugca agagauggcu cacacgaugg agaauuuaau   1380
cuugaagggc gaauuccacc acacuggacu aguggauccg agcucgguac caagcuu       1437
```

<210> SEQ ID NO 28
<211> LENGTH: 1437
<212> TYPE: RNA
<213> ORGANISM: Artificial Sequence
<220> FEATURE:
<223> OTHER INFORMATION: HCV G266->A/G268->T(d) IRUP

<400> SEQUENCE: 28

```
ccauuuuuau guuauauguu uacaagcccc acaccaggcu gaaaaucugc agaauucgcc     60
cuugccagcc cccugauggg ggcgacacuc caccaugaau cacuccccug ugaggaacua    120
cugucuucac gcagaaagcg ucuagccaug gcguuaguau gagugucgug cagccuccag    180
gacccccccu cccgggagag ccauaguggu cugcggaacc ggugaguaca ccggaauugc    240
caggacgacc ggguccuuuc uuggauaaac ccgcucaaug ccuggagauu ugggcgugcc    300
cccgcaagac ugcuagccga guaguguuag uucgcgaaag gccuuguggu acugccugau    360
agggugcuug cgagugcccc gggaggucuc guagaccgug caccaugagc acgaauccua    420
aaccucaaag aaaaaccaaa cguaacaguc ucuuaaaaaa caaacaaacg aacgaacagc    480
aagggagcug gguaugacaa cacauacuau aauucuagua cucaggaugc ugaaacagga    540
ggauugccug acugggagau auaaggagaa ucuguuguca cccccacccc uccccauaaa    600
ggcagaauaa aagaacgucc uauaaacaaa uaaacaaaca acccaauaaa acaaaaccaa    660
gaucucucca ccuuuucuuu gcuuuuucag acuuuguaau aaggcccuuu ggagugcagg    720
auauucggca ggacaagcag agagggagac caucaguucu uucuuugauc aagaagacua    780
uguuccuuag caaacuggug uguauuaucu cuuaugcaau gagccuggaa agagggcaca    840
gccaccgagg augguacagc auggauggau gguacgcuac agagacucgg gagcccaacu    900
gugaguggcu gacuggcaug guagguucag ggaagaauug gccugugaag aaaauguucu    960
ugaaaaguga acaaggugca ggagguagga gugggguccug ggcaaagcag ggggugcauc   1020
ccagccucag ggaauagcac agcagagguc uguugaugca ugcgagugca ugaccugcuu   1080
gccaauagac gaucaagaau gggcaaagca ucauggguga ugagugggag aggggaugag   1140
```

acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 29
<211> LENGTH: 1437
<212> TYPE: RNA
<213> ORGANISM: Artificial Sequence
<220> FEATURE:
<223> OTHER INFORMATION: HCV IIIa->IIIa-comp; AGTA->TCAT(d) IRUP

<400> SEQUENCE: 29
ccauuuuuau guuauauguu uacaagcccc acaccaggcu gaaaaucugc agaauucgcc 60
cuugccagcc cccugauggg ggcgacacuc caccaugaau cacuccccug ugaggaacua 120
cugucuucac gcagaaagcg ucuagccaug gcguuaguau gagugucgug cagccuccag 180
gacccccccu cccgggagag ccauaguggu cugcggaacc ggugucauca ccggaauugc 240
caggacgacc ggguccuuuc uuggauaaac ccgcucaaug ccuggagauu ugggcgugcc 300
cccgcaagac ugcuagccga guaguguugg gucgcgaaag gccuuguggu acugccugau 360
agggugcuug cgagugcccc gggaggucuc guagaccgug caccaugagc acgaauccua 420
aaccucaaag aaaaaccaaa cguaacaguc ucuuaaaaaa caaacaaacg aacgaacagc 480
aagggagcug gguaugacaa cacauacuau aauucuagua cucaggaugc ugaaacagga 540
ggauugccug acugggagau auaaggagaa ucuguuguca cccccacccc uccccauaaa 600
ggcagaauaa aagaacgucc uauaaacaaa uaaacaaaca acccaauaaa acaaaaccaa 660
gaucucucca ccuuuucuuu gcuuuuucag acuuuguaau aaggcccuuu ggagugcagg 720
auauucggca ggacaagcag agagggagac caucaguucu uucuuugauc aagaagacua 780
uguuccuuag caaacuggug uguauuaucu cuuaugcaau gagccuggaa agagggcaca 840
gccaccgagg augguacagc auggauggau gguacgcuac agagacucgg gagcccaacu 900
gugaguggcu gacuggcaug guagguucag ggaagaauug gccugugaag aaaauguucu 960
ugaaaaguga acaaggugca ggagguagga gugggguccug ggcaaagcag ggggugcauc 1020
ccagccucag ggaauagcac agcagagguc uguugaugca ugcgagugca ugaccugcuu 1080
gccaauagac gaucaagaau gggcaaagca ucaugggugu ugagugggag aggggaugag 1140
acauuccuuu cucccugcug agacuuccau ugaaccgaug aguucugaau agaagaugcc 1200
cccccacccc cccaccagug uagaaucuga agggaggcau auauuacccu auauuacucu 1260
guguuggcgg cgagcuaucu gacagccaac cuucccauac auuucauugg gcauacacua 1320
augacaggaa guuccuuuug cuuguaugca agagauggcu cacacgaugg agaauuuaau 1380
cuugaagggc gaauuccacc acacuggacu aguggauccg agcucgguac caagcuu 1437

<210> SEQ ID NO 30
<211> LENGTH: 1437
<212> TYPE: RNA
<213> ORGANISM: Artificial Sequence
<220> FEATURE:
<223> OTHER INFORMATION: HCV IIIe->IIIe-comp; TGATAG->ACTATC(d) IRUP

<400> SEQUENCE: 30
ccauuuuuau guuauauguu uacaagcccc acaccaggcu gaaaaucugc agaauucgcc 60

-continued

```
cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu ugggcgugcc    300

cccgcaagac ugcuagccga guaguguugg gucgcgaaag gccuuguggu acugccacua    360

ucggugcuug cgagugcccc gggaggucuc guagaccgug caccaugagc acgaauccua    420

aaccucaaag aaaaaccaaa cguaacaguc ucuuaaaaaa caaacaaacg aacgaacagc    480

aagggagcug gguaugacaa cacauacuau aauucuagua cucaggaugc ugaaacagga    540

ggauugccug acugggagau auaaggagaa ucuguuguca cccccacccc uccccauaaa    600

ggcagaauaa aagaacgucc uauaaacaaa uaaacaaaca acccaauaaa acaaaaccaa    660

gaucucucca ccuuuucuuu gcuuuuucag acuuuguaau aaggcccuuu ggagugcagg    720

auauucggca ggacaagcag agagggagac caucaguucu uucuuugauc aagaagacua    780

uguuccuuag caaacuggug uguauuaucu cuuaugcaau gagccuggaa agagggcaca    840

gccaccgagg augguacagc auggauggau gguacgcuac agagacucgg gagcccaacu    900

gugaguggcu gacuggcaug guagguucag ggaagaauug gccugugaag aaaauguucu    960

ugaaaaguga acaaggugca ggagguagga gugggguccug ggcaaagcag ggggugcauc   1020

ccagccucag ggaauagcac agcagagguc uguugaugca ugcgagugca ugaccugcuu   1080

gccaauagac gaucaagaau gggcaaagca ucaugggguga ugagugggag aggggaugag   1140

acauuccuuu cucccugcug agacuuccau ugaaccgaug aguucugaau agaagaugcc   1200

cccccacccc cccaccagug uagaaucuga agggaggcau auauuacccu auauuacucu   1260

guguuggcgg cgagcuaucu gacagccaac cuucccauac auuucauugg gcauacacua   1320

augacaggaa guuccuuuug cuuguaugca agagauggcu cacacgaugg agaauuuaau   1380

cuugaagggc gaauuccacc acacuggacu aguggauccg agcucgguac caagcuu      1437
```

<210> SEQ ID NO 31
<211> LENGTH: 446
<212> TYPE: RNA
<213> ORGANISM: Artificial Sequence
<220> FEATURE:
<223> OTHER INFORMATION: HCV(d) miniIRUP

<400> SEQUENCE: 31

```
ccauuuuuau guuauauguu uacaagcccc acaccaggcu gaaaaucugc agaauucgcc     60

cuugccagcc cccugauggg ggcgacacuc caccaugaau cacuccccug ugaggaacua    120

cugucuucac gcagaaagcg ucuagccaug gcguuaguau gagugucgug cagccuccag    180

gacccccccu cccgggagag ccauaguggu cugcggaacc ggugaguaca ccggaauugc    240

caggacgacc ggguccuuuc uuggauaaac ccgcucaaug ccuggagauu ugggcgugcc    300

cccgcaagac ugcuagccga guaguguugg gucgcgaaag gccuuguggu acugccugau    360

agggugcuug cgagugcccc gggaggucuc guagaccgug caccaugagc acgaauccua    420

aaccucaaag aaaaaccaaa cguaac                                         446
```

<210> SEQ ID NO 32
<211> LENGTH: 375
<212> TYPE: RNA
<213> ORGANISM: Artificial Sequence
<220> FEATURE:

-continued

<223> OTHER INFORMATION: Polio(d) miniIRUP

<400> SEQUENCE: 32
ccauuuuuau guuauauguu uacaagcccc acaccaggcu gaaaaucugc agaauucgcc 60
cuuaugaguc uggacauccc ucaccgguga cgguggucca ggcugcguug gcggccuacc 120
uauggcuaac gccaugggac gcuaguugug aacaaggugu gaagagccua uugagcuaca 180
uaagaauccu ccggccccug aaugcggcua aucccaaccu cggagcaggu ggucacaaac 240
cagugauugg ccugucguaa cgcgcaaguc cguggcggaa ccgacuacuu ugggguguccg 300 uguuuccuuu uauuuuauug uggcugcuua uggugacaau cacagauugu uaucauaaag 360
cgaauuggau uggcc 375

<210> SEQ ID NO 33
<211> LENGTH: 375
<212> TYPE: RNA
<213> ORGANISM: Artificial Sequence
<220> FEATURE:
<223> OTHER INFORMATION: Polio(i) miniIRUP

<400> SEQUENCE: 33
ccauuuuuau guuauauguu uacaagcccc acaccaggcu gaaaaucugc agaauucgcc 60
cuuggccaau ccaauucgcu uuaugauaac aaucugugau ugucaccaua agcagccaca 120
auaaaauaaa aggaaacacg gacacccaaa guagucgguu ccgccacgga cuugcgcguu 180
acgacaggcc aaucacuggu uugugaccac cugcuccgag guugggauua gccgcauuca 240
ggggccggag gauucuuaug uagcucaaua ggcucuucac accuuguuca caacuagcgu 300
cccauggcgu uagccauagg uaggccgcca acgcagccug gaccaccguc accggugagg 360
gauguccaga cucau 375

<210> SEQ ID NO 34
<211> LENGTH: 111
<212> TYPE: RNA
<213> ORGANISM: Artificial Sequence
<220> FEATURE:
<223> OTHER INFORMATION: cMYC short variant(d) miniIRUP

<400> SEQUENCE: 34
ccauuuuuau guuauauguu uacaagcccc acaccaggcu gaaaaucugc agaauucgcc 60
cuugggcacu uugcacugga acuuacaaca cccgagcaag gacgcgacuc u 111

<210> SEQ ID NO 35
<211> LENGTH: 488
<212> TYPE: RNA
<213> ORGANISM: Artificial Sequence
<220> FEATURE:
<223> OTHER INFORMATION: HCV(d) miniIRUP

<400> SEQUENCE: 35
ccagugaaca gcuccucgcc cuugcucacc augguggcga ccgguagcgc uagcggaucu 60
gacgguucac uagaugcggc cgccacugug cuggaauucg cccuugccag cccccugaug 120
ggggcgacac uccaccauga aucacucccc ugugaggaac uacugucuuc acgcagaaag 180
cgucuagcca uggcguuagu augagugucg ugcagccucc aggacccccc cucccgggag 240
agccauagug gucugcggaa ccggugagua caccggaauu gccaggacga ccggguccuu 300
ucuuggauaa acccgcucaa ugccuggaga uuugggcgug cccccgcaag acugcuagcc 360
gaguaguguu gggucgcgaa aggccuugug guacugccug auagggugcu ugcgagugcc 420
ccgggagguc ucguagaccg ugcaccauga gcacgaaucc uaaaccucaa agaaaaacca 480
aacguaac 488

<210> SEQ ID NO 36
<211> LENGTH: 383
<212> TYPE: RNA
<213> ORGANISM: Hepatitis C virus

<400> SEQUENCE: 36
gccagccccc ugaugggggc gacacuccac caugaaucac uccccuguga ggaacuacug 60
ucuucacgca gaaagcgucu agccauggcg uuaguaugag ugucgugcag ccuccaggac 120
ccccccuccc gggagagcca uaguggucug cggaaccggu gaguacaccg gaauugccag 180
gacgaccggg uccuuucuug gauaaacccg cucaaugccu ggagauuugg gcgugccccc 240
gcaagacugc uagccgagua guguuggguc gcgaaaggcc uugugguacu gccugauagg 300
gugcuugcga gugccccggg aggucucgua gaccgugcac caugagcacg aauccuaaac 360
cucaaagaaa aaccaaacgu aac 383

<210> SEQ ID NO 37
<211> LENGTH: 383
<212> TYPE: RNA
<213> ORGANISM: Hepatitis C virus

<400> SEQUENCE: 37
guuacguuug guuuuucuuu gagguuuagg auucgugcuc auggugcacg gucuacgaga 60
ccucccgggg cacucgcaag cacccuauca ggcaguacca caaggccuuu cgcgacccaa 120
cacuacucgg cuagcagucu ugcgggggca cgcccaaauc uccaggcauu gagcggguuu 180
auccaagaaa ggacccgguc guccuggcaa uuccggugua cucaccgguu ccgcagacca 240
cuauggcucu cccgggaggg gggguccugg aggcugcacg acacucauac uaacgccaug 300
gcuagacgcu uucugcguga agacaguagu uccucacagg ggagugauuc auggugcagu 360
gucgccccca ucagggggcu ggc 383

<210> SEQ ID NO 38
<211> LENGTH: 312
<212> TYPE: RNA
<213> ORGANISM: Human poliovirus

<400> SEQUENCE: 38
augagucugg acaucccuca ccggugacgg ugguccaggc ugcguuggcg gccuaccuau 60
ggcuaacgcc augggacgcu aguugugaac aaggugugaa gagccuauug agcuacauaa 120
gaauccuccg gccccugaau gcggcuaauc ccaaccucgg agcaggugggu cacaaaccag 180 ugauuggccu gucguaacgc gcaaguccgu ggcggaaccg acuacuuugg guguccgugu 240
uuccuuuuau uuuauugugg cugcuuaugg ugacaaucac agauuguuau cauaaagcga 300
auuggauugg cc 312

<210> SEQ ID NO 39
<211> LENGTH: 312
<212> TYPE: RNA
<213> ORGANISM: Human poliovirus

<400> SEQUENCE: 39
ggccaaucca auucgcuuua ugauaacaau cugugauugu caccauaagc agccacaaua 60

-continued aaauaaaagg aaacacggac acccaaagua gucgguuccg ccacggacuu gcgcguuacg 120
acaggccaau cacugguuug ugaccaccug cuccgagguu gggauuagcc gcauucaggg 180
gccggaggau ucuuauguag cucaauaggc ucuucacacc uuguucacaa cuagcguccc 240
auggcguuag ccauagguag gccgccaacg cagccuggac caccgucacc ggugagggau 300
guccagacuc au 312

<210> SEQ ID NO 40
<211> LENGTH: 576
<212> TYPE: RNA
<213> ORGANISM: Encephalomyocarditis virus

<400> SEQUENCE: 40
cccccccucu cccucccccc ccccuaacgu uacuggccga agccgcuugg aauaaggccg 60
gugugcguuu gucuauaugu uauuuuccac cauauugccg ucuuuuggca augugagggc 120
ccggaaaccu ggcccugucu ucuugacgag cauuccuagg ggucuuuccc cucucgccaa 180
aggaaugcaa ggucuguuga augucgugaa ggaagcaguu ccucuggaag cuucuugaag 240
acaaacaacg ucuguagcga cccuuugcag gcagcggaac cccccaccug gcgacaggug 300
ccucugcggc caaaagccac guguauaaga uacaccugca aaggcggcac aaccccagug 360
ccacguugug aguuggauag uuguggaaag agucaaaugg cucuccucaa gcguauucaa 420
caaggggcug aaggaugccc agaagguacc ccauuguaug ggaucugauc uggggccucg 480
gugcacaugc uuuacaugug uuuagucgag guuaaaaaac gucuaggccc cccgaaccac 540
ggggacgugg uuuuccuuug aaaaacacga ugauaa 576

<210> SEQ ID NO 41
<211> LENGTH: 576
<212> TYPE: RNA
<213> ORGANISM: Encephalomyocarditis virus

<400> SEQUENCE: 41
uuaucaucgu guuuuucaaa ggaaaaccac guccccgugg uucggggggc cuagacguuu 60
uuuaaccucg acuaaacaca uguaaagcau gugcaccgag gccccagauc agaucccaua 120
caauggggua ccuucugggc auccuucagc cccuuguuga auacgcuuga ggagagccau 180
uugacucuuu ccacaacuau ccaacucaca acguggcacu gggguugugc cgccuuugca 240
gguguaucuu auacacgugg cuuuuggccg cagaggcacc ugucgccagg uggggggguuc 300 cgcugccugc aaagggucgc uacagacguu guuugucuuc aagaagcuuc cagaggaacu 360
gcuuccuuca cgacauucaa cagaccuugc auuccuuugg cgagagggga aagaccccua 420
ggaaugcucg ucaagaagac agggccaggu uuccgggccc ucacauugcc aaaagacggc 480
aauauggugg aaaauaacau auagacaaac gcacaccggc cuuauuccaa gcggcuucgg 540
ccaguaacgu uagggggggg ggagggagag gggggg 576

<210> SEQ ID NO 42
<211> LENGTH: 192
<212> TYPE: RNA
<213> ORGANISM: Cricket paralysis virus

<400> SEQUENCE: 42
aaagcaaaaa ugugaucuug cuuguaaaua caauuuugag agguuaauaa auuacaagua 60
gugcuauuuu uguauuuagg uuagcuauuu agcuuuacgu uccaggaugc cuaguggcag 120
ccccacaaua uccaggaagc ccucucugcg guuuuucaga uuagguaguc gaaaaaccua 180
agaaauuuac cu 192

<210> SEQ ID NO 43
<211> LENGTH: 192
<212> TYPE: RNA
<213> ORGANISM: Cricket paralysis virus

<400> SEQUENCE: 43
agguaaauuu cuuagguuuu ucgacuaccu aaucugaaaa accgcagaga gggcuuccug 60
gauauugugg ggcugccacu aggcauccug gaacguaaag cuaaauagcu aaccuaaaua 120
caaaaauagc acuacuugua auuuauuaac cucucaaaau uguauuuaca agcaagauca 180
cauuuuugcu uu 192

<210> SEQ ID NO 44
<211> LENGTH: 231
<212> TYPE: RNA
<213> ORGANISM: Homo sapiens

<400> SEQUENCE: 44
cagagaucca ggggaggcgc cugugaggcc cggaccugcc ccggggcgaa ggguaugugg 60
cgagacagag cccugcaccc cuaauucccg guggaaaacu ccuguugccg uuucccucca 120
ccggccugga gucucccagu cuugucccgg cagugccgcc cuccccacua agaccuaggc 180
gcaaaggcuu ggcucauggu ugacagcuca gagagagaaa gaucugaggg a 231

<210> SEQ ID NO 45
<211> LENGTH: 231
<212> TYPE: RNA
<213> ORGANISM: Homo sapiens

<400> SEQUENCE: 45
ucccucagau cuuucucucu cugagcuguc aaccaugagc caagccuuug cgccuagguc 60 uuaguggggga gggcggcacu gccgggacaa gacugggaga cuccaggccg guggagggaa 120
acggcaacag gaguuuucca ccgggaauua ggggugcagg gcucugucuc gccacauacc 180
cuucgccccg gggcagguccc gggccucaca ggcgccuccc cuggaucucu g 231

<210> SEQ ID NO 46
<211> LENGTH: 460
<212> TYPE: RNA
<213> ORGANISM: Homo sapiens

<400> SEQUENCE: 46
acuuuuggug ggcauuuaaa aaugugugug uauguguaua uauguaugug uauguaugug 60
uauauaugua uauguaugua uguaucgcgu guaugugugu auguaugcau guguauguau 120
guauaugcau guauguguau guguauauau guaugugugu guauguauau gugugugu au 180 guguaugugu guguguaugu guguguguau guauguaugu auguauaugu auuauacaca 240
uauacacaua uugguuuuuu uaaucauuug agaguuaguu gaagauaaaa acccaucacc 300
ccuaaaugua uuccaaagaa uaagaacauu guuuuauaca uagcacacuu aacaaaauca 360
agaaauuuaa cauuaauaca guacuguuac cuaauccgua gucgauuuuc aaauuuuguc 420
aguuguucca auaaaugucu uuauauauuc cccgcccagc 460

<210> SEQ ID NO 47
<211> LENGTH: 460
<212> TYPE: RNA

-continued

<213> ORGANISM: Homo sapiens

<400> SEQUENCE: 47
gcugggcggg gaauauauaa aggacauuau uggaacaacu gacaaaauuu gaaaaucgac 60
uacggauuag guaacaguac uguauuaaug uuaaauuucu ugauuuuguu aagugugcua 120
uguauaaaac aauguucuua uucuuuggaa uacauuuagg ggugaugggu uuuuaucuuc 180
aacuaacucu caaaugauua aaaaaaccaa uauguguaua uguguauaau acauauacau 240
acauacauac auacacacac acauacacac acacauacac auacacacac auauacauac 300
acacacauac auauauacac auacacauac augcauauac auacauacac augcauacau 360
acacacauac acgcgauaca uacauacaua uacauauaua cacauacaua cacauacaua 420
uauacacaua cacacacauu uuuaaaugcc caccaaaagu 460

<210> SEQ ID NO 48
<211> LENGTH: 395
<212> TYPE: RNA
<213> ORGANISM: Homo sapiens

<400> SEQUENCE: 48
aauuccagcg agaggcagag ggagcgagcg ggcggccggc uagggugga a gagccgggcg 60 agcagagcug cgcugcgggc guccugggaa gggagauccg gagcgaauag ggggcuucgc 120
cucuggccca gcccucccgc uugaucccccc aggccagcgg uccgcaaccc uugccgcauc 180
cacgaaacuu ugcccauagc agcgggcggg cacuuugcac uggaacuuac aacacccgag 240
caaggacgcg acucucccga cgcggggagg cuauucugcc cauuugggga cacuuccccg 300
ccgcugccag gacccgcuuc ucugaaaggc ucuccuugca gcugcuuaga cgcuggauuu 360
uuuucgggua guggaaaacc agcagccucc cgcga 395

<210> SEQ ID NO 49
<211> LENGTH: 395
<212> TYPE: RNA
<213> ORGANISM: Homo sapiens

<400> SEQUENCE: 49
ucgcgggagg cugcugguuu uccacuaccc gaaaaaaauc cagcgucuaa gcagcugcaa 60
ggagagccuu ucagagaagc ggguccuggc agcggcgggg aagugucccc aaaugggcag 120
aauagccucc ccgcgucggg agagucgcgu ccuugcucgg guguuguaag uuccagugca 180
aagugcccgc ccgcugcuau gggcaaaguu ucguggaugc ggcaaggguu gcggaccgcu 240
ggccuggggg aucaagcggg agggcugggc cagaggcgaa gcccccuauu cgcuccggau 300
cucccuuccc aggacgcccg cagcgcagcu cugcucgccc ggcucuucca cccuagccgg 360
ccgcccgcuc gcucccucug ccucucgcug gaauu 395

<210> SEQ ID NO 50
<211> LENGTH: 48
<212> TYPE: RNA
<213> ORGANISM: Homo sapiens

<400> SEQUENCE: 50
gggcacuuug cacuggaacu uacaacaccc gagcaaggac gcgacucu 48

<210> SEQ ID NO 51
<211> LENGTH: 48
<212> TYPE: RNA
<213> ORGANISM: Homo sapiens

<400> SEQUENCE: 51
agagucgcgu ccuugcucgg guguuguaag uuccagugca aagugccc 48

<210> SEQ ID NO 52
<211> LENGTH: 71
<212> TYPE: RNA
<213> ORGANISM: Homo sapiens

<400> SEQUENCE: 52
guacugacau cguagaugga aaucauaaac ugacucuugg uuugauuugg aauauaaucc 60
uccacuggca g 71

<210> SEQ ID NO 53
<211> LENGTH: 71
<212> TYPE: RNA
<213> ORGANISM: Homo sapiens

<400> SEQUENCE: 53
cugccagugg aggauuauau uccaaaucaa accaagaguc aguuuaugau uuccaucuac 60
gaugucagua c 71

<210> SEQ ID NO 54
<211> LENGTH: 303
<212> TYPE: RNA
<213> ORGANISM: Hepatitis C virus

<400> SEQUENCE: 54
gccagccccc ugaugggggc gacacuccac caugaaucac cccccucccc gggagagcca 60
uaguggucug cggaaccggu gaguacaccg gaauugccag gacgaccggg uccuuucuug 120
gauaaacccg cucaaugccu ggagauuugg gcgugccccc gcaagacugc uagccgagua 180
guguuggguc gcgaaaggcc uugugguacu gccugauagg gugcuugcga gugccccggg 240
aggucucgua gaccgugcac caugagcacg aauccuaaac cucaaagaaa aaccaaacgu 300
aac 303

<210> SEQ ID NO 55
<211> LENGTH: 367
<212> TYPE: RNA
<213> ORGANISM: Hepatitis C virus

<400> SEQUENCE: 55
gccagccccc ugaugggggc gacacuccac caugaaucac uccccuguga ggaacuacug 60
ucuucacgca gaaagcgucu agccauggcg uuaguaugag ugucgugcag ccuccaggac 120
cccccucccc gggagagcca uaguggucug cggaaaauug ccaggacgac cggguccuuu 180
cuuggauaaa cccgcucaau gccuggagau uugggcgugc ccccgcaaga cugcuagccg 240
aguaguguug ggucgcgaaa ggccuugugg uacugccuga uagggugcuu gcgagugccc 300
cgggaggucu cguagaccgu gcaccaugag cacgaauccu aaaccucaaa gaaaaaccaa 360
acguaac 367

<210> SEQ ID NO 56
<211> LENGTH: 356
<212> TYPE: RNA
<213> ORGANISM: Hepatitis C virus

<400> SEQUENCE: 56

-continued

```
gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gaguacaccg gaauugccag    180

gacgaccggg uccuuucuug gauaaacccg cucaaugccu ggagauuugg gcgugccccc    240

gcaagacugc uacuuguggu acugccugau agggugcuug cgagugcccc gggaggucuc    300

guagaccgug caccaugagc acgaauccua aaccucaaag aaaaaccaaa cguaac        356
```

<210> SEQ ID NO 57
<211> LENGTH: 330
<212> TYPE: RNA
<213> ORGANISM: Hepatitis C virus

<400> SEQUENCE: 57

```
gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gaguacaccg gaauugccag    180

gacgaccggg uccuuucuug gauaaacccg cucaaugccu ggagauuugg gcgugccccc    240

gcaagacugc uagccgagua guguuggguc gcgaaaggcc uugugguacu gccugauagg    300

gugcuugcga gugccccggg aggucucgua                                     330
```

<210> SEQ ID NO 58
<211> LENGTH: 383
<212> TYPE: RNA
<213> ORGANISM: Hepatitis C virus

<400> SEQUENCE: 58

```
gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gaguacaccg gaauugccag    180

gacgaccggg uccuuucuug gauaaacccg cucaaugccu ggagauuugg gcgugccccc    240

gcaagacugc uagccgagua guguucgguc gcgaaaggcc uugugguacu gccugauagg    300

gugcuugcga gugccccggg aggucucgua gaccgugcac caugagcacg aauccuaaac    360

cucaaagaaa aaccaaacgu aac                                            383
```

<210> SEQ ID NO 59
<211> LENGTH: 383
<212> TYPE: RNA
<213> ORGANISM: Hepatitis C virus

<400> SEQUENCE: 59

```
gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gaguacaccg gaauugccag    180

gacgaccggg uccuuucuug gauaaacccg cucaaugccu ggagauucgg gcgugccccc    240

gcaagacugc uagccgagua guguuggguc gcgaaaggcc uugugguacu gccugauagg    300

gugcuugcga gugccccggg aggucucgua gaccgugcac caugagcacg aauccuaaac    360

cucaaagaaa aaccaaacgu aac                                            383
```

<210> SEQ ID NO 60
<211> LENGTH: 383

-continued

<212> TYPE: RNA
<213> ORGANISM: Hepatitis C virus

<400> SEQUENCE: 60
gccagccccc ugaugggggc gacacuccac caugaaucac uccccuguga ggaacuacug 60
ucuucacgca gaaagcgucu agccauggcg uuaguaugag ugucgugcag ccuccaggac 120
ccccccuccc gggagagcca uagugggucug cggaaccggu gaguacaccg gaauugccag 180
gacgaccggg uccuuucuug gauaaacccg cucaaugccu ggagauuugg gcgugccccc 240
gcaagacugc uagccgagua guguugcguc gcgaaaggcc uugugguacu gccugauagg 300
gugcuugcga gugccccggg aggucucgua gaccgugcac caugagcacg aauccuaaac 360
cucaaagaaa aaccaaacgu aac 383

<210> SEQ ID NO 61
<211> LENGTH: 383
<212> TYPE: RNA
<213> ORGANISM: Hepatitis C virus

<400> SEQUENCE: 61
gccagccccc ugaugggggc gacacuccac caugaaucac uccccuguga ggaacuacug 60
ucuucacgca gaaagcgucu agccauggcg uuaguaugag ugucgugcag ccuccaggac 120
ccccccuccc gggagagcca uagugggucug cggaaccggu gaguacaccg gaauugccag 180
gacgaccggg uccuuucuug gauaaacccg cucaaugccu ggagauuugg gcgugccccc 240
gcaagacugc uagccgagua guguuggcuc gcgaaaggcc uugugguacu gccugauagg 300
gugcuugcga gugccccggg aggucucgua gaccgugcac caugagcacg aauccuaaac 360
cucaaagaaa aaccaaacgu aac 383

<210> SEQ ID NO 62
<211> LENGTH: 383
<212> TYPE: RNA
<213> ORGANISM: Hepatitis C virus

<400> SEQUENCE: 62
gccagccccc ugaugggggc gacacuccac caugaaucac uccccuguga ggaacuacug 60
ucuucacgca gaaagcgucu agccauggcg uuaguaugag ugucgugcag ccuccaggac 120
ccccccuccc gggagagcca uagugggucug cggaaccggu gaguacaccg gaauugccag 180
gacgaccggg uccuuucuug gauaaacccg cucaaugccu ggagauuugg gcgugccccc 240
gcaagacugc uagccgagua guguucccuc gcgaaaggcc uugugguacu gccugauagg 300
gugcuugcga gugccccggg aggucucgua gaccgugcac caugagcacg aauccuaaac 360
cucaaagaaa aaccaaacgu aac 383

<210> SEQ ID NO 63
<211> LENGTH: 383
<212> TYPE: RNA
<213> ORGANISM: Hepatitis C virus

<400> SEQUENCE: 63
gccagccccc ugaugggggc gacacuccac caugaaucac uccccuguga ggaacuacug 60
ucuucacgca gaaagcgucu agccauggcg uuaguaugag ugucgugcag ccuccaggac 120
ccccccuccc gggagagcca uagugggucug cggaaccggu gaguacaccg gaauugccag 180
gacgaccggg uccuuucuug gauaaacccg cucaaugccu ggagauuugg gcgugccccc 240

-continued

```
gcaagacugc uagccgagua guguuaguuc gcgaaaggcc uugugguacu gccugauagg    300

gugcuugcga gugccccggg aggucucgua gaccgugcac caugagcacg aauccuaaac    360

cucaaagaaa aaccaaacgu aac                                            383


<210> SEQ ID NO 64
<211> LENGTH: 383
<212> TYPE: RNA
<213> ORGANISM: Hepatitis C virus

<400> SEQUENCE: 64

gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gucaucaccg gaauugccag    180

gacgaccggg uccuuucuug gauaaacccg cucaaugccu ggagauuugg gcgugccccc    240

gcaagacugc uagccgagua guguugggu c gcgaaaggcc uugugguacu gccugauagg    300

gugcuugcga gugccccggg aggucucgua gaccgugcac caugagcacg aauccuaaac    360

cucaaagaaa aaccaaacgu aac                                            383


<210> SEQ ID NO 65
<211> LENGTH: 383
<212> TYPE: RNA
<213> ORGANISM: Hepatitis C virus

<400> SEQUENCE: 65

gccagccccc ugaugggggc gacacuccac caugaaucac uccccuguga ggaacuacug     60

ucuucacgca gaaagcgucu agccauggcg uuaguaugag ugucgugcag ccuccaggac    120

ccccccuccc gggagagcca uaguggucug cggaaccggu gaguacaccg gaauugccag    180

gacgaccggg uccuuucuug gauaaacccg cucaaugccu ggagauuugg gcgugccccc    240

gcaagacugc uagccgagua guguuggguc gcgaaaggcc uugugguacu gccacuaucg    300

gugcuugcga gugccccggg aggucucgua gaccgugcac caugagcacg aauccuaaac    360

cucaaagaaa aaccaaacgu aac                                            383
```